US012653862B2

(12) United States Patent
De Keizer et al.

(10) Patent No.: US 12,653,862 B2
(45) Date of Patent: Jun. 16, 2026

(54) ANTI-SENESCENCE COMPOUNDS AND USES THEREOF

(71) Applicant: CLEARA BIOTECH B.V., Utrecht (NL)

(72) Inventors: Peterus Leonardus Josephus De Keizer, Utrecht (NL); Michael Teifel, Weiterstadt (DE); Tobias Madl, Graz (AT); Benjamin Michel Rene Bourgeois, Graz (AT); Emil Spreitzer, Graz (AT); Yvonne Marie Angell, San Carlos, CA (US); Marjolein Petronella Baar, Bunnik (NL)

(73) Assignee: CLEARA BIOTECH B.V., Utrecht (NL)

( * ) Notice: Subject to any disclaimer, the term of this patent is extended or adjusted under 35 U.S.C. 154(b) by 931 days.

(21) Appl. No.: 17/799,675

(22) PCT Filed: Feb. 22, 2021

(86) PCT No.: PCT/EP2021/054338
§ 371 (c)(1),
(2) Date: Aug. 14, 2022

(87) PCT Pub. No.: WO2021/165538
PCT Pub. Date: Aug. 26, 2021

(65) Prior Publication Data
US 2023/0090099 A1 Mar. 23, 2023

Related U.S. Application Data

(60) Provisional application No. 62/979,819, filed on Feb. 21, 2020.

(51) Int. Cl.
*A61K 38/17* (2006.01)
*A61K 45/06* (2006.01)

(52) U.S. Cl.
CPC .......... *A61K 38/1761* (2013.01); *A61K 45/06* (2013.01)

(58) Field of Classification Search
CPC .... A61K 38/1761; A61K 45/06; A61K 38/00; A61P 35/00; G01N 33/68; C07K 2319/10; C07K 14/4747
See application file for complete search history.

(56) References Cited

FOREIGN PATENT DOCUMENTS

| WO | 2013/152041 A1 | 10/2013 | |
| WO | WO-2016118014 A2 * | 7/2016 | ............. A61K 38/10 |
| WO | 2018/129007 A1 | 7/2018 | |

OTHER PUBLICATIONS

Li et al., Limitations of peptide retro-inverso isomerization in molecular mimicry. J Biol Chem. Jun. 18, 2010;285(25):19572-81. doi: 10.1074/jbc.M110.116814. Epub Apr. 9, 2010. PMID: 20382735; PMCID: PMC2885236 (Year: 2010).*

(Continued)

*Primary Examiner* — Randall L Beane
(74) *Attorney, Agent, or Firm* — SALIWANCHIK, LLOYD & EISENSCHENK

(57) ABSTRACT

The present invention relates to improved compounds for use in the treatment of diseases or conditions where the removal of senescent cells, scarred cells, and/or cancerous cells is beneficial, for example cancer. The invention also relates to methods of treating an individual suffering, or suspected of suffering, from a disease or condition wherein the removal of senescent cells, scarred cells, and/or cancerous cells is beneficial.

6 Claims, 28 Drawing Sheets

Specification includes a Sequence Listing.

(56)     References Cited

OTHER PUBLICATIONS

Baar, Marjolein P. et al. "Targeted apoptosis of senescent cells restores tissue homeostasis in response to chemotoxicity and aging." Cell 169(1):132-147, Mar. 23, 2017.

* cited by examiner

Figure 1

```
        10          20          30          40          50
MDPGNENSAT  EAAAIIDLDP  DFEPQSRPRS  CTWPLPRPEI  ANQPSEPPEV 60          70          80          90         100
EPDLGEKVHT  EGRSEPILLP  SRLPEPAGGP  QPGILGAVTG  PRKGGSRRNA 110         120         130         140         150
WGNQSYAELI  SQAIESAPEK  RLTLAQIYEW  MVRTVPYFKD  KGDSNSSAGW 160         170         180         190         200
KNSIRHNLSL  HSKFIKVHNE  ATGKSSWWML  NPEGGKSGKA  PRRRAASMDS 210         220         230         240         250
SSKLLRGRSK  APKKKPSVLP  APPEGATPTS  PVGHFAKWSG  SPCSRNREEA 260         270         280         290         300
DMWTTFRPRS  SSNASSVSTR  LSPLRPESEV  LAEEIPASVS  SYAGGVPPTL 310         320         330         340         350
NEGLELLDGL  NLTSSHSLLS  RSGLSGFSLQ  HPGVTGPLHT  YSSSLFSPAE 360         370         380         390         400
GPLSAGEGCF  SSSQALEALL  TSDTPPPPAD  VLMTQVDPIL  SQAPTLLLLG 410         420         430         440         450
GLPSSSKLAT  GVGLCPKPLE  APGPSSLVPT  LSMIAPPPVM  ASAPIPKALG 460         470         480         490         500
TPVLTPPTEA  ASQDRMPQDL  DLDMYMENLE  CDMDNIISDL  MDEGEGLDFN

FEPDP
```

Figure 2
A)
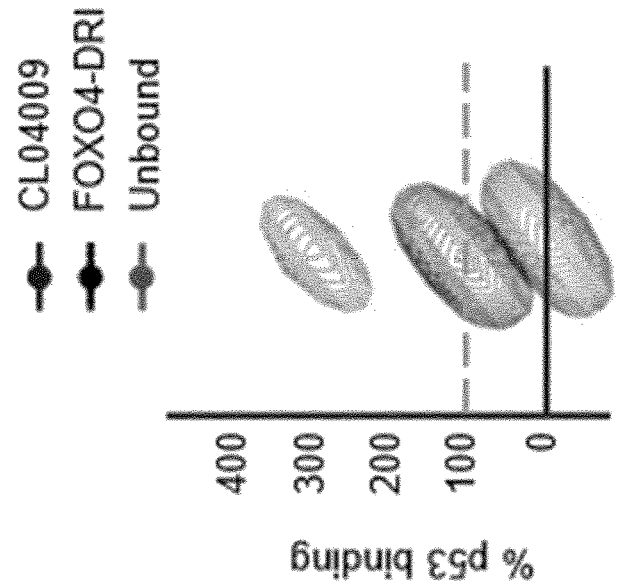
B)
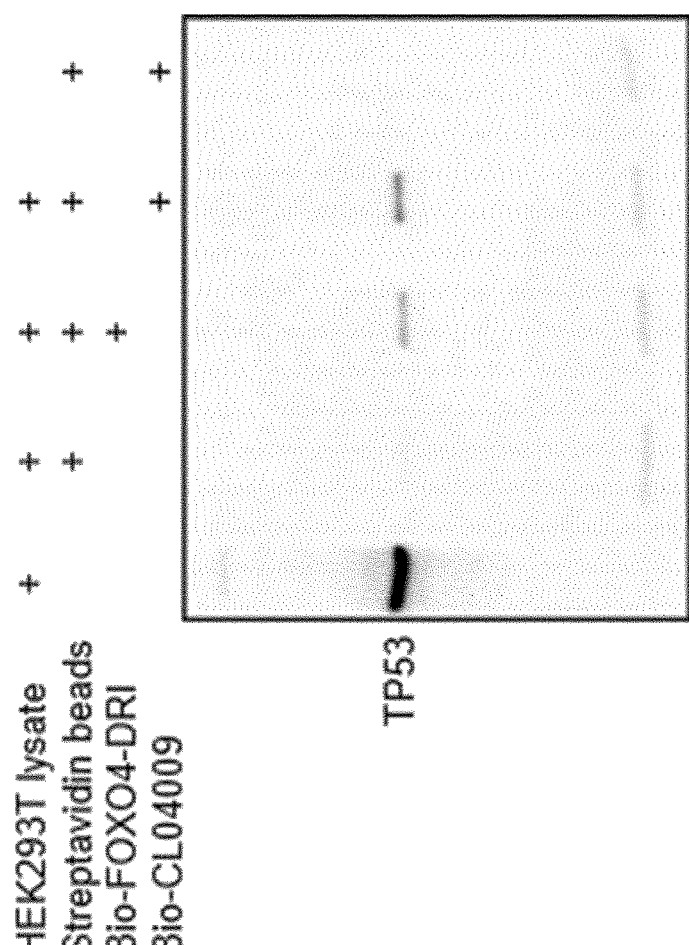

Figure 7
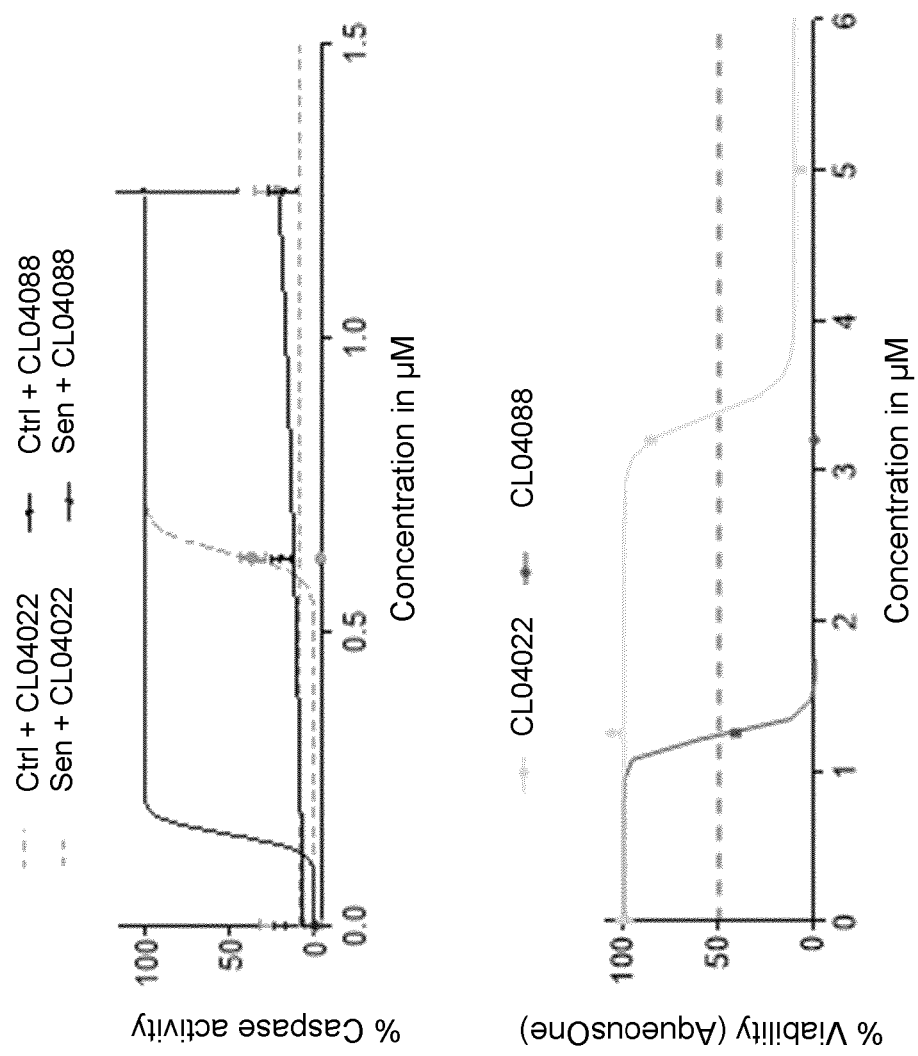
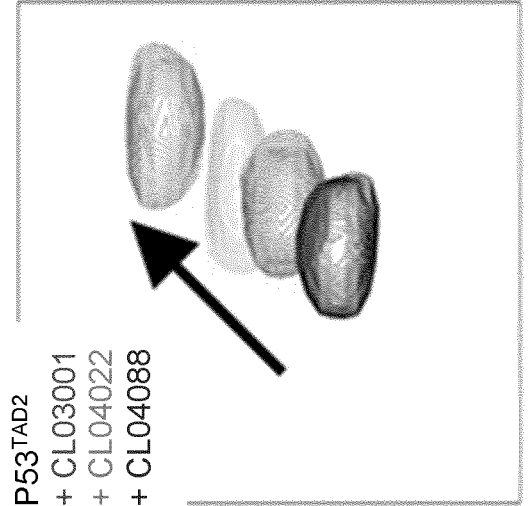

Figure 9
A)
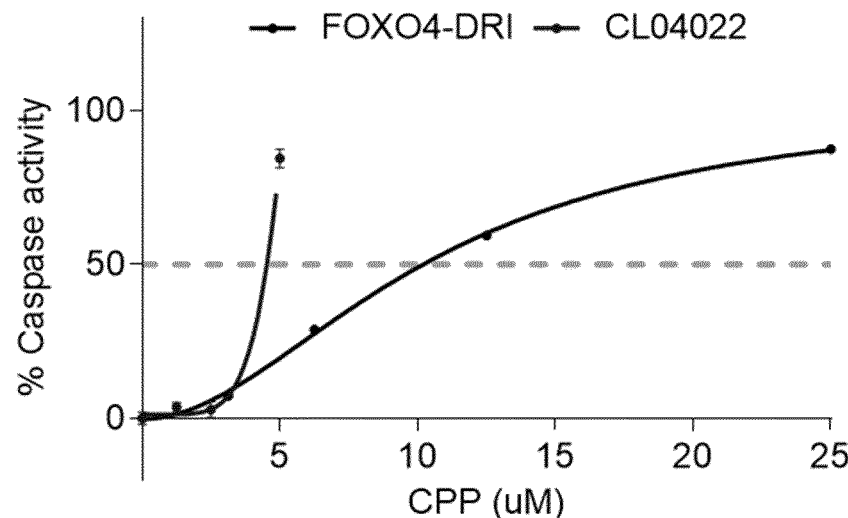
B)
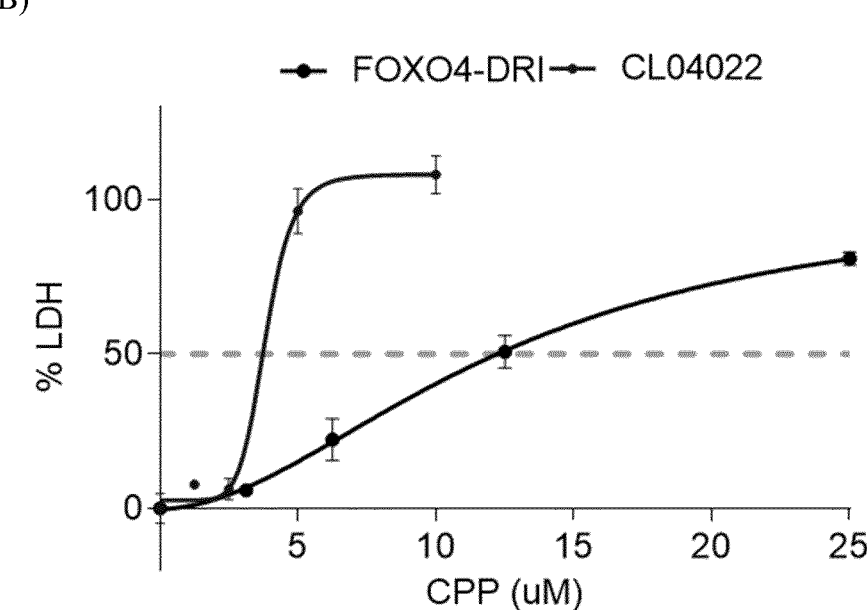

C)

Figure 10
A)
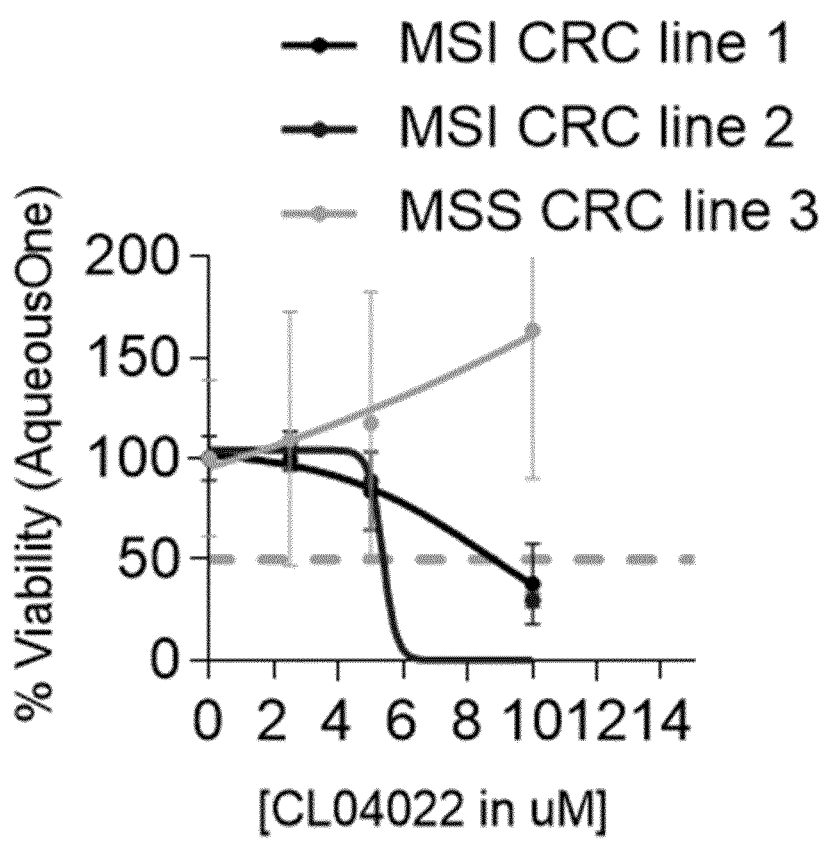
B)
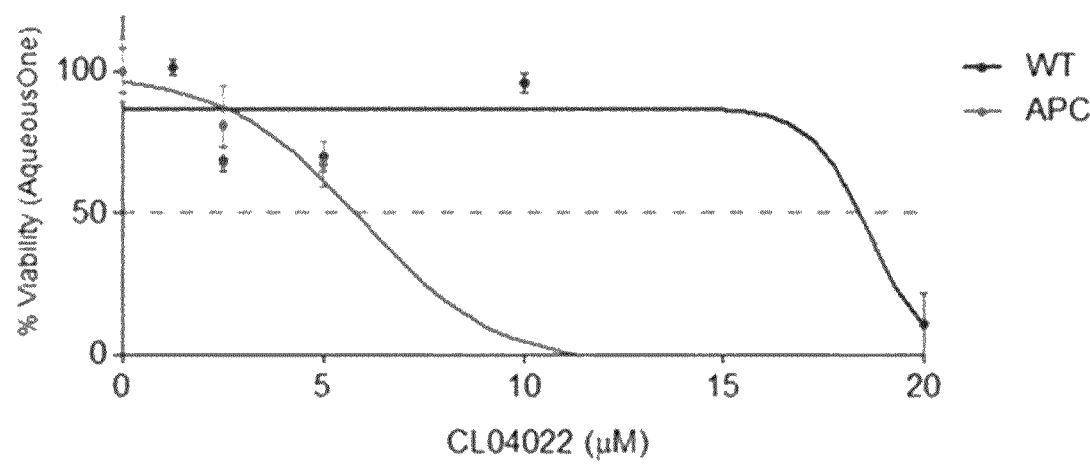

A)

B)

| Compound | Matrix | $t_{1/2}$ [h] |
|---|---|---|
| CL03001 | PBS | 24 |
| CL04183 | PBS | >1105 |
| CL05114 | PBS | >1105 |
| CL02001 | PBS | 311 |
| CL02015 | PBS | 1028 |

A)

B)

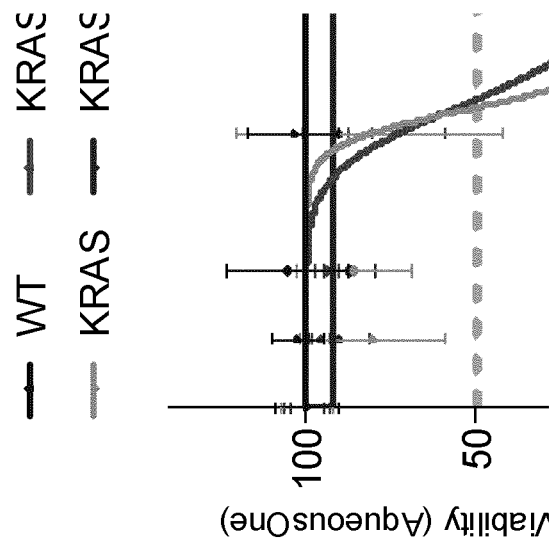
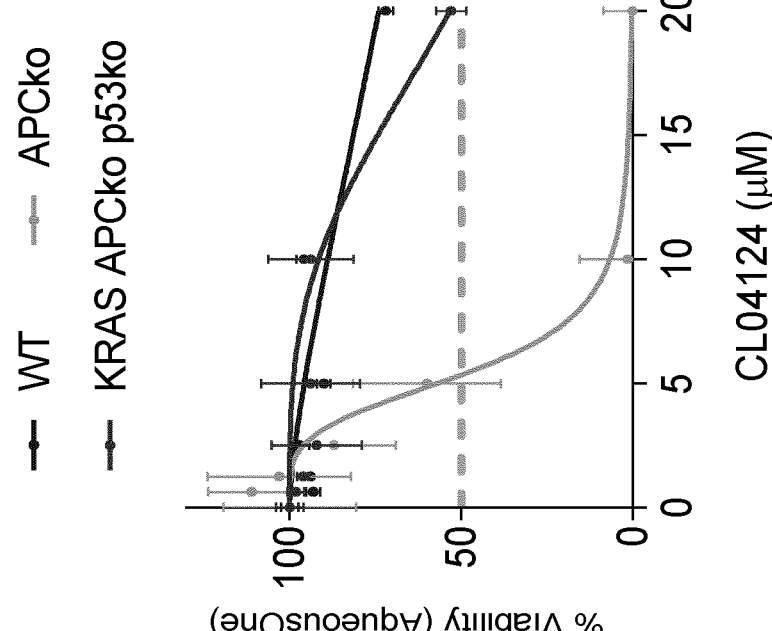
Figure 15

Figure 19
A)
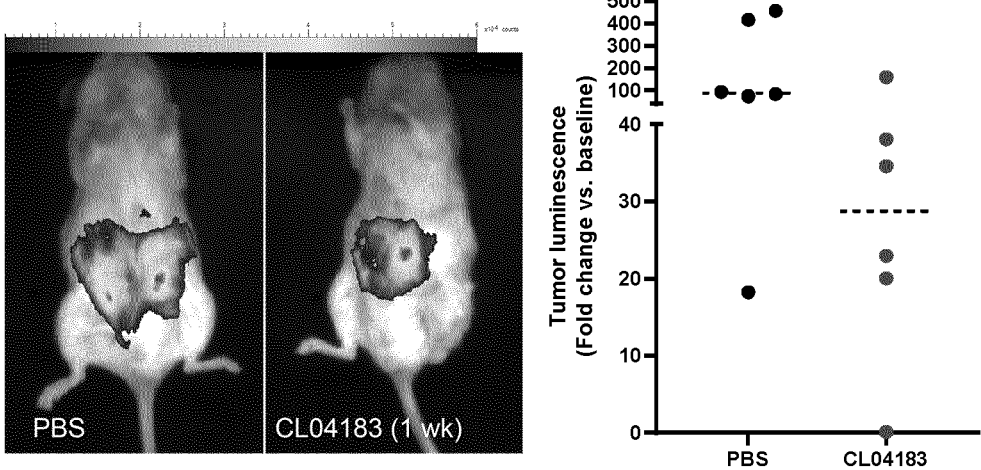
B
Lung
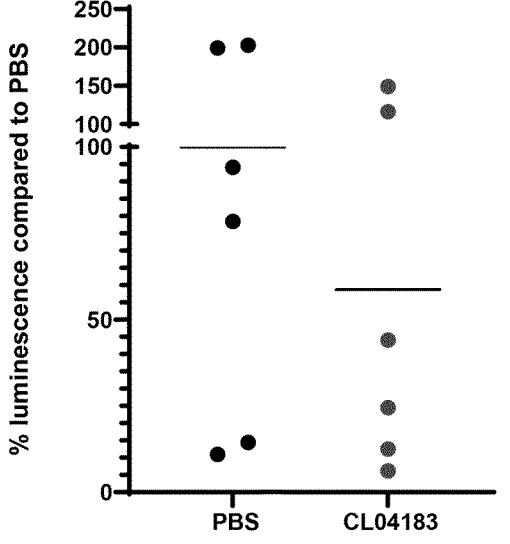
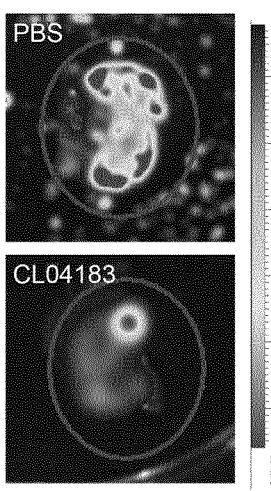

Figure 20
A
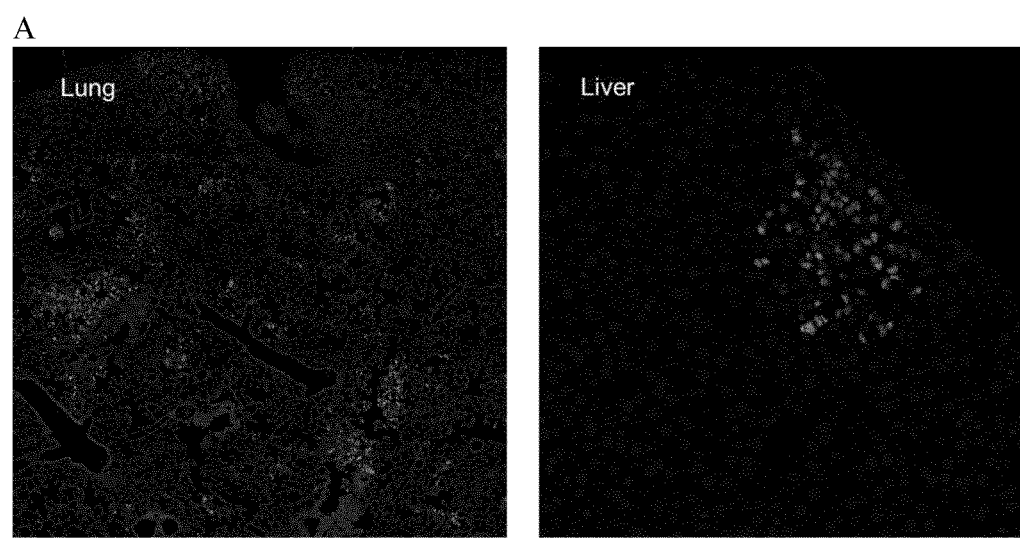
B
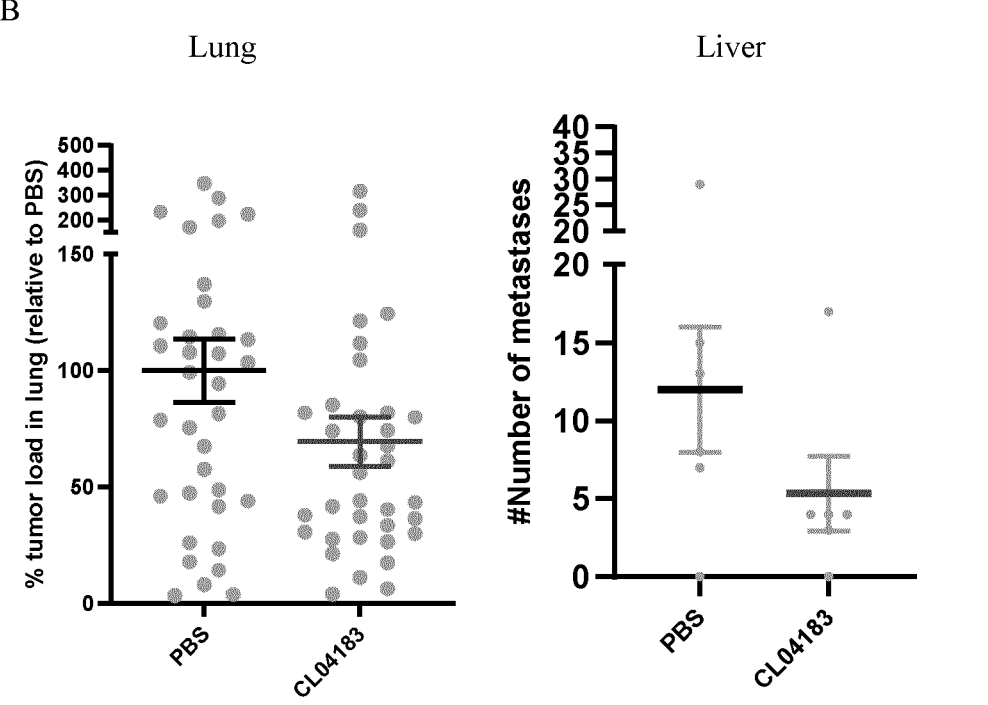

Figure 21
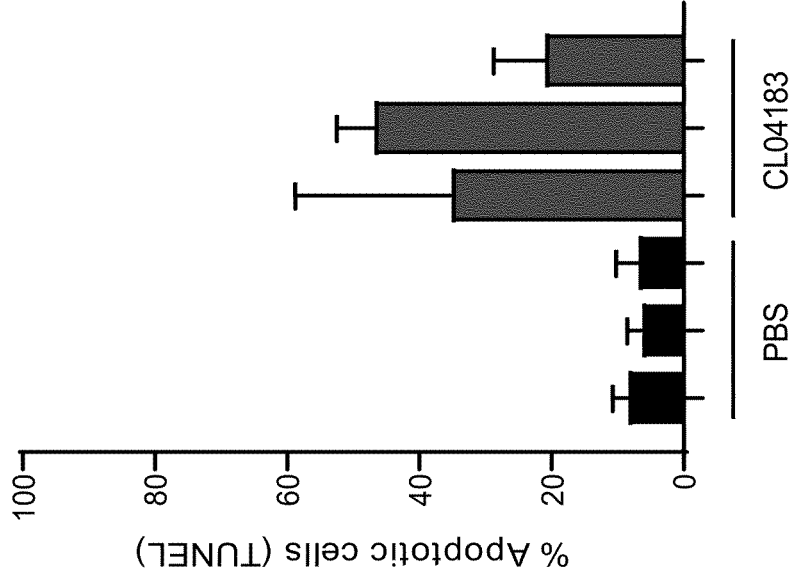
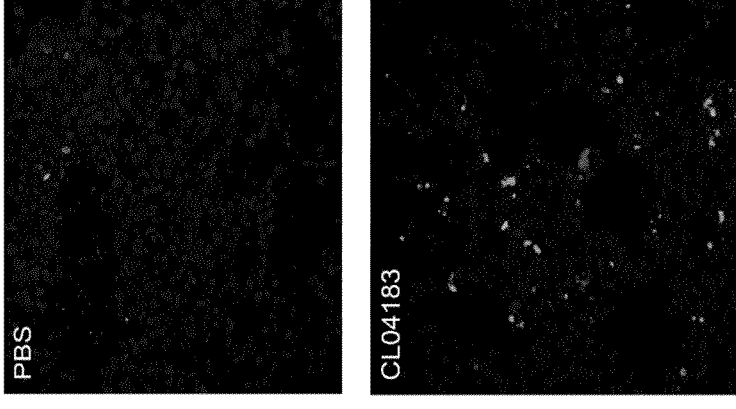

A)

B)

Figure 26
A
B
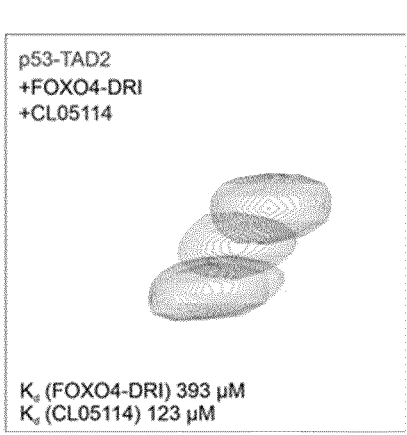

ANTI-SENESCENCE COMPOUNDS AND USES THEREOF

CROSS REFERENCE TO RELATED APPLICATIONS

This application is a National Stage Application of International Application Number PCT/EP2021/054338, filed Feb. 22, 2021; which claims the benefit of U.S. Provisional Application Ser. No. 62/979,819, filed Feb. 21, 2020.

The Sequence Listing for this application is labeled "SeqList-10Aug22-ST25.txt", which was created on Aug. 10, 2022 and is 34 KB. The entire content is incorporated herein by reference in its entirety.

The present invention relates to improved compounds for use in the treatment of diseases or conditions where the removal of senescent cells, scarred cells, and/or cancerous cells is beneficial, for example cancer. The invention also relates to methods of treating an individual suffering, or suspected of suffering, from a disease or condition wherein the removal of senescent cells, scarred cells, and/or cancerous cells is beneficial.

BACKGROUND OF THE INVENTION

Apoptosis (programmed cell death) provides for the killing of damaged cells. Dying cells that undergo the final stages of apoptosis display phagocytic molecules, marking these cells for phagocytosis by cells possessing the appropriate receptors, such as macrophages.

Senescent cells are thought to impair tissue function and their genetic clearance can delay features of aging. Senescent cells are permanently withdrawn from the cell cycle and generally develop a persistent pro-inflammatory phenotype, called the Senescence-Associated Secretory Phenotype or SASP. The SASP influences the cellular microenvironment, which can be beneficial early in life, or in an acute setting of wound healing. However, unlike apoptotic cells, which are permanently eliminated, senescent cells can prevail for prolonged periods of time and accumulate with age. Because of their low, but chronic SASP, persistent senescent cells are thought to accelerate aging and the onset of age-related diseases.

It has been shown that senescent cells accumulate with age, and at sites of age-related pathology. Further, senescent cells can acquire mutations that allow them to re-enter a proliferative state. Benign senescent lesions thus retain the capacity to become malignant. Indeed, senescence has been associated with a plethora of (age-related) pathologies and, conversely, genetic clearance of senescent cells can delay features of aging.

Indeed, it was recently shown that clearance of senescent cells in a genetic fashion could markedly improve the fitness and decrease parameters of aging in a mouse model for accelerated aging. These mice showed reduced signs of aging measured by kyphosis (excessive bone curvature), muscle strength, fat deposition and cataracts. This provided further evidence that cellular senescence and the SASP is causally linked to age-associated phenotypes and cancer (Baker et al., 2011. Nature 479(7372):232-6). This proof-of-concept evidence was obtained in a genetic fashion that has poor therapeutic applicability.

Studies have consistently revealed FOXO (Forkhead box 0) transcription factors as important determinants in aging and longevity. FOXO proteins represent a subfamily of transcription factors conserved from *Caenorhabditis elegans* to mammals that act as key regulators of longevity downstream of insulin and insulin-like growth factor signaling. Invertebrate genomes have one FOXO gene, while mammals have four FOXO genes: FOXO1, FOXO3, FOXO4, and FOXO6. In mammals, this subfamily is involved in a wide range of crucial cellular processes regulating stress resistance, metabolism, cell cycle arrest, and apoptosis. Their role in longevity determination is complex and remains to be fully elucidated.

Bourgeois and Madl (in: Regulation of cellular senescence via the FOXO4-p53 axis. FEBS Lett. 2018 June; 592(12):2083-2097) disclose that in the last decade both FOXO and p53 have been identified as key players in aging, and their misregulation is linked to numerous diseases including cancers. However, many of the underlying molecular mechanisms are said to remain mysterious, including regulation of ageing by FOXOs and p53. Several activities appear to be shared between FOXOs and p53, including their central role in the regulation of cellular senescence. They focus on the recent advances on the link between FOXOs and p53, with a particular focus on the FOXO4-p53 axis and the role of FOXO4/p53 in cellular senescence. Potential strategies for targeting the FOXO4-p53 interaction to modulate cellular senescence as a drug target in treatment of aging-related diseases and morbidity are discussed.

WO 2013/152038 relates to uses of agents that inhibit Jun kinases and/or FOXO4 in treating cancer and/or removing senescent cells in an individual. In some embodiments, the agent is a small molecule such as SP600125. In some embodiments, the agent is a small molecule such as AS601245. In some embodiments, the agent is a peptide as disclosed.

WO 2013/152041 relates to agents that inhibit FOXO4 function and uses thereof in treating cancer and/or removing senescent cells in an individual. In some embodiments, the agent that inhibits FOXO4 is a peptide that inhibits FOXO4 function in a cell, wherein the peptide comprises an amino acid sequence that has at least 80% identity to a fragment of the FOXO4 as disclosed.

WO 2016/118014 relates to a peptide comprising the amino acid sequence LTLRKEPASEIAQSILEAYSQNG-WANRRSGGKRP (SEQ ID NO: 5), wherein the amino acids in said amino acid sequence are D-amino acid residues, and to methods for the use of this peptide in the treatment of age-related disorders. The peptide exhibits apoptosis-inducing activity in senescent cells or cells having an increased FOXO4 expression as compared to a control cell and expressing Ser15 phosphorylated p53 (pSer15-p53).

WO 2018/129007 relates to conditionally active proteins that target senescent cells and to methods of generating such conditionally active proteins.

It is clear from the above that there is still a need in the art for compounds that selectively induce apoptosis in senescent cells, as cellular senescence is linked to degenerative (loss-of-function) diseases and cancer (gain of function). There are currently no suitable therapeutically applicable compounds that can selectively induce apoptosis in senescent cells in vivo.

It is therefore an object of the present invention, to provide new improved compounds that therapeutically target senescent cells and that can be efficiently used in the treatment of diseases associated with cellular senescence.

In a first aspect thereof, the present invention solves this problem by providing a compound that is selected from i) a peptide comprising an amino acid sequence that is at least 70%, preferably at least 80%, and more preferably at least 90%, most preferably more than 95% identical to the amino acid sequence $$X_3X_2X_4X_5X_7X_5X_4X_4X_6X_{18}X_8X_3QNX_9X_8X_{10}X_{10}X_{11}X_{12}S^*X_{13}X_{14}X_{11}X_{11},$$ (SEQ ID NO: 1)

wherein

S* can be S or is absent;

$X_2$ is absent or is selected from K, E, R, and H;

$X_3$ is absent or selected from A, J, and S;

$X_4$ is selected from I, Z, and L, wherein Z is Cyclo-Hexyl-Alanine;

$X_5$ is selected from A, G, S, E, and D;

$X_6$ is selected from E and D;

$X_7$ is selected from J, G, Q, A, S, and P;

$X_8$ is selected from B, W, Y, and F, wherein B is 2-Methyl-Tryptophan;

$X_9$ is absent or is selected from A and G;

$X_{10}$ is absent or is selected from A and N;

$X_{11}$ is selected from R and K;

$X_{12}$ is absent or is selected from R;

$X_{13}$ is absent or is selected from G and S;

$X_{14}$ is absent or is selected from A and C; and $X_{18}$ is selected from A and E;

with the provisio that either none or two Js are present that form a staple;

ii) the peptide according to i) comprising non-natural amino acids, and/or D-amino acids, and preferably the peptide according to i) comprising at least 80%, preferably at least 90%, more preferably at least 95% or consisting of at least 80% preferably of at least 90%, and more preferably of at least 95% D-amino acids, and iii) a retro inverso peptide according to i) or ii), i.e. a peptide in which the amino acid sequence is reversed and placed in the D-instead of the L-isoform when compared to the native protein sequence, and pharmaceutically acceptable salts thereof; and wherein said compound induces apoptosis in senescent, scarred cells, and/or cancerous cells.

Preferred is the compound according to the present invention, wherein said peptide comprises an amino acid sequence that is at least 70%, preferably at least 80%, and more preferably at least 90% identical to the amino acid sequence $$X_1X_{17}K^*X_2X_{16}X_3X_3X_2X_4X_5X_7X_5X_4X_4X_6AX_8X_3QNX_9X_8X_{10}X_{10}X_{11}X_{12}S^*X_{13}$$
$$X_{14}X_{11}X_{11}X_{15},$$ (SEQ ID NO: 2)

wherein Z, B, J, S*, $X_2$, $X_3$, $X_4$, $X_5$, $X_6$, $X_7$, $X_8$, $X_9$, $X_{10}$, $X_{11}$, $X_{12}$, $X_{13}$, $X_{14}$, and $X_{18}$ are as above;

K* can be K or is absent;

$X_1$ is absent or indicates the amino acid sequence LTL;

$X_{15}$ is absent or is selected from A and C;

$X_{16}$ is selected from A, and P; and $X_{17}$ is absent or is selected from R and S; and wherein said compound induces apoptosis in senescent, scarred cells, and/or cancerous cells.

More preferably, the compound according to the present invention comprises the amino acid motif $X_3QNX_9X_8$ (e.g. starting at position 18 of SEQ ID NO: 2) that is selected from SQNAW (SEQ ID NO: 43), SQNGW (SEQ ID NO: 44) and SQN-W (SEQ ID NO: 45), wherein "-" indicates an absent amino acid. Even more preferably, the compound according to the present invention comprises the amino acid motif $X_2X_4X_5X_7X_5$ (e.g. starting at position 8 of SEQ ID NO: 2) that is selected from KIAAA (SEQ ID NO: 46), KIEAA (SEQ ID NO: 47), KIAAE (SEQ ID NO: 48) and KIEAE (SEQ ID NO: 49).

Still more preferably, the compound according to the present invention comprises the amino acid motif $X_4X_5X_7X_5X_4X_4X_6AX_8X_3QNX_9X_8$ (SEQ ID NO: 3, starting at position 9 of SEQ ID NO: 2) that is selected from the general formula $$IX_5X_7X_5ILX_6AYX_3QNX_9W,$$ (SEQ ID NO: 4)

wherein $X_3$ is absent or selected from A, J, and S;

$X_5$ is selected from A, G, S, E, and D;

$X_6$ is selected from E and D;

$X_7$ is selected from J, G, Q, A, S, and P; and $X_9$ is absent or is selected from A and G.

Preferably, the compound according to the present invention consists of D-amino acids. Designation of amino acids is according to the standard one-letter code.

Most preferably, the compound according to the present invention is a peptide comprising an amino acid sequence selected from

LTLRKEASSEIAQSILDAYSQNGWANRRSSCKRP, (SEQ ID NO: 7)

LTLRKKASSKIAQSILDAFSQNGWANRRSSCKRP, (SEQ ID NO: 8)

LTLRKEPASEIAQSILEAYSQNGWANRRSGGKRP, (SEQ ID NO: 9)

RKKASSKIAQSILDAFSQNGWANRRSSCKRP, (SEQ ID NO: 10)

RKKASSKIAAAILDAFSQNGWANRRSSCKRP, (SEQ ID NO: 11)

RKKASSKIAAAILDAFSQNAWANRRSSCKRP, (SEQ ID NO: 12)

RKKASSKIAAAILDAFSQNWRRKR, (SEQ ID NO: 13)

RKKASSKIEAAILDAFSQNWRRKR, (SEQ ID NO: 14)

RKKASSKIAAEILDAFSQNWRRKR, (SEQ ID NO: 15)

RKKASSKIEAEILDAFSQNWRRKR, (SEQ ID NO: 16)

RKKSKIAAAILDAFSQNWRRKR, (SEQ ID NO: 17)

RKSKIEAEILDAFSQNWRRKR, (SEQ ID NO: 18)

AKIAAAILDAFSQNWRRKR, (SEQ ID NO: 19)

AKIEAAILDAFSQNWRRKR, (SEQ ID NO: 20)

LTLRKEPASEIAQSILEAYSQNGWANRRSGGKRPPPRRRQRRKKRG, (SEQ ID NO: 21)

RKKASSKIAAAILDAFSQNGWANRRSSCKRPPPRRRQRRKKRG, (SEQ ID NO: 22)

US 12,653,862 B2

5

-continued (SEQ ID NO: 23)
RKKASSKIAAAILDAFSQNAWANRRSSCKRPPPRRRQRRKKRA, (SEQ ID NO: 24)
RKKASSKIAAAILDAFSQNWRRKRPPRRRQRRKKRG, (SEQ ID NO: 25)
RKKASSKIEAAILDAFSQNWRRKRPPRRRQRRKKRG, (SEQ ID NO: 26)
RKKASSKIAAEILDAFSQNWRRKRPPRRRQRRKIKRG, (SEQ ID NO: 27)
RKKASSKIEAEILDAFSQNWRRKRPPRRRQRRKKRG, (SEQ ID NO: 28)
RKKSKIAAAILDAFSQNWRRKRRRRQRRKKRG, (SEQ ID NO: 29)
RKKSKIEAEILDAFSQNWRRKRRRRQRRKKRG, (SEQ ID NO: 30)
AKIAAAILDAFSQNWRRKRRRRQRRKKRG, (SEQ ID NO: 31)
AKIEAAILDAFSQNWRRKRRRRQRRKKRG, (SEQ ID NO: 53)
RKKASSKIEAEILDAFSQNWRRKRPPRRRQRRKKRG, (SEQ ID NO: 54)
RKKSKIEAEILDAFSQNWRKRRRRQRRKKRG, (SEQ ID NO: 55)
AKIEAAILDAFSQNWRKRRRRQRRKKRG, (SEQ ID NO: 56)
AKIEAEILDAFSQNWRKRRRRQRRKKRG, (SEQ ID NO: 57)
AKIEAAILDEFSQNWRKRRRRQRRKKRG, (SEQ ID NO: 58)
RKKASJKIAJAILDAFSQNWRRKRPPRRRQRRKKRG, (SEQ ID NO: 59)
RKKASSKIAAAZLDAFSQNAWANRRSSCKRPPPRRRQRRKKRA, (SEQ ID NO: 60)
AKIEAAILDAFSQNBRKRRRRQRRKKRG, (SEQ ID NO: 61)
AKIEAEILEAFSQNBRKRRRRQRRKKRG, (SEQ ID NO: 62)
AKIEAAZLDAFSQNBRKRRRRQRRKKRG, (SEQ ID NO: 63)
RKKASSKIEAEILDAFSQNBRRKRPPRRRQRRKKRG, (SEQ ID NO: 64)
RKKASSKIEAEZLDAFSQNBRRKRPPRRRQRRKKRG, (SEQ ID NO: 65)
RKKASSKIEAEIZDAFSQNBRRKRPPRRRQRRKKRG, (SEQ ID NO: 67)
RKKSKIAAAILDAFSQNWRKRRRRQRRKKRG,
and (SEQ ID NO: 68)
RKKASSKIEAAILDAFSQNWRRKRPPRRRQRRKKRG, wherein J, B, and Z are defined as above, and a peptide, in particular a peptide comprising an amino acid sequence selected from an amino acid sequence that is at least 80%, preferably at least 90%, more preferably at least 95% identical to any one of SEQ ID NO: 1 to 4, and 7 to 31, and 53 to 65, and 67 and 68, and a peptide consisting of the amino acid sequence according to any one of SEQ ID NO: 1 to 4, and 7 to 31, and 53 to 65, and 67 and 68, as well as pharmaceutically acceptable salts thereof. These peptides are particularly D-peptides.

In a second aspect thereof, the present invention relates to a method for identifying an improved compound that binds to p53 or preferably binds to p53 and inhibits the interaction of FOXO4 with p53 in a cell, comprising the steps of a) providing at least one compound according to the present invention as herein; b) suitably modifying said compound of a); c) determining at least one of binding of said at least one compound of b) p53 or a fragment thereof, the stability of said at least one compound, and binding of FOXO4 or said fragment thereof to p53 or said fragment thereof in the presence of said at least one compound, compared to binding of FOXO4 or said fragment thereof to p53 or said fragment thereof in the absence of said compound; and d) identifying an improved compound that binds to p53 or preferably binds to p53 and inhibits the interaction of FOXO4 with p53 in a cell based on said determining in step c) when compared to a compound as provided in step a).

Preferred is a method according to the present invention, wherein said binding of said at least one compound is specific for p53 or said fragment thereof. A preferred method further comprises the step of testing said compound as identified for its activity to induce apoptosis and/or to kill senescent cells, scarred cells, and/or tumor cells, preferably comprising determination of caspase activity.

In a third aspect thereof, the present invention relates to a screening tool for screening for a compound that binds to p53, and preferably binds to p53 and inhibits the interaction of FOXO4 with p53 in a cell, comprising an isolated cell expressing FOXO4, and/or a cell expressing a p53 binding fragment thereof, wherein said cell optionally expresses p53, and/or a cell expressing a FOXO4 binding fragment thereof.

Preferred is a screening tool according to the present invention, wherein said fragment of FOXO4 is a peptide according to the sequence PRKGGSRRNAWGNQ SYAEL-ISQAIESAPEKRLTLAQIYEWMVRTVPYFKDKGD SNS SAGWKNSIRHNLSLHSKFIKVHNEATGKSSWWMLN (the complete forkhead domain) (SEQ ID NO: 32) or PRKGGSRRNAWGNQSYAELISQAIESAPEKRLTL (SEQ ID NO: 33), and wherein said fragment of p53 is a peptide according to the sequence AMDDLMLSPD-DIEQWFTEDPGP (SEQ ID NO: 34).

In a fourth aspect thereof, the present invention relates to a method for manufacturing a pharmaceutical composition for treating or preventing senescent cells, scarred cell and/or cancer cells in a subject, comprising the steps of formulating the compound according to the present invention into a suitable pharmaceutical composition or performing a method according to the present invention, and formulating said compound as identified into a suitable pharmaceutical composition. A pharmaceutical composition according to the invention may comprise pharmaceutically acceptable excipients, e.g., without limitation, stabilizers, bulking agents, buffers, carriers, diluents, vehicles, solubilizers, and binders. The skilled person understands that the selection of appropriate excipients depends on the route of administration and the dosage form, as well as the active ingredient and other factors. A pharmaceutical composition according to the invention is preferably adapted for parenteral administration.

In a fifth aspect thereof, the present invention relates to a pharmaceutical composition for treating or preventing senescent cells, scarred cell and/or cancer cells in a subject, obtained by a method according to the present invention.

In a sixth aspect thereof, the present invention relates to at least one compound according to the present invention, or the pharmaceutical composition according to the present invention for use in medicine. Preferred is the at least one compound or the pharmaceutical composition for use according to the present invention, wherein said disease or condition to be prevented and/or treated is selected from a condition caused by senescent cells, scarred cells, age-related diseases, kidney disease, osteoarthritis, COPD, musculoskeletal diseases, impairment of cognitive functions, and cancer.

In a seventh aspect thereof, the present invention relates to a method for treating or preventing a disease or condition caused by senescent cells, scarred cells, and/or cancer cells, age-related diseases, kidney disease, osteoarthritis, COPD, musculoskeletal diseases, impairment of cognitive functions, or cancer in a subject in need thereof, comprising administering to said subject an effective amount of the least one compound according to the present invention, or the pharmaceutical composition according to the present invention.

Other aspects and advantages can be readily derived from reading the following description and the non-limiting examples.

In the context of the experiments as performed for the present invention, the inventors surprisingly found that still quite substantial functional improvements could be achieved when introducing changes into compound after a careful further analysis of the interactions of FOXO4 with p53.

Therefore, a primary aspect of the invention is directed at an improved compound that is selected from i) a peptide comprising an amino acid sequence that is at least 70%, preferably at least 80%, and more preferably at least 90%, most preferably more than 95% identical to the amino acid sequence (SEQ ID NO: 1)

$X_3X_2X_4X_5X_7X_5X_4X_4X_6X_{18}X_8X_3QNX_9X_8X_{10}X_{10}X_{11}X_{12}S*X_{13}X_{14}X_{11}X_{11},$ wherein S* can be S or is absent;

$X_2$ is absent or is selected from K, E, R, and H;

$X_3$ is absent or selected from A, J, and S;

$X_4$ is selected from I, Z, and L, wherein Z is Cyclo-Hexyl-Alanine;

$X_5$ is selected from A, G, S, E, and D;

$X_6$ is selected from E and D;

$X_7$ is selected from J, G, Q, A, S, and P;

$X_8$ is selected from B, W, Y, and F, wherein B is 2-Methyl-tryptophan;

$X_9$ is absent or is selected from A and G;

$X_{10}$ is absent or is selected from A and N;

$X_{11}$ is selected from R and K;

$X_{12}$ is absent or is selected from R;

$X_{13}$ is absent or is selected from G and S;

$X_{14}$ is absent or is selected from A and C; and $X_{18}$ is selected from A and E;

with the provisio that either none or two Js are present that form a staple;

ii) the peptide according to i) comprising non-natural amino acids, and/or D-amino acids, and preferably the peptide according to i) comprising at least 80%, preferably at least 90%, more preferably at least 95% or consisting of at least 80% preferably of at least 90%, and more preferably of at least 95% D-amino acids, and iii) a retro inverso peptide according to i) or ii), i.e. a peptide in which the amino acid sequence is reversed and placed in the D-instead of the L-isoform when compared to the native protein sequence, and pharmaceutically acceptable salts thereof; and wherein said compound induces apoptosis and/or cell death in senescent, scarred cells, and/or cancerous cells. Preferably, said compound consists of D-amino acids.

Preferred is a compound that binds to p53 or more preferably binds to p53 and inhibits the interaction of FOXO4 with p53 in a cell, as can be detected with assays according to the state of the art, and/or the assays as disclosed herein. These assays include NMR, where the ability of said peptide to bind to (a fragment of) TP53 is determined; a pull down assay where a (biotinylated version of) the peptide is bound to (streptavidin) beads. This is poured over a cell lysate containing TP53 and the fraction of TP53 that binds to the said peptide is investigated; and a FRET/HTRF assay where the ability of a peptide to perturb the interaction between (fragments of) TP53 and FOXO4 is assessed.

The evolutionary differences between FOXO1/3/6 and FOXO4 indicated that several amino acids can still be modified in order to create improved compounds showing the desired inhibiting activity.

FOXO4 evolutionarily differs from FOXO1/3 and 6, as well as FOXO orthologs in lower species, in several unique residues. The inventors never found FOXO1 or FOXO3 foci and also have no evidence for FOXO1 and 3 to be important in senescent cell viability. Therefore, it was analyzed whether these amino acids at least partially explain the potency of FOXO4-peptides in eliminating senescent cells. This was confirmed, D-Retro-Inverso peptides based on a similar domain as in FOXO4, but based on the sequence of FOXO1 or FOXO3 did not show selectivity in eliminating senescent cells.

An analysis of the FOXO4-FH fragment and the TP53-TAD2 domain showed that negative charges in TP53 mediate binding to FOXO4, as well as a hydrophobic Tyr. Therefore, a mutation to a positive amino acid, like Glu->Lys and Tyr->Phe was anticipated as beneficial for the strength of the interaction. The NMR also showed that the n-terminal amino acids LTL are not necessary for the interaction. Finally, the NMR showed that negatively charged amino acids in TP53 are responsible for the interaction with FOXO4 around the SQ motif (site). The NG amino acid site can be modified in order to improve stability of the molecules. All these modifications presented a new strategy where any one of these or a combination thereof lead to the rational design of improved molecules for use in the context of the present invention.

It was also found that the active peptides in the context of the present invention can be rather short when compared to the already existing proposals in the state of the art, while still maintaining a strong activity. Nevertheless, longer more active peptides are also possible, therefore, a preferred compound according to the invention is a peptide comprising an amino acid sequence that is at least 70%, preferably at least 80%, and more preferably at least 90% identical to the amino acid sequence (SEQ ID NO: 2)

$X_1X_{17}K*X_2X_{16}X_3X_3X_2X_4X_5X_7X_5X_4X_4X_6AX_8X_3QNX_9X_8X_{10}X_{10}X_{11}X_{12}S*X_{13}$ $X_{14}X_{11}X_{11}X_{15},$ wherein Z, B, J, S*, X$_2$, X$_3$, X$_4$, X$_5$, X$_6$, X$_7$, X$_8$, X$_9$, X$_{10}$, X$_{11}$, X$_{12}$, X$_{13}$, X$_{14}$, and X$_{18}$ are according to claim 1;

K* can be K or is absent;

X$_1$ is absent or indicates the amino acid sequence LTL;

X$_{15}$ is absent or is selected from A and C;

X$_{16}$ is selected from A, and P; and

X$_{17}$ is absent or is selected from R and S; and wherein said compound induces apoptosis in senescent, scarred cells, and/or cancerous cells It was furthermore found that particularly active peptides according to the present invention comprises certain amino acid motifs, and preferred is the amino acid motif X$_3$QNX$_9$X$_8$ (e.g. starting at position 18 of SEQ ID NO: 2) that is selected from SQNAW (SEQ ID NO: 43), SQNGW (SEQ ID NO: 44) and SQN-W (SEQ ID NO: 45), wherein "-" indicates an absent amino acid.

It was surprisingly found that in case of X$_9$ as alanine (A), the peptides showed improved stability in solution, as exemplified in case of the peptides SEQ ID NO: 12 and 23 (see examples). Therefore, this exchange is preferred in order to provide additional stability to a compound according to the present invention.

Even more preferably, the compound according to the present invention comprises the amino acid motif X$_2$X$_4$X$_5$X$_7$X$_5$ (e.g. starting at position 8 of SEQ ID NO: 2) that is selected from KIAAA (SEQ ID NO: 46), KIEAA (SEQ ID NO: 47), KIAAE (SEQ ID NO: 48) and KIEAE (SEQ ID NO: 49).

Still more preferably, the compound according to the present invention comprises the amino acid motif X$_4$X$_5$X$_7$X$_5$X$_4$X$_4$X$_6$AX$_8$X$_3$QNX$_9$X$_8$ (SEQ ID NO: 3, starting at position 9 of SEQ ID NO: 2) that is selected from the general formula (SEQ ID NO: 4)

IX$_5$X$_7$X$_5$ILX$_6$AFX$_3$QNX$_9$W, wherein

X$_3$ is absent or selected from A, J, and S;

X$_5$ is selected from A, G, S, E, and D;

X$_6$ is selected from E and D;

X$_7$ is selected from J, G, Q, A, S, and P; and

X$_9$ is absent or is selected from A and G.

In the context of the present invention, it was found that the amino acid motif LTLRKEASSE (SEQ ID NO: 35) is dispensable for the general improved functions of the peptides, and can be reduced to a single Ala, replaced by Ala, "neutral" or positively charged amino acids. In contrast, the "core motif" X$_4$X$_5$X$_7$X$_5$X$_4$X$_4$X$_6$AX$_8$X$_3$QNX$_9$X$_8$ (SEQ ID NO: 3, starting at position 9 of SEQ ID NO: 2) that can be selected from the general formula IX$_5$X$_7$X$_5$ILX$_6$AFX$_3$QNX$_9$W (SEQ ID NO: 4) as above is most important. Nevertheless, in this motif, the amino acids "SQNG" (SEQ ID NO: 50) seem to function as a structural linker, and functions to allow fold-back of the "W" into the hydrophobic core. Several residues can be deleted, a single or double "G" are sufficient, and when using AANG (SEQ ID NO: 51) or SQ-G or SQAG (SEQ ID NO: 52), the peptides still function. The W at the end is essential, and difficult to replace with natural AAs. The "I" at the beginning is essential, needs to be a hydrophobic amino acid, preferably I/L, but can be non-natural as well. In the part IX$_5$X$_7$X$_5$IL (SEQ ID NO: 36, e.g. IAQSIL, SEQ ID NO: 37), the spacing between "I"s needs to be 2-3 residues. Several changes are tolerated as long they do not destroy the helix or the hydrophobic core. Similarly, the "IL" at the end is essential, and needs to be a hydrophobic amino acid, preferably I/L, but can be non-natural as well. Furthermore, the spacing between the following "L" and "Y" preferably is two residues but a single amino insertion is tolerated. Again, changes are tolerated as long they do not destroy the helix or the hydrophobic core. The "Y" is essential, needs to be a hydrophobic amino acid, preferably F/Y, but can be non-natural as well. Similar to the N-terminal part as above, the motif ANRRSSCKRP (SEQ ID NO: 38) is dispensable for the general improved functions of the peptides, and can be reduced to at least 3 positively charged residues, although even but with less the peptide is still active.

Most preferably, the compound according to the present invention is a peptide comprising an amino acid sequence selected from (SEQ ID NO: 7)
LTLRKEASSEIAQSILDAYSQNGWANRRSSCKRP, (SEQ ID NO: 8)
LTLRKKASSKIAQSILDAFSQNGWANRRSSCKRP, (SEQ ID NO: 9)
LTLRKEPASEIAQSILEAYSQNGWANRRSGGKRP, (SEQ ID NO: 10)
RKKASSKIAQSILDAFSQNGWANRRSSCKRP, (SEQ ID NO: 11)
RKKASSKIAAAILDAFSQNGWANRRSSCKRP, (SEQ ID NO: 12)
RKKASSKIAAAILDAFSQNAWANRRSSCKRP, (SEQ ID NO: 13)
RKKASSKIAAAILDAFSQNWRRKR, (SEQ ID NO: 14)
RKKASSKIEAAILDAFSQNWRRKR, (SEQ ID NO: 15)
RKKASSKIAAEILDAFSQNWRRKR, (SEQ ID NO: 16)
RKKASSKIEAEILDAFSQNWRRKR, (SEQ ID NO: 17)
RKKSKIAAAILDAFSQNWRRKR, (SEQ ID NO: 18)
RKKSKIEAEILDAFSQNWRRKR, (SEQ ID NO: 19)
AKIAAAILDAFSQNWRRKR, (SEQ ID NO: 20)
AKIEAAILDAFSQNWRRKR, (SEQ ID NO: 21)
LTLRKEPASEIAQSILEAYSQNGWANRRSGGKRPPPPRRRQRRKKRG, (SEQ ID NO: 22)
RKKASSKIAAAILDAFSQNGWANRRSSCKRPPPRRRQRRKKRG, (SEQ ID NO: 23)
RKKASSKIAAAILDAFSQNAWANRRSSCKRPPPRRRQRRKKRA, (SEQ ID NO: 24)
RKKASSKIAAAILDAFSQNWRRKRPPRRRQRRKKRG, (SEQ ID NO: 25)
RKKASSKIEAAILDAFSQNWRRKRPPRRRQRRKKRG, (SEQ ID NO: 26)
RKKASSKIAAEILDAFSQNWRRKRPPRRRQRRKKRG, -continued (SEQ ID NO: 27)
RKKASSKIEAEILDAFSQNWRRKRPPRRRQRRKKRG, (SEQ ID NO: 28)
RKKSKIAAAILDAFSQNWRRKRRRRQRRKKRG, (SEQ ID NO: 29)
RKKSKIEAEILDAFSQNWRRKRRRRQRRKKRG, (SEQ ID NO: 30)
AKIAAAILDAFSQNWRRKRRRRQRRKKRG, (SEQ ID NO: 31)
AKIEAAILDAFSQNWRRKRRRRQRRKKRG, (SEQ ID NO: 53)
RKKASSKIEAEILDAFSQNWRRKRPPRRRQRRKKRG, (SEQ ID NO: 54)
RKKSKIEAEILDAFSQNWRKRRRRQRRKKRG, (SEQ ID NO: 55)
AKIEAAILDAFSQNWRKRRRRQRRKKRG, (SEQ ID NO: 56)
AKIEAEILDAFSQNWRKRRRRQRRKKRG, (SEQ ID NO: 57)
AKIEAAILDEFSQNWRKRRRRQRRKKRG, (SEQ ID NO: 58)
RKKASJKIAJAILDAFSQNWRRKRPPRRRQRRKKRG, (SEQ ID NO: 59)
RKKASSKIAAAZLDAFSQNAWANRRSSCKRPPPRRRQRRKKRA, (SEQ ID NO: 60)
AKIEAAILDAFSQNBRKRRRRQRRKKRG, (SEQ ID NO: 61)
AKIEAEILEAFSQNBRKRRRRQRRKKRG, (SEQ ID NO: 62)
AKIEAAZLDAFSQNBRKRRRRQRRKKRG, (SEQ ID NO: 63)
RKKASSKIEAEILDAFSQNBRKRPPRRRQRRKKRG, (SEQ ID NO: 64)
RKKASSKIEAEZLDAFSQNBRKRPPRRRQRRKKRG, (SEQ ID NO: 65)
RKKASSKIEAEIZDAFSQNBRKRPPRRRQRRKKRG, (SEQ ID NO: 67)
RKKSKIAAAILDAFSQNWRKRRRRQRRKKRG,
and (SEQ ID NO: 68)
RKKASSKIEAAILDAFSQNWRRKRPPRRRQRRKKRG, wherein J, B, and Z are defined as above, and a peptide comprising an amino acid sequence selected from an amino acid sequence that is at least 80%, preferably at least 90%, more preferably at least 95% identical to any one of SEQ ID NO: 1 to 4, and 7 to 31, and 53 to 65, and 67 and 68, and a peptide consisting of the amino acid sequence according to any one of SEQ ID NO: 1 to 4, and 7 to 31, and 53 to 65, and 67 and 68, preferably a peptide consisting of the amino acid sequence according to any one of SEQ ID NO: 55, 60, 63, 64, or 65, as well as pharmaceutically acceptable salts thereof.

In the compounds of the present invention, according to the single letter code for amino acids, $X_1$ is absent or indicates the amino acids LTL, since the N-terminal amino acids LTL are not necessary for the interaction. $X_2$ is selected from a positively charged amino acid, preferably, K, E, R, and H. $X_3$ is selected from a small non-polar amino acid, preferably, A, and S, and can form a staple using J as defined herein, $X_4$ is selected from a hydrophobic amino acid, preferably I and L, and a modified amino acid Z, wherein Z is cyclo-hexyl-alanine. $X_5$ is selected from a small positively or negatively charged amino acid, preferably A, G, S, E, and D. $X_6$ is selected from a negatively charged amino acid, preferably E and D. $X_7$ is selected from a small or polar amino acid, preferably G, Q, A, S, and P and can form a staple using J as defined herein. $X_8$ is selected from an aromatic amino acid, preferably W, Y, and F, and B, wherein B is 2-Me-tryptophane. $X_9$ is selected from a small polar or non-polar amino acid, preferably A and G. $X_{10}$ is selected from A and N and a charge neutral polar amino acid, preferably Q. $X_{11}$ and $X_{12}$ are selected from a positively charged amino acid, preferably R and K. $X_{13}$ is selected from G and S, $X_{14}$ and/or $X_{15}$ is selected from A and C, $X_{16}$ is selected from A and P, $X_{17}$ is selected from R and S, and $X_{18}$ is selected from A and E. Preferably, the compound may comprise non-naturally occurring amino acids that have the same or substantially the same desired properties of the natural amino acids as indicated here, and in the relevant position of said compound as indicated by the formulae herein. Also possible is the introduction of modified amino acids, such as, for example, linker amino acids, staples, cysteine bridges, glycolysation sites, ubiquitination and/or pegylation sites, as desired.

A stapled peptide is a short peptide, typically in an alpha-helical conformation, that is constrained by a synthetic brace ("staple"). The staple is formed by a covalent linkage between two amino acid side-chains, forming a peptide macrocycle. Staples thus in general refer to a covalent linkage of two previously independent entities. Among other applications, peptide stapling is notably used to enhance the pharmacologic performance of peptides.

Peptides of the present invention can be of any length, as long as the compound has the function of binding to p53, and/or binding to p53 and inhibiting or substantially inhibiting the interaction of FOXO4 with p53 in a cell. Preferred is a compound having a length of between 100 to 19, more preferred of between 75 to 19, even more preferred between 50 to 19 amino acids. Specifically preferred are peptides of the present invention having a length selected from the lengths as given in one of SEQ ID NO: 1 to 4, and 7 to 31, and 53 to 65, and 67 and 68.

The compound according to the present invention preferably is a retro inverso peptide comprising an amino acid sequence that is at least 80% identical, more preferably at least 90%, and most preferably at least 95% to any one of SEQ ID NO: 1 to 4, and 7 to 31, and 53 to 65, and 67 and 68.

The term "peptide", as used herein, preferably refers to synthetically synthesized peptides, preferably peptidomimetics, more preferably D-peptides. The term "peptide" encompasses peptide analogs, which may have, for example, modifications rendering the peptides more stable while in a body or more capable of penetrating into cells. Such modifications include, but are not limited to, N-terminal modification, C-terminal modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, and backbone modifications. Methods for preparing peptidomimetic compounds are well known in the art and are disclosed, for example, in Quantitative Drug Design, C. A. Ramsden Gd., Chapter 17.2, F. Choplin Pergamon Press (1992).

Further preferred modifications relate to the amino acids themselves, and comprise the introduction of non-naturally occurring amino acids, preferably having the same or substantially the same desired properties of the natural amino acids, preferably in the same or substantially the same position of said compound. Preferred examples are 2-Me-tryptophane or cyclo-hexyl alanine. Further modifications can include modified amino acids, such as, for example, linker amino acids, staples, cysteine bridges, glycolysation sites, ubiquitination and/or pegylation sites. Stapling can be accomplished by introduction of two a-pentenylglycine residues, or a,a'-pentenylalanine residues for cross-linking the i and i+4 or i and i+7 residues within the peptide. These residues are used to create an all-hydrocarbon, alkene-containing, des-methyl constraint or staple. Preferred is Fmoc-L-2-(4'-pentenyl)alanine and ring-closing metathesis (RCM) (see, for example, Kim Y W, Kutchukian P S, Verdine G L. Introduction of all-hydrocarbon i,i+3 staples into alpha-helices via ring-closing olefin metathesis. Org Lett. 2010 Jul. 2; 12(13):3046-9. doi: 10.1021/o11010449). Other strategies that may be used to cross-link or constrain the peptide include lactam bridges, hydrogen-bond surrogates, photoswitches, thioethers, and triazoles introduced by "click" chemistry.

In one preferred embodiment, the compound according to the present invention further comprises a peptide sequence conferring cell-penetrating properties, organelle targeting properties, nuclear localization, mitochondrial localization, blood brain barrier permeability, cell membrane localization, and/or peptidase cleavage. A cell-penetrating sequence is, for example, the TAT-sequence of HIV (GRKKRRQRRRPP, SEQ ID NO: 41) or ARKKRRQRRRPPP (SEQ ID NO: 66). Suitable other sequences are known from the literature, and can be taken from, for example, the reference of Ramaker et al. (Ramaker et al. (2018) Cell penetrating peptides: a comparative transport analysis for 474 sequence motifs, Drug Delivery, 25:1, 928-937). For nuclear localization, see, for example, Kim Y H, Han M E, Oh S O. The molecular mechanism for nuclear transport and its application. Anat Cell Biol. 2017; 50(2): 77-85. doi:10.5115/acb.2017.50.2.77). Said peptide sequence can be preferably fused to the N- and/or C-terminal part of said peptide.

The term "D-isoform", as used herein, refers to an amino acid sequence in which at least part of the amino acid residues have the molecular spatial configuration referred to as "D" (Latin dexter; right). The compounds of the present invention comprise at least 80%, more preferably at least 90%, more preferably at least 95%, and most preferably 99% or 100% (i.e. "all-D") D-amino acids. A peptide of the invention preferably contains at least 19, 20, 21, 22, 23, 24, 25, 26, 27, 28, 29, 30, 31, 32, 33, 34, 35, 36, 37, 38, 39, 40, or more D-amino acid residues. Also, a peptide of the invention preferably contains at least 80%, more preferably at least 85%, even more preferably at least 90, 95, 98 or 99%, most preferably 100% D-amino acid residues.

The abbreviation "DRI", as used herein, refers to the D-retro-inverso isoform, in which the amino acid sequence is reversed and placed in the D-instead of the L-isoform, in particular with reference to the sequences of the human FOXO4 protein, or a peptide fragment thereof. The skilled person will appreciate that a DRI peptide according to the invention may contain a combination of L-amino acid residues and D-amino acid residues, or may consist entirely of D-amino acid (all-D) residues, e.g. as disclosed above. The terms "% sequence identity" or "% identical sequence" are defined herein as the percentage of nucleotides in a nucleic acid sequence, or amino acids in an amino acid sequence, that is identical with the nucleotides, resp. amino acids, in a nucleic acid or amino acid sequence of interest, after aligning the sequences and optionally introducing gaps, if necessary, to achieve the maximum percent sequence identity. Methods and computer programs for alignments are well known in the art. Sequence identity is calculated over substantially the whole length, preferably the whole (full) length, of an amino acid sequence of interest. The skilled person understands that consecutive amino acid residues in one amino acid sequence are compared to consecutive amino acid residues in another amino acid sequence. Preferably, the configuration of an amino acid residue, for example D or L, is not relevant for determining amino acid sequence identity. For example, a D-Ala (D-A) exhibits sequence identity to an L-Ala (L-A) in the context of the invention.

The skilled person is furthermore aware of the existence of in vitro standard assays for determining the extent of apoptosis in a cell and/or cell culture, for example tests that assess levels of cytoplasmic Cytochrome C (marker for apoptosis) and levels of TUNEL (marker for apoptosis). Using these standard assays, the skilled person can easily assess and compare the apoptosis-inducing activity of different compounds with regard to different cell type or cells in a different developmental stage, e.g. senescent vs. non-senescent cells. Other standard apoptosis assays are an Annexin V assay and a cleaved caspase-3 staining. To detect cell viability, which is essentially the opposite of apoptosis, an MTT assay (colorimetric assay for assessing cell viability), an ATP-detection assay, a real-time cell density (for instance xCELLigence) assay or a colony formation assay can be used. Additional information about assays to be used can be taken from the literature, for example from Elmore S. Apoptosis: a review of programmed cell death. Toxicol Pathol. 2007; 35(4):495-516. The assays preferably comprise determination of elevated caspase-3/7 activity, loss of mitochondrial cytochrome C, TUNEL positivity, extracellular annexin-V positivity, and/or and elevation in cell death markers, such as cellular propidium iodide inclusion, and or loss of viability, such as loss of incorporation of calcein-AM or an MTS viability assay.

Usually and preferably, senescent cells can be identified as cells with a reduced presence/staining of the markers LMNB1 and/or HMGB1, and an elevation in p21$^{cip1}$ and/or p16$^{INK4a}$, and/or presence of DNA-SCARS markers yH2AX and/or 53BP1 and/or PML., and/or a presence of markers of the SASP as IL1 and/or IL6 and/or MMP1. The cells also need not to show a full absence of TP53 or mutants thereof. Usually and preferably, cancer cells can be identified as cells with an elevation in p21$^{cip1}$, and/or a presence of DNA-SCARS markers yH2AX and/or 53BP1 and/or PM, and/or a presence of markers of the SASP as IL1 and/or IL6 and/or MMP1. The cells also need not to show a full absence of TP53 or mutants thereof. Usually and preferably, scarred cells can be identified as cells with an elevated level of DNA-SCARS: larger clusters of 53BP1 and/or yH2AX, and/or PML/FOXO4 nuclear bodies.

In another aspect, the invention provides a nucleic acid encoding a peptide according to the invention (to the extent as biologically possible, optionally comprised in a vector, such as an expression vector. The nucleic acid can be DNA, RNA, cDNA, PNA or a combination thereof. In a further aspect, the invention provides a host cell comprising a nucleic acid or vector according to the invention. The host cell can be any kind of suitable pro- or eukaryotic cell, such as, for example, selected from the group of cancer cells, senescent cells, scarred cells human non-embryonic stem cells, yeast cells, bacterial cells, and recombinant host cells expressing FOXO4 and/or the p53 binding fragment thereof, and recombinant host cells optionally expressing p53 and/or the FOXO4 binding fragment thereof.

As also mentioned above, the present invention relates to improved inhibiting compounds that were designed because the evolutionary differences between FOXO1/3/6 and FOXO4 indicated that several amino acids can still be changed or modified in order to create improved inhibiting compounds. All these modifications presented a new strategy wherein any one of these or a combination thereof finally lead to the "rational design" of improved molecules for use in the context of the present invention. The present invention also includes strategies in order to further improve compounds that have only partially undergone "directed evolution" or "directed mutagenesis".

Another important aspect of the present invention is therefore a method for identifying an improved compound that binds to p53 or preferably binds to p53 and inhibits the interaction of FOXO4 with p53 in a cell, comprising the steps of a) providing at least one compound according to the present invention; b) suitably modifying said compound of a); c) determining at least one of binding of said at least one compound of b) p53 or a fragment thereof, the stability of said at least one compound, and binding of FOXO4 or said fragment thereof to p53 or said fragment thereof in the presence of said at least one compound, compared to binding of FOXO4 or said fragment thereof to p53 or said fragment thereof in the absence of said compound; and d) identifying an improved compound that binds to p53 or preferably binds to p53 and inhibits the interaction of FOXO4 with p53 in a cell based on said determining in step c) when compared to a compound as provided in step a).

Preferred is the method according to the present invention, wherein said binding of said at least one compound is specific and/or is determined/detected as being specific for p53 or said fragment thereof.

Further preferred is the method according to the present invention that further comprises testing of said compound as identified for its activity to induce apoptosis and/or to kill senescent, scarred or cancer or tumor cells, preferably comprising determining a caspase activity.

In the course of the "rational design" of improved molecules for use in the context of the present invention, and in order to further improve compounds that have only partially undergone "directed evolution" or "directed mutagenesis", the compounds can undergo several successive rounds of the above methods.

Following the provision of a compound (e.g. a peptide), for example after suitable chemical synthesis thereof, the compound can be modified. In general, many methods of how to modify compounds of the present invention are known to the person of skill, and are disclosed in the literature. Modifications of the compounds will usually fall into several categories, for example a) mutations/changes of amino acids into different amino acids, b) chemical modifications of amino acids, e.g. through the addition of additional chemical groups, c) modifications of the amino acid structure (e.g. L-into D-form) or bonds (e.g. introduction of retro-inverso bonds), d) changes of the length of the compound, and e) the attachment of additional groups to the molecule (including marker groups, labels, linkers or carriers, such as chelators).

The evolutionary differences between FOXO1/3/6 and FOXO4 indicate that several amino acids can still be modified in order to create improved compounds showing the desired binding and—ultimately— also inhibiting activity. An analysis of the FOXO4-FH fragment and the TP53-TAD2 domain showed that negative charges in TP53 mediate binding to FOXO4, as well as a hydrophobic Tyr. Therefore, amino acids of the peptides according to the present invention can be mutated into positive amino acids, as beneficial for the strength of the interaction. Examples are lysine (K), arginine (R), and histidine (H). The NMR experiments also showed that negatively charged amino acids in TP53 are responsible for the interaction with FOXO4 around the SQ motif (site). This site can become phosphorylated, and to prevent this, the site can be mutated to a small amino acid, like alanine (A), glycine (G) or serine (S). Methods for introducing such mutations are known to the person of skill, and include the introduction of changes during chemical synthesis of the peptide, or genetic methods whereby the peptide encoding nucleotide sequence is altered accordingly, e.g. by oligonucleotide-based mutagenesis, mutagenesis comprising PCR, or the like. Also a random mutagenesis is possible. Further guidance with respect to prospective amino acid changes are found above in the context of the definitions with respect to $X_1$ to $X_{12}$, which are also readily applicable to the rest of the definitions $X_{13}$ to $X_{18}$.

Furthermore, amino acids can be altered by chemical modifications, e.g. through the addition of additional chemical groups during synthesis or via post-translational or post— synthesis modifications. Methods to modify amino acids are well known in the state of the art, and summarized, for example, in Christopher D. Spicer & Benjamin G. Davis. Selective chemical protein modification Nature Communications volume 5, Article no.: 4740 (2014); or Sakamoto S, Hamachi I. Recent Progress in Chemical Modification of Proteins. Anal Sci. 2019 Jan. 10; 35(1):5-27.

Also, modifications of the amino acid structure (e.g. L-into D-form) or the bonds between the amino acids (e.g. introduction of retro-inverso bonds during synthesis) can be performed. The NMR also showed that the three N-terminal amino acids LTL are not necessary for the interaction. Therefore, the length of the compound can be modified, e.g. by removing these three amino acids.

Finally, additional chemical and/or functional groups to the molecule, such as, for example, marker groups, labels, linker amino acids, staples, cysteine bridges, glycolysation sites, ubiquitination and/or pegylation sites, linkers or carriers, such as chelators. Also, the introduction or addition of amino acids that allow to make FOXO4-derived DRI peptide dimers or multimers (staples) is included. Furthermore, stabilizing modifications in order to enhance stability and/or the potency of FOXO4-derived DRI peptides to eliminate senescent cells can be included (e.g. so-called end capping). Stabilization of said FOXO4 peptides may also be achieved by mutating site(s) at which the peptide usually break down, e.g. the NG-site. Stapling can be accomplished by introduction of two a-pentenylglycine residues, or a,a'-pentenylalanine residues for cross-linking the i and i+4 or i and i+7 residues within the peptide. These residues are used to create an all-hydrocarbon, alkene-containing, des-methyl constraint or staple. Other strategies that may be used to cross-link or constrain the peptide include lactam bridges, hydrogen-bond surrogates, photoswitches, thioethers, and triazoles introduced by "click" chemistry.

In a next step, the modified compound is tested for at least one of binding of said at least one compound to p53 or a fragment thereof. As discussed herein, the property of the compound to bind to p53 or a binding fragment thereof (like TP53) is essential for all uses of the compound, be they therapeutic or diagnostic. In the context of the present invention, an "improved" binding comprises both scenarios where the modified compound binds to the same extent as the unmodified (i.e. starting) compound, although the compound has been modified (e.g. by dimerization or by adding markers or other groups). Preferred is a compound as modified that exhibits a stronger binding to the target, i.e. p53 or a binding fragment thereof. Also preferred is a compound that shows a longer binding to the target, i.e. p53 or a binding fragment thereof, for example because of an improved stability of said modified compound in vitro or in vivo. Further preferred is a compound that shows a reduced phosphorylation of said modified compound. Also included is a combination of at least two of these properties.

Assays to detect binding of the compound to the target (i.e. p53 and/or a binding fragment thereof) are well known to the person of skill and preferably include mass spectrometry, NMR assays, pull-down assays, or the like.

Furthermore included are competitive assays, i.e. tests for the properties of said modified compound in the presence of said at least one compound, compared to binding of FOXO4 or said fragment thereof to p53 or said fragment thereof in the absence of said compound.

Further preferred is a method according to the present invention, wherein said binding of said at least one compound is specific and/or is determined/detected as being specific for p53 or said fragment thereof. As mentioned above, the property of the compound to bind to p53 or a binding fragment thereof (for example TP53) is essential for all uses of the compound, be they therapeutic or diagnostic. Ideally, the binding is also specific or at least substantially or essentially specific for the intended target, i.e. p53 or a binding fragment thereof. This will reduce or avoid any unwanted side effects in the medical use of the compound and reduce or avoid any background or false positive results in a diagnostic use.

In the last step of the method, an improved compound is identified that—in the preferred aspect of the present invention—binds to p53 or preferably binds to p53 and inhibits the interaction of FOXO4 with p53 in a cell based on said determining in step c) when compared to a compound as provided in step a). While this function is deemed essential for the therapeutic function of the compounds according to the present invention by eliminating senescent cells, improved diagnostic molecules according to the present invention may not mandatorily require such property/function.

The identification of such improved compounds may include to detect the potency of these compounds, such as FOXO4-peptides, to bind TP53 and eliminate senescent cells, and optionally the identification of structural requirements that determine this property; and/or to detect the selectivity of these compounds, such as FOXO4-peptides, to eliminate senescent cells, and again optionally the identification of structural requirements that determine this property. FOXO4 evolutionarily differs from FOXO1/3 and 6, as well as FOXO orthologs in lower species, in several unique residues. The inventors never found FOXO1 or FOXO3 foci and also have no evidence for FOXO1 and 3 to be important in senescent cell viability. Therefore, it was analyzed whether these amino acids at least partially explain the potency of FOXO4-peptides in eliminating senescent cells. This was confirmed, D-Retro-Inverso peptides based on a similar domain as in FOXO4, but based on the sequence of FOXO1 or FOXO3 did not show selectivity in eliminating senescent cells.

Further preferred is the method according to the present invention wherein said method further comprises testing of said compound as identified for its activity to induce apoptosis and/or to kill senescent, scarred, cancer or tumor cells, preferably comprising determining a caspase activity. As already mentioned above, the skilled person is furthermore aware of the existence of in vitro standard assays for determining the extent of apoptosis in a cell culture, for example tests that assess levels of cytoplasmic Cytochrome C (marker for apoptosis) and levels of TUNEL (marker for apoptosis). Using these standard assays, the skilled person can easily assess and compare the apoptosis-inducing activity of different compounds with regard to different cell type or cells in a different developmental stage, e.g. senescent vs. non-senescent cells. Other standard apoptosis assays are an Annexin V assay and a cleaved caspase-3 staining. The assays preferably comprise determination of elevated caspase-3/7 activity, loss of mitochondrial cytochrome C, TUNEL positivity, extracellular annexin-V positivity, and/or and elevation in cell death markers, such as cellular propidium iodide inclusion, and or loss of viability, such as loss of incorporation of calcein-AM or an MTS viability assay. To detect cell viability, which is essentially the opposite of apoptosis, an MTT assay (colorimetric assay for assessing cell viability), an ATP-detection assay, a real-time cell density (for instance xCELLigence) assay or a colony formation assay can be used. Additional information about assays to be used can be taken from the literature, for example from Elmore S. Apoptosis: a review of programmed cell death. Toxicol Pathol. 2007; 35(4):495-516. Preferably, a peptide or improved peptide according to the invention is considered to exhibit apoptosis-inducing activity in senescent cells if it kills, clears, removes or reduces the viability of at least 5, 10, 15, 20, 25, 30, 40, 50, 60, 70 or 80% of the cells in a senescent cell culture. Preferably, a peptide according to the invention selectively exhibits apoptosis-inducing activity in senescent cells, i.e. not in non-senescent cells. A peptide according to the invention favors apoptosis in senescent cells over apoptosis in non-senescent cells by at least a factor 1.1, 1.2, 1.3, 1.4, 1.5, 1.6, 1.7, 1.8, 1.9, 2.0, 2.5, 3, 4, 5 or higher.

A peptide according to the invention is preferably isolated. A peptide according to the invention is preferably produced using suitable peptide synthesis.

In one aspect of the method according to the present invention said FOXO4 or the p53 binding fragment thereof, p53 or the FOXO4 binding fragment thereof, and/or the compound (peptide) is/are labeled, for example with a fluorescent, detectable, stable isotope and/or a mass label. Such labels are known in the literature, and include FITC, Alexa, Dylight, FAM and others. Detectable labels may be recognized by antibodies, streptavidin/avidin, or are based on enzymatic reactions leading to detectable products. Mass labeling can be achieved by attaching isotopes, or other suitable mass markers. In principle any label which may be used for experimental and therapeutic/imaging purposes may be used as well.

Further preferred is the method according to the present invention, wherein said FOXO4 or said fragment thereof, and/or to p53 or said fragment thereof is recombinantly expressed in a cell. Methods for recombinantly expressing peptides as well as isolating and purifying said recombinantly produced products are well known in the art, and described in the respective literature. In general, any suitable cell can be used for recombinantly producing said FOXO4 or said fragment thereof, and/or to p53 or said fragment thereof, preferred is a cell that is selected from the group of cancer cells, senescent cells, human non-embryonic stem cells, yeast cells, bacterial cells, recombinant host cells expressing FOXO4 or the p53 binding fragment thereof, and wherein said recombinant host cells optionally express p53 or the FOXO4 binding fragment thereof, i.e. both or several of the constructs to be used.

Yet another aspect of the present invention then relates to a screening tool for screening for a compound according to the present invention that binds to p53, and preferably binds to p53 and inhibits the interaction of FOXO4 with p53 in a cell, comprising an isolated cell expressing FOXO4, and/or a cell expressing a p53 binding fragment thereof, wherein said cell optionally expresses p53, and/or a cell expressing a FOXO4 binding fragment thereof.

The screening tool of the present invention is an important part in order to perform a method according to the present invention, and can also be used as a first step to validate the pharmaceutical activity of the compounds in vivo. Preferably, said FOXO4 or said fragment thereof, and/or to p53 or said fragment thereof is recombinantly expressed in said cell. Methods for recombinantly expressing peptides as well as isolating and purifying said recombinantly produced products are well known in the art, and described in the respective literature. In general, any suitable cell can be used for recombinantly producing said FOXO4 or said fragment thereof, and/or to p53 or said fragment thereof, preferred is a cell that is selected from the group of cancer cells, scarred cells, senescent cells, human non-embryonic stem cells, yeast cells, bacterial cells, recombinant host cells expressing FOXO4 or the p53 binding fragment thereof, and wherein said recombinant host cells optionally express p53 or the FOXO4 binding fragment thereof, i.e. both or several of the constructs to be used. In one aspect of the tool according to the present invention said FOXO4 or the p53 binding fragment thereof, p53 or the FOXO4 binding fragment thereof, and/or the compound (peptide) is/are labeled, for example with a fluorescent, detectable, and/or a mass label. As mentioned above, such labels are known in the literature, and include FITC, Alexa, Dylight, FAM and others. Detectable labels may be recognized by antibodies, streptavidin/avidin, or are based on enzymatic reactions leading to detectable products. Mass labeling can be achieved by attaching isotopes, or other suitable mass markers.

Preferred is a screening tool according to the present invention comprising a fragment of FOXO4 as a peptide according to the sequence RKK PRKGGSRRNAWGNQ SYAELISQAIESAPEKRLTLAQIYEWMVRTVP-YFKDKGD SNSSAGWKNSIRHNLSLHSKFIKVH-NEATGKSSWWMLN (SEQ ID NO: 32) or PRKGGSRR-NAWGNQSYAELISQAIESAPEKRLTL (SEQ IFD NO: 33) preferably an all D-peptide, and a fragment of p53 as a peptide according to the sequence (SEQ ID NO: 34)
AMDDLMLSPDDIEQWFTEDPGP.

Yet another important aspect of the present invention then relates to the use of the compounds according to the present invention in diagnosis, e.g. as a diagnostic compound. Obviously, the compounds according to the present invention are identified/used in order to bind to p53 or a fragment of p53, and preferably to furthermore inhibit the interaction of FOXO4 with p53 in a cell. These properties are also used in a diagnostic context. More preferably the binding of said at least one compound is specific and/or is determined/detected as being specific for p53 or a fragment of p53 or said fragment thereof. This will reduce or avoid any background or false positive results in a diagnostic use. The compounds according to the present invention (peptide) is/are preferably labeled, for example with a fluorescent, detectable, and/or a mass label. As mentioned above, such labels are known in the literature, and include FITC, Alexa, Dylight, FAM and others. Detectable labels may be recognized by antibodies, streptavidin/avidin, or are based on enzymatic reactions leading to detectable products. Mass labeling can be achieved by attaching isotopes, or other suitable mass markers. Nevertheless, a diagnostic method can also be performed without labels, and the binding can be detected directly or indirectly using, for example, NMR.

One specific diagnostic use or method would be a method for detecting the expression p53 or a fragment thereof in a cell, comprising detecting p53 or said fragment thereof using a compound according to the present invention, wherein an increased binding compared to a control cell not expressing p53 or said fragment thereof indicates the expression of p53 or said fragment thereof in said cell. Because of the high specificity of the compound according to the present invention, the compounds provide improved molecules for diagnosis. The diagnosis may further comprise detecting a p53-related disease or condition, such as cancer or other conditions caused by condition caused by senescent cells, such as age-related diseases, kidney disease, non-alcoholic steohepatitis (NASH)/non-alcoholic fatty liver diseases (NAFLD), Liver fibrosis, idopathic iulmonary ibrosis (IPF), amyotrofic lateral sclerosis (ALS), osteoarthritis, COPD, musculoskeletal diseases, and reductions of cognitive functions.

In the context of the present invention, the term "about" shall mean to include+/−20%, preferably +/−10% of the amount as given, unless otherwise noted.

Preferably, the methods according to the present invention are amenable to automation, and are preferably performed in an automated and/or high-throughput format. Usually, this involves the use of chips and respective machinery, such as robots. Automation is particularly preferred in case of the identification of improved compounds and/or screening. Also, the use of the screening tool of the present invention can be included in automation as well.

Yet another important aspect of the present invention then relates to a method for manufacturing a pharmaceutical composition for treating or preventing senescent cells in a subject, comprising the steps of formulating the compound according to the present invention into a suitable pharmaceutical composition, or performing a method according to the present invention for identifying an improved compound that preferably inhibits the interaction of FOXO4 with p53 in a cell, and formulating said compound as identified into a suitable pharmaceutical composition. The invention also relates to a pharmaceutical composition for treating or preventing senescent cells in a subject, obtained by said method according to the present invention.

The term "pharmaceutical composition", as used herein, refers to a composition that is made under conditions such that it is suitable for administration to mammals, preferably humans, e.g., it is made under GMP conditions. A pharmaceutical composition according to the invention may comprise pharmaceutically acceptable excipients, e.g., without limitation, stabilizers, bulking agents, buffers, carriers, diluents, vehicles, solubilizers, and binders. The skilled person understands that the selection of appropriate excipients depends on the route of administration and the dosage form, as well as the active ingredient and other factors. A pharmaceutical composition according to the invention is preferably adapted for parenteral administration.

Preferred is a pharmaceutical composition according to the present invention, comprising a mixture of compounds and/or a mixture of at least one of said compounds with an additional pharmaceutically active ingredient. The term "pharmaceutically active agent", as used herein, refers to a compound that inhibits or prevents the viability and/or function of cells, and/or causes destruction of cells (cell death), and/or exerts anti-tumor/anti-proliferative effects, for example, prevents directly or indirectly the development, maturation or spread of tumor cells. The term also includes agents that cause a cytostatic effect only and not a mere cytotoxic effect. The term also includes alkylating agents such as platinum drugs (e.g. cisplatin, carboplatin, and oxalaplatin), antimetabolites such as 5-fluorouracil (5-FU), 6-mercaptopurine (6-MP), capecitabine (Xeloda), cladribine, clofarabine, cytarabine (Ara-C), floxuridine, fludarabine, gemcitabine (Gemzar), hydroxyurea and methotrexate, anti-tumor antibiotics, preferably Doxorubicin, topoisomerase inhibitors, mitotic inhibitors, corticosteroids, anti-angiogenic agents, tyrosine kinase inhibitors, protein kinase A inhibitors, members of the cytokine family, radioactive isotopes. Also included as chemotherapeutic agents in the context of this invention are Taxanes such as Paclitaxel or Doxetaxel.

In another aspect, the invention provides the at least one peptide, the pharmaceutical composition, or nucleic acid according to the invention for use in medicine or for use as a medicament, or for use in the treatment of condition or a disease or disorder.

The term "diseases or conditions caused by senescent cells, scarred cells, and/or cancer cells", as used herein, refers to any disease or condition in a mammalian, preferably human, subject wherein the presence of senescent cells, or presence of cellular senescence, in a mammalian, preferably human, subject is linked to said disease or condition in said subject.

Normal and pathological degenerative aging phenotypes (loss-of-function) and cancer (gain-of-function) are established as causally linked to cellular senescence. Senescent fibroblast have been implicated in decreased milk-production in breast, senescent pulmonary artery smooth muscle cells are implicated in pulmonary hypertension, senescent skin cells are related to epidermal thinning and reduced collagen content, senescent astrocytes are implicated in Alzheimers and Parkinson's disease and senescent chondrocytes have been brought in connection with osteoarthritis.

The conditions and diseases that have been brought into connection with cellular senescence further comprise: Atherosclerosis, lung emphysema, diabetic ulcers, renal disease (see, for example, Valentijn F A, et al. Cellular senescence in the aging and diseased kidney. J Cell Commun Signal. 2018 March; 12(1): 69-82), kyphosis, osteoporosis, macular degeneration, COPD and insulin resistance, diabetes, obesity, laminopaties such as Hutchinson Gilford's progeria, hernia, sarcopenia and cachexia, arthritis, scoliosis, and cancer. Thus, clearance of senescent cells in a genetic fashion markedly improves the fitness and decrease parameters of aging, as shown in a mouse model for accelerated aging (Baker et al., 2011. Nature 479(7372):232-6). This proof-of-concept evidence was actually obtained in a genetic fashion that has poor therapeutic applicability. The present invention provides new improved compounds and methods for identifying them that therapeutically target senescent cells and that can be used in the treatment of diseases associated with cellular senescence.

Another aspect relates to the at least one compound or the pharmaceutical composition for use in the prevention or treatment according to the present invention, wherein said condition to be prevented and/or treated is selected from a condition caused by senescent cells, age-related diseases, kidney disease, non-alcoholic steohepatitis (NASH)/non-alcoholic fatty liver diseases (NAFLD), Liver fibrosis, idopathic iulmonary ibrosis (IPF), amyotrofic lateral sclerosis (ALS), arthritis, like osteoarthritis, COPD, musculoskeletal diseases, impairment of cognitive functions, atherosclerosis, lung emphysema, diabetic ulcers, kyphosis, osteoporosis, macular degeneration, COPD and insulin resistance, diabetes, obesity, laminopaties such as Hutchinson Gilford's progeria, hernia, sarcopenia and cachexia, scoliosis, and cancer.

Preferred is the at least one compound or the pharmaceutical composition for use according to the present invention, wherein said therapy is a combination therapy with anti-cancer chemotherapeutic agents or other standard of care drugs for the respective disease or condition or wherein said therapy is applied in senescent cells, scarred cells, and/or cancer cells that have been pretreated with anti-cancer chemotherapeutic agents or other standard of care drugs for the respective disease or condition, and have survived said treatment.

Consequently, another aspect relates to a method for treating or preventing a disease or condition caused by senescent cells, scarred cells, age-related diseases, kidney disease, non-alcoholic steohepatitis (NASH)/non-alcoholic fatty liver diseases (NAFLD), Liver fibrosis, idopathic iulmonary ibrosis (IPF), amyotrofic lateral sclerosis (ALS), arthritis, like osteoarthritis, COPD, musculoskeletal diseases, reductions of cognitive functions, atherosclerosis, lung emphysema, diabetic ulcers, kyphosis, osteoporosis, macular degeneration, COPD and insulin resistance, diabetes, obesity, laminopaties such as Hutchinson Gilford's progeria, hernia, sarcopenia and cachexia, scoliosis, and cancer in a subject in need thereof, comprising administering to said subject an effective amount of the least one compound according to the present invention, or the pharmaceutical composition according to the present invention.

Preferred is the method according to the present invention, wherein said therapy is a combination therapy with anti-cancer chemotherapeutic agents or other standard of care drugs for the respective disease or condition or wherein said therapy is applied in senescent cells, scarred cells, and/or cancer cells that have been pretreated with anti-cancer chemotherapeutic agents or other standard of care drugs for the respective disease or condition, and have survived said treatment.

"Treatment" shall mean a reduction and/or amelioration of the symptoms of the disease. An effective treatment achieves, for example, removal of senescent cells, a shrinking of the mass of a tumor and the number of cancer cells. A treatment can also avoid (prevent) and reduce the number of senescent cells, reduce the spread of the cancer, such as, for example, affect metastases and/or the formation thereof. A treatment may be a naive treatment (before any other treatment of a disease had started), or a treatment after the first round of treatment (e.g. after surgery or after a relapse). The treatment can also be a combined treatment, involving, for example, chemotherapy, surgery, and/or radiation treatment. A subject suffering, or suspected to suffer, from a disease or condition wherein the removal of senescent cells is beneficial can be treated, in particular a human.

In the context of the present invention it was surprisingly found that the compounds according to the present invention can be advantageously used and are most effective in particular in the case of therapy resistant cancers, as exemplified in the present examples and figures. In addition to being effective, it was also shown that the compounds of the present invention are not only cytostatic, but indeed cytotoxic to cancerous cells. The peptides are most effective in cells that have been pretreated with damaging agents as chemo-radiotherapy, and survived said treatment. Treatment using the peptides can thus be performed after/subsequent to a cell damaging first therapy, such as chemo-/radiotherapy, dietary stress, exogenous stress, oxidative stress etc., or as above, but as a combination therapy—i.e. applied together or to act together and not sequential. This is efficient for instance with small molecule inhibitors, such as BRAF inhibitors.

The invention further relates to a kit comprising a first container containing a compound according to the invention and a second container containing a chemotherapeutic agent. The kit may suitably contain instructions regarding the administration in a mammalian, preferably human, subject. The human subject is preferably suffering, or suspected to suffer, from a disease or condition caused by senescent cells, scarred cells, age-related diseases, kidney disease, non-alcoholic steohepatitis (NASH)/non-alcoholic fatty liver diseases (NAFLD), Liver fibrosis, idopathic iulmonary ibrosis (IPF), amyotrofic lateral sclerosis (ALS), arthritis, like osteoarthritis, COPD, musculoskeletal diseases, reductions of cognitive functions, atherosclerosis, lung emphysema, diabetic ulcers, kyphosis, osteoporosis, macular degeneration, COPD and insulin resistance, diabetes, obesity, laminopaties such as Hutchinson Gilford's progeria, hernia, sarcopenia and cachexia, scoliosis, and cancer. Although a compound of the invention and a chemotherapeutic agent can be formulated in a single dosage form, e.g. a pharmaceutical composition, it is preferably formulated in a multiple dosage form, wherein a compound of the invention is in one container and a chemotherapeutic agent is in another container. In a kit for use according to the invention, a compound of the invention and a chemotherapeutic agent are preferably co-administered. Preferably, said peptide is for administration after or following administration of said chemotherapeutic agent. Preferably, a compound of the invention is administered as adjuvant in such a way that in can clear, kill or reduce the viability of cells that have become senescent as a result of treatment with a chemotherapeutic agent. It was unexpectedly found that a compound according to the invention can reduce the off-target effects of current chemotherapeutic agents. A kit according to the invention preferably comprises instructions on dosage regimens obtaining an optimal combined effect of a compound according to the invention and a chemotherapeutic agent.

In another aspect of the present invention, the invention then relates to a diagnostic kit comprising materials for performing a method according to the present invention as herein in one or separate containers, optionally together with auxiliary agents and/or instructions for performing said method according to the present invention. The kit may comprise the compound and/or the compound as identified herein. Furthermore, included can be dyes, antibodies, and other components for detection assays as disclosed above. The kit may comprise the compound and/or the compound as identified herein in labelled form as disclosed above.

The invention shall now be further described in the following examples with reference to the accompanying Figures, nevertheless, without being limited thereto. For the purposes of the present invention, all references as cited herein are incorporated by reference in their entireties.

FIG. 1 shows the sequence of human FOXO4 (*Homo sapiens*) with the sequence of the TP53 interaction domain underlined.

FIG. 2 shows that exemplary peptide CL04009 (SEQ ID NO: 11) is potent in binding recombinant TP53-TAD2 and full-length TP53, isolated from cells and superior to a reference compound (FOXO4-DRI). A) shows the relative NMR chemical shift perturbation of 15N-labeled TP53-TAD2 alone (bottom), in the presence of CL04009 (SEQ ID NO: 11) (top), or a reference compound (middle). The NMR chemical shift perturbation induced by the reference compound has been set to 100%. B) shows a pull-down with streptavidin beads for endogenous TP53 from lysates ofHEK293T cells, either in the absence of any peptide, biotinylated CL04009 (SEQ ID NO: 11), or a biotinylated reference peptide (FOXO4-DRI).

FIG. 3 shows that peptide CL04009 (SEQ ID NO: 11) is potent and selective against senescent, but not healthy control, IMR90 lung fibroblasts. This figure shows that CL04009 (SEQ ID NO: 11), in which modifications were made to improve the binding to TP53, has superior selectivity to induce apoptosis by Caspase-3/7 activation in senescent, but not healthy control IMR90 lung fibroblasts. Furthermore, it is effective at a lower concentration, indicating improved potency. Top graph shows Caspase activity, bottom graph viability of cells. FOXO4-DRI was used as a control.

FIG. 4 shows that CL04022 (SEQ ID NO: 12) is more potent in binding TP53-TAD than the reference compound, FOXO4-DRI. Fluorescence polarization measurements of FITC-labeled TP53-TAD2 (250 nM) in the presence of increasing concentrations of peptides are shown.

FIG. 5 shows peptide CL04022 (SEQ ID NO: 12) to be more stable than CL04009 (SEQ ID NO: 11) over a prolonged period of multiple days, based on the alanine exchange in the peptide. Both peptides were dissolved in $H_2O$ and kept at room temperature. The peptide concentration was determined for the indicated time points.

FIG. 6 shows that peptide CL04022 (SEQ ID NO: 12) starts inducing Caspase-3/7 activation, a measure of canonical apoptosis, at 24 h after administration. Full caspase-3/7 activation is complete after 60 h, top row is control.

FIG. 7 shows that changes in peptide CL04009 (SEQ ID NO: 11) to improve the selective TP53 binding, also result in a very potent and selective capacity to induce apoptosis in senescent (top blue line), but not healthy control (bottom black line) IMR90 cells. The bottom figure shows peptide CL04088 (SEQ ID NO: 13) to be superior to peptide CL04022 (SEQ ID NO: 12), which is still better than the control.

FIG. 8 shows that modifications of peptide CL04009 ((SEQ ID NO: 11) here indicated as CL05055) can further improve the potency to eliminate senescent cells of different origins. RPE=Retinal pigment epithelial cells CL03001 is the same as FOXO4-DRI that was used as a control.

FIG. 9 shows that CL04022 (SEQ ID NO: 12) is superior to FOXO4-DRI in inducing apoptotic cell death in glioblastoma cells. A) CL04022 (SEQ ID NO: 12) is more potent than FOXO4-DRI in inducing Caspase3/-7 activation (apoptosis) and b) loss of LDH (cell death) in GBM8 glioblastoma cells. C) shows CL04022 (SEQ ID NO: 12) to induce apoptosis in GBM8 glioblastoma cells, but not in healthy Wi38 cells. CL04022 (SEQ ID NO: 12) is also selective for inducing apoptosis in GBM8 glioblastoma vs. healthy WI38 cells.

FIG. 10 shows that CL04022 (SEQ ID NO: 12) is effective against colon carcinoma. A) Peptide CL04022

(SEQ ID NO: 12) is effective against two microsatellite-unstable (MSI) colon carcinoma 3D organoid cultures. The peptide is ineffective against one Microsatellite stable (MSS) line. B) shows that CL04022 (SEQ ID NO: 12) is selective against patient-derived colorectal cancers vs. healthy control samples. CL04022 (SEQ ID NO: 12) shows less potency against normal wildtype colon organoids (compared to A) above). The peptide is effective when such organoids are depleted for APC.

FIG. 11 shows show superior stability of CL04183 (SEQ ID NO: 55) and CL05114 (SEQID NO: 60) vs. FOXO4-DRI (CL03001) in solution. In the table, CL02001 designates the "L" form of the peptide CL03001, CL02015 designates the "L" form of peptide CL04183 (SEQ ID NO: 55).

FIG. 15 shows that colorectal cancer associated mutations in colon organoids sensitizes to FOXO4-based peptides, dependent on p53. WT colon and distinct tumor progression (TPO) organoids were treated with increasing concentrations of CL04124 (SEQ ID NO: 68) or CL04183 (SEQ ID NO: 55). Cell viability was measured 5 days later.

Figure 16:
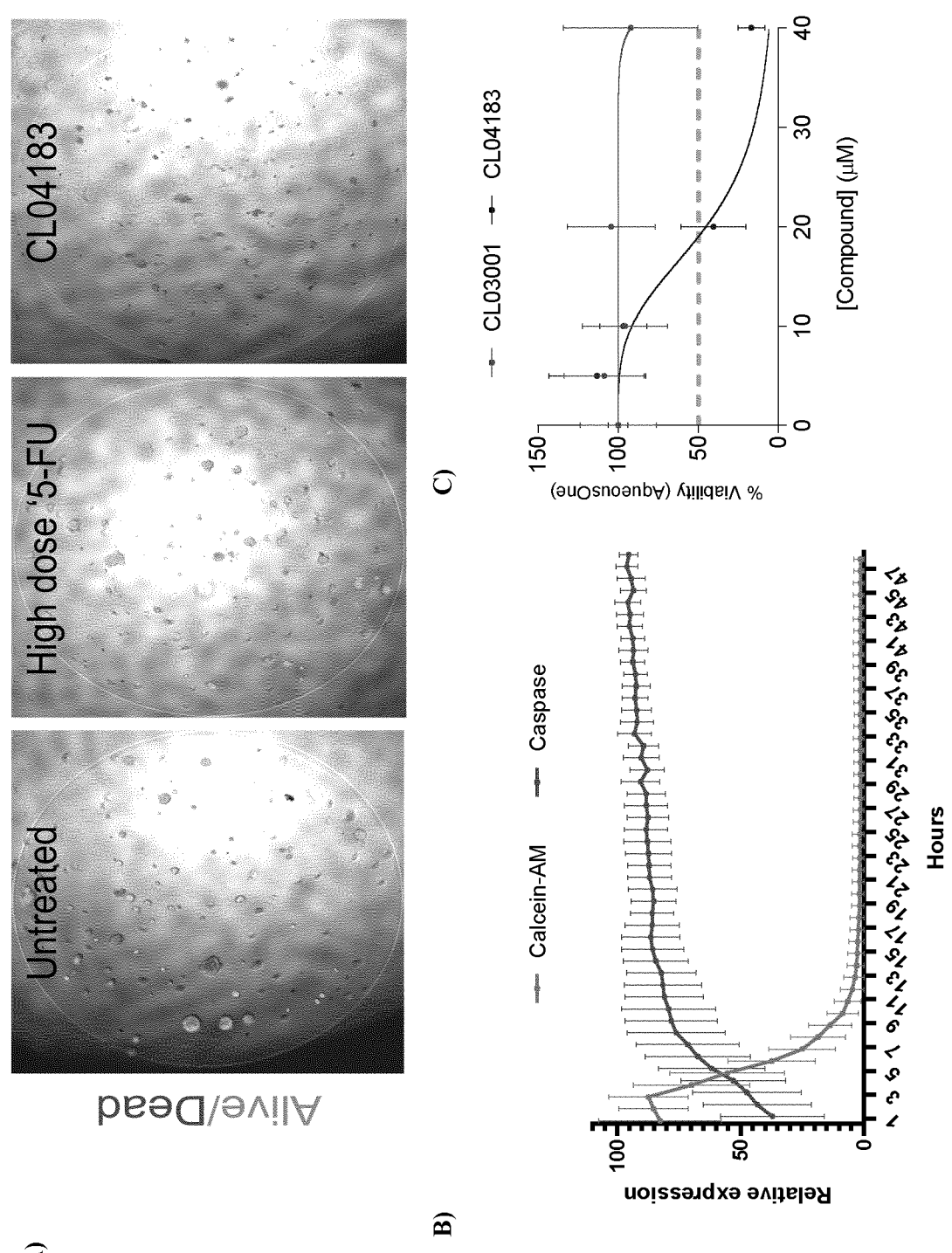

FIG. 16 shows that CL04183 (SEQ ID NO: 55) potently induces apoptosis in patient-derived colorectal cancer organoids. A) Patient-derived colorectal cancer organoid line CRC29 was treated with either '5-Fluorouracil (5-FU) or CL04183 (SEQ ID NO: 55). 3 days later the cells were treated with Calcein-AM and Propidium Iodide, colouring alive and dead cells respectively. The organoids were imaged with the EVOS imaging system. B) CRC29 organoids were incubated with Calcein-AM and a Caspase-3/7 red dye for apoptosis before treatment with CL04183 (SEQ ID NO: 55). Live imaging was started immediately using a LSM880 microscope and images were taken every hour. C) CRC29 were treated with increasing concentrations of CL04183 (SEQ ID NO: 55). Cell viability was measured 5 days later.

Figure 17:
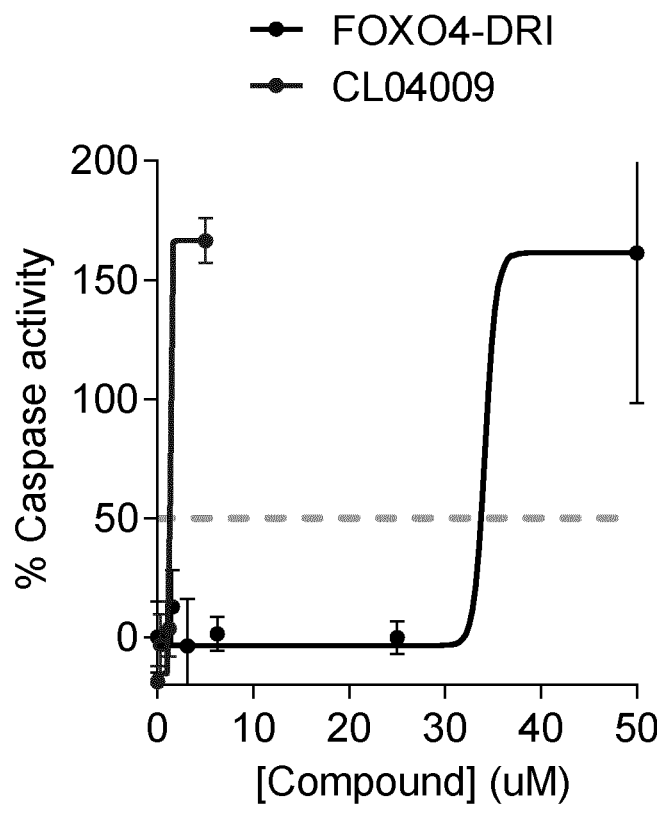

FIG. 17 shows that peptide CL04009 (SEQ ID NO: 11) is more potent in inducing apoptosis in senescent human breast epithelial cells than the reference compound, FOXO4-DRI/CL03001. MCF10 cells were treated with increasing concentrations of CL04009 (SEQ ID NO: 11) and FOXO4-DR and a caspase assay was performed 2 days later to determine apoptosis induction.

Figure 18:
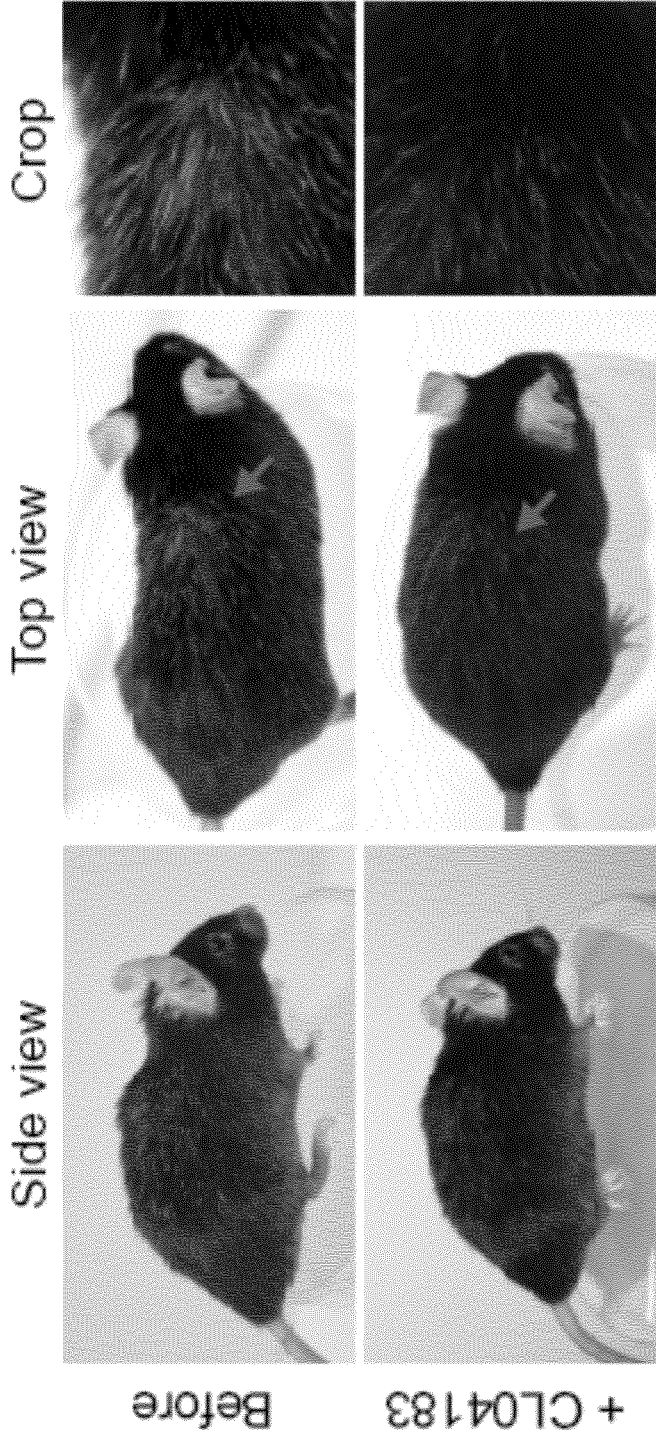

FIG. 18 shows that CL04183 (SEQ ID NO: 55) reduces grey hair in naturally aged mice. 24-month old C57BL/6J mice were photographed before receiving 3 doses of either PBS or CL04183 (SEQ ID NO: 55) through i.v. injection. 4 weeks after the first treatment the mice were photographed again.

FIG. 19 shows that peptide CL04183 (SEQ ID NO: 55) reduces luciferase-expressing colorectal cancer cells in vivo. A) The colorectal cancer organoid line CRC29 containing firefly luciferase was transplanted in the caecum of immunodeficient mice. Two weeks after transplantation bioluminescence levels were determined and the mice were treated with 3 doses of CL04183 (SEQ ID NO: 55) or PBS. All animals were imaged again two days after the last dose and luminescence values were compared to baseline. B) The mice were injected with luciferin before sacrifice. Individual organs were imaged and the luciferase signal quantified using the M3 vision software.

FIG. 20 shows that peptide CL04183 (SEQ ID NO: 55) reduces colorectal cancer metastasis in liver and lung. The colorectal cancer organoid line CRC29 was transplanted in the caecum of immunodeficient mice. Two weeks after transplantation the animals were treated with 3 doses of CL04183 (SEQ ID NO: 55) or PBS. A) The lung and liver were stained for human nucleoli to detect human cancer cells in the mouse organs. B) The amount of metastatic cells in lung was quantified using CellProfiler software. Six tile scans were analysed per mouse. All counts were compared to the average of the PBS treated group. The number of liver metastases per stained section was counted visually.

FIG. 21 shows that CL04183 (SEQ ID NO: 55) induces apoptosis in metastatic cancer cells in vivo. A TUNEL assay was performed on CRC29 lung metastases treated with PBS or CL04183 (SEQ ID NO: 55) to determine apoptosis induction. Three mice per group were included and the percentage of TUNEL positive cancer cells was quantified using FIJI.

Figure 22:
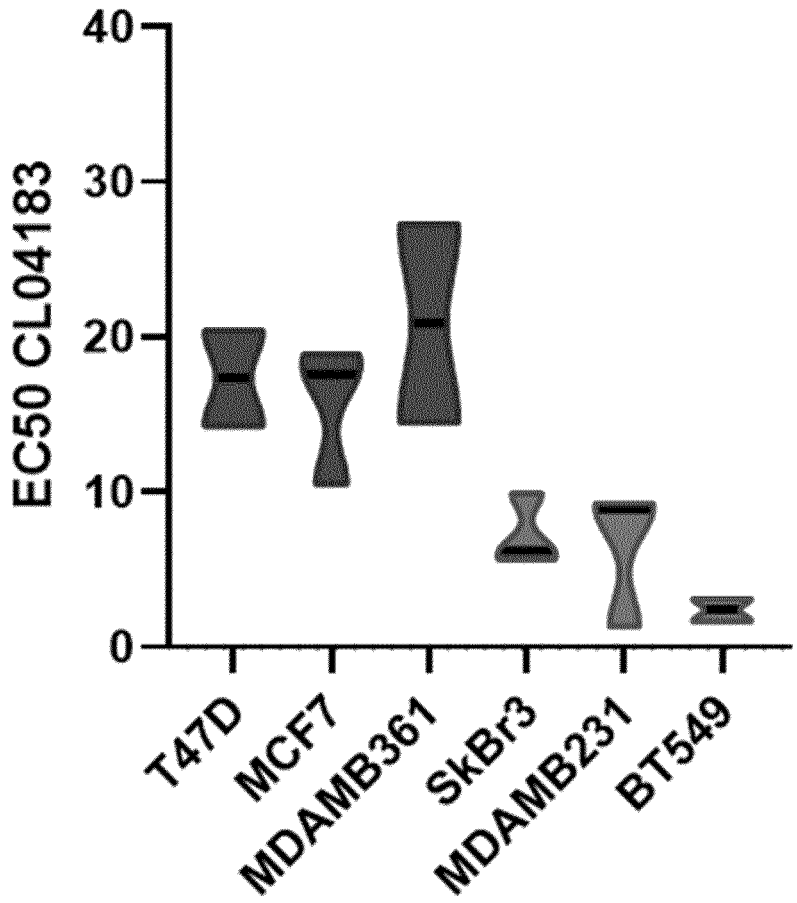

FIG. 22 shows that triple negative breast cancer lines exhibit an open conformation of p53, correlating with CL04183 (SEQ ID NO: 55) sensitivity. The indicated human breast cancer cell lines were treated with increasing concentrations of CL04183 (SEQ ID NO: 55) and an MTS assay was performed 2 days later to determine cell viability. The EC50 values were calculated using GraphPad Prism.

Figure 3:
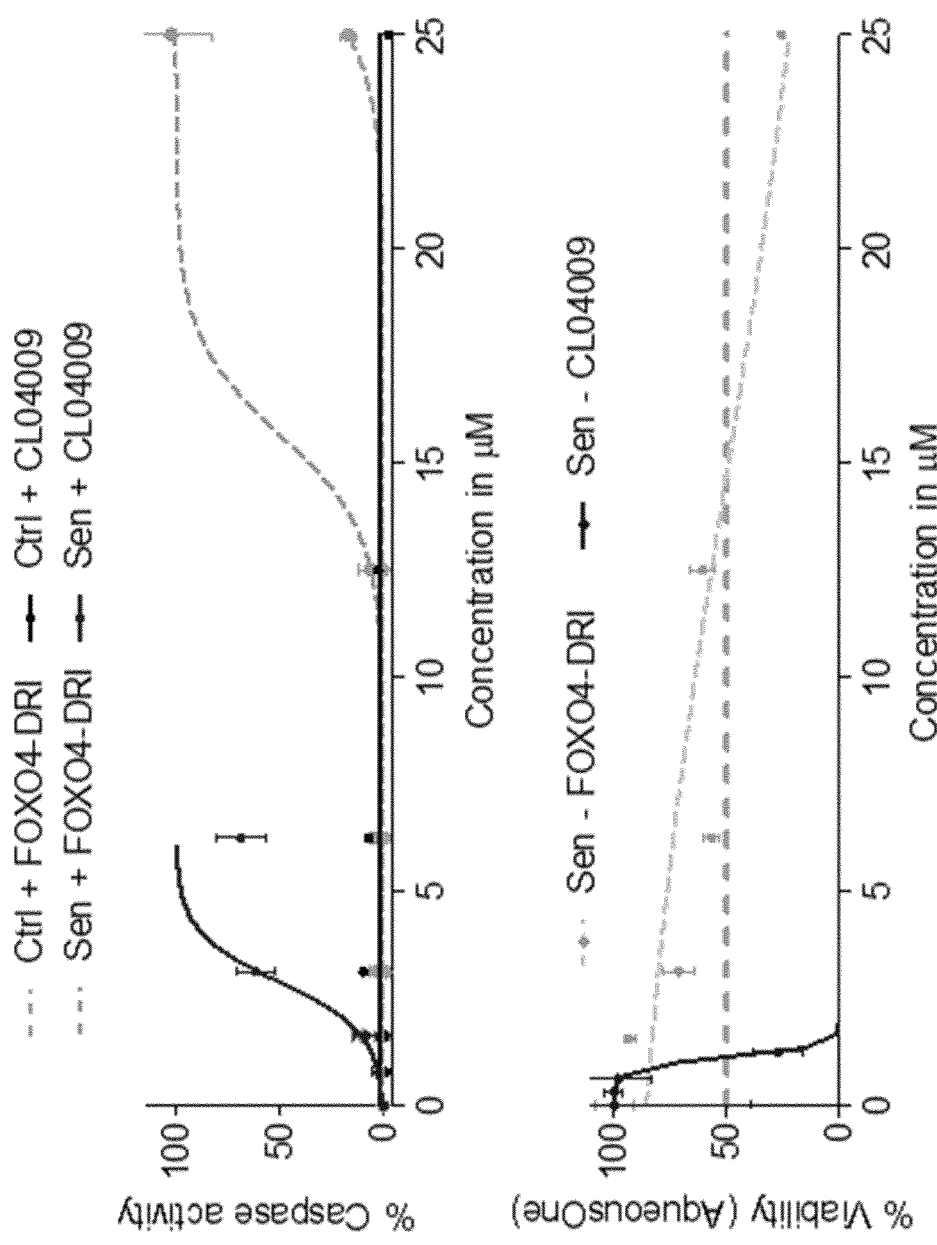
Figure 4:
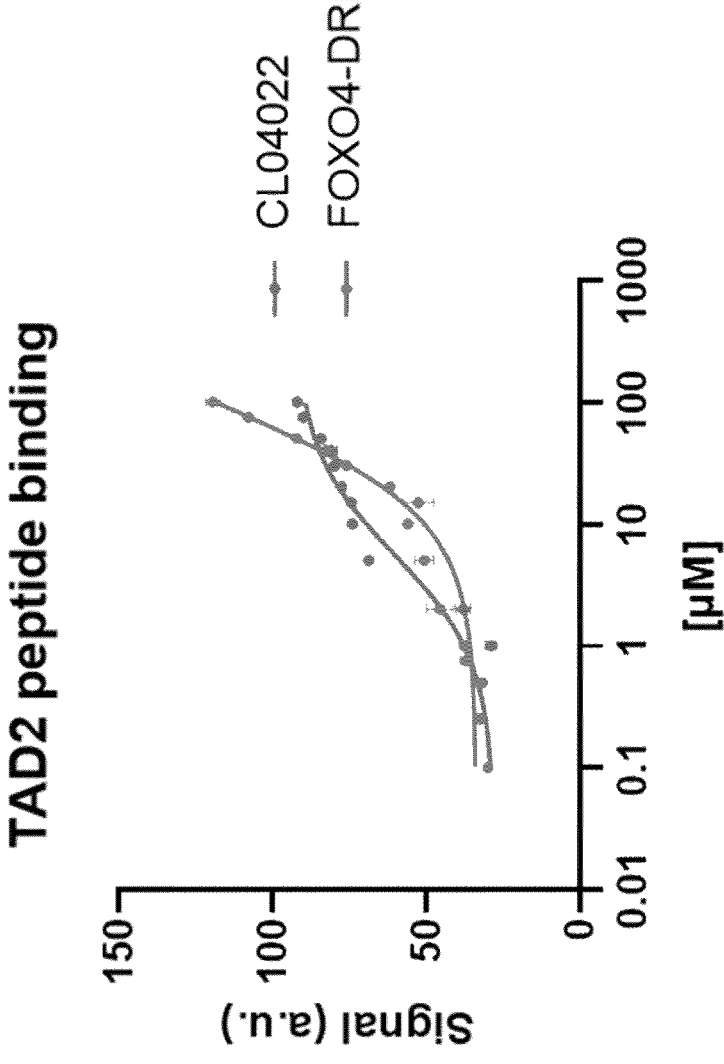
Figure 5:
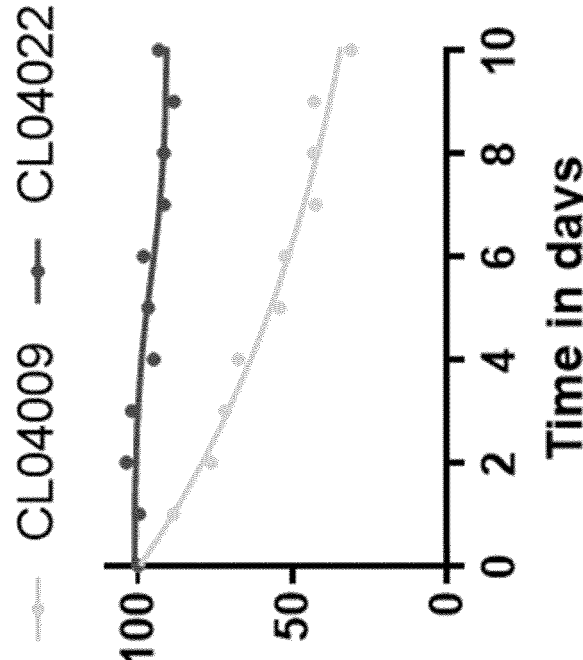
Figure 6:
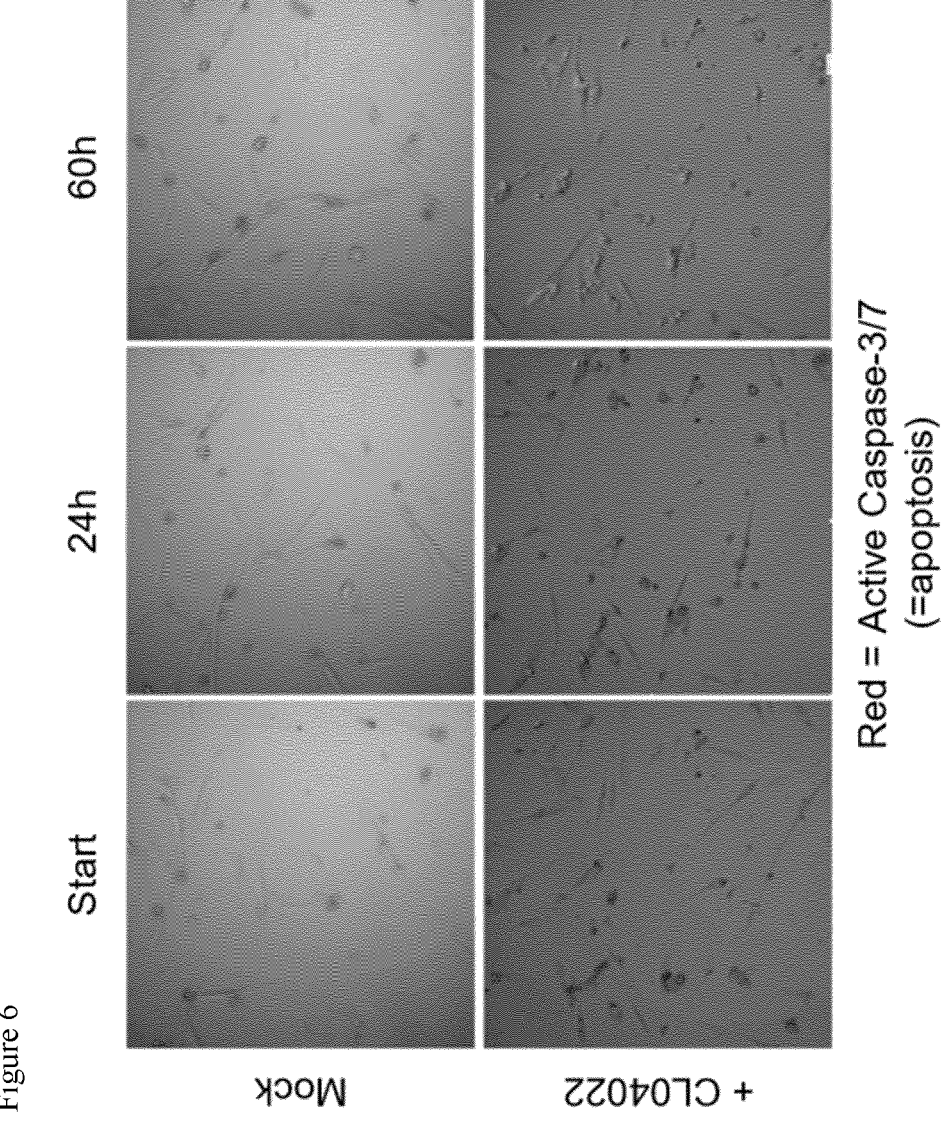
Figure 8:
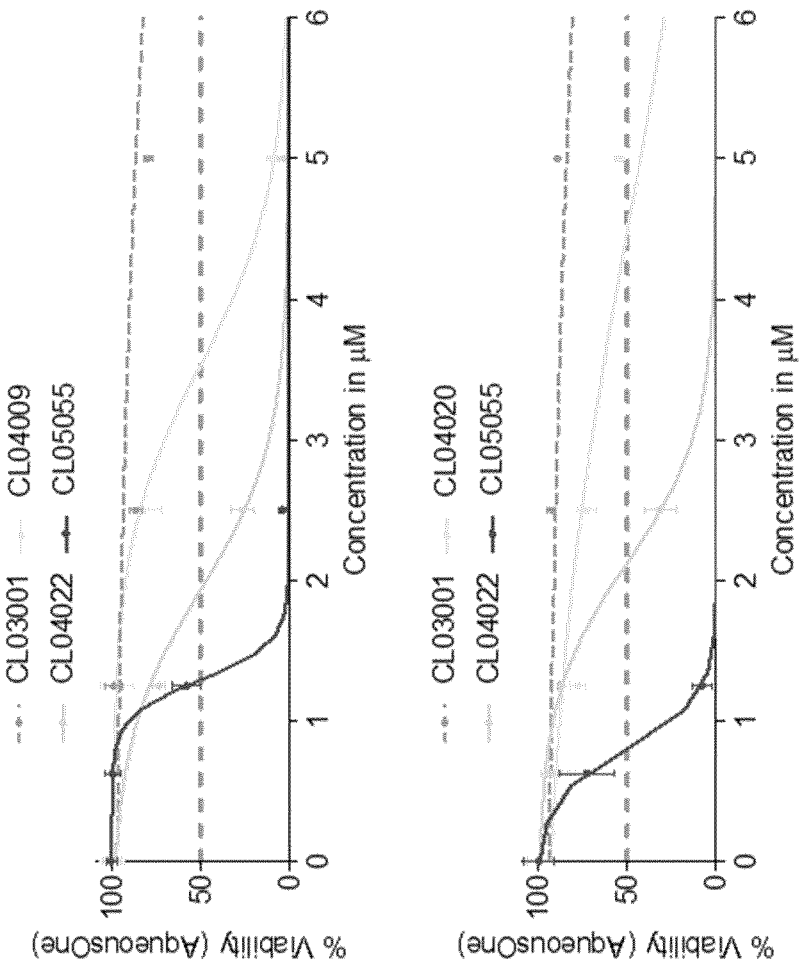
Figure 9:
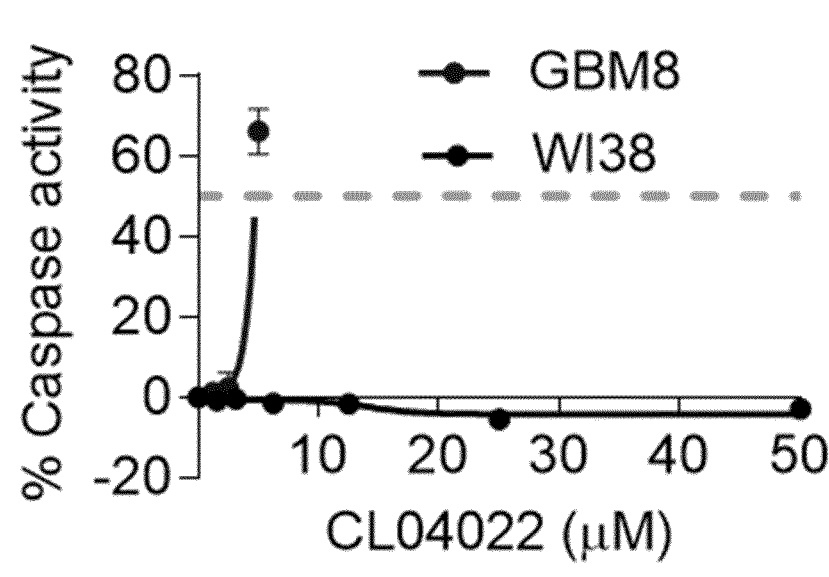
Figure 11:
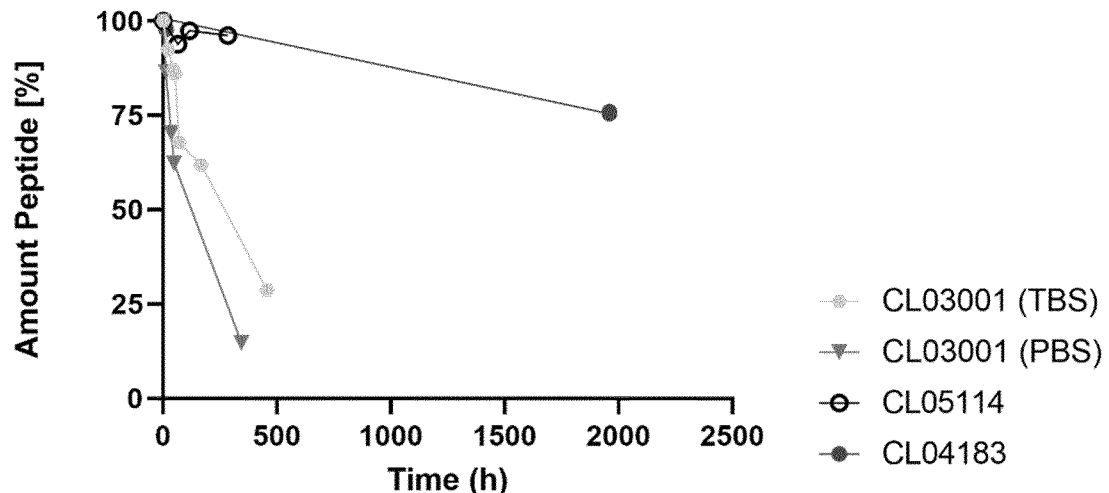
Figure 12:
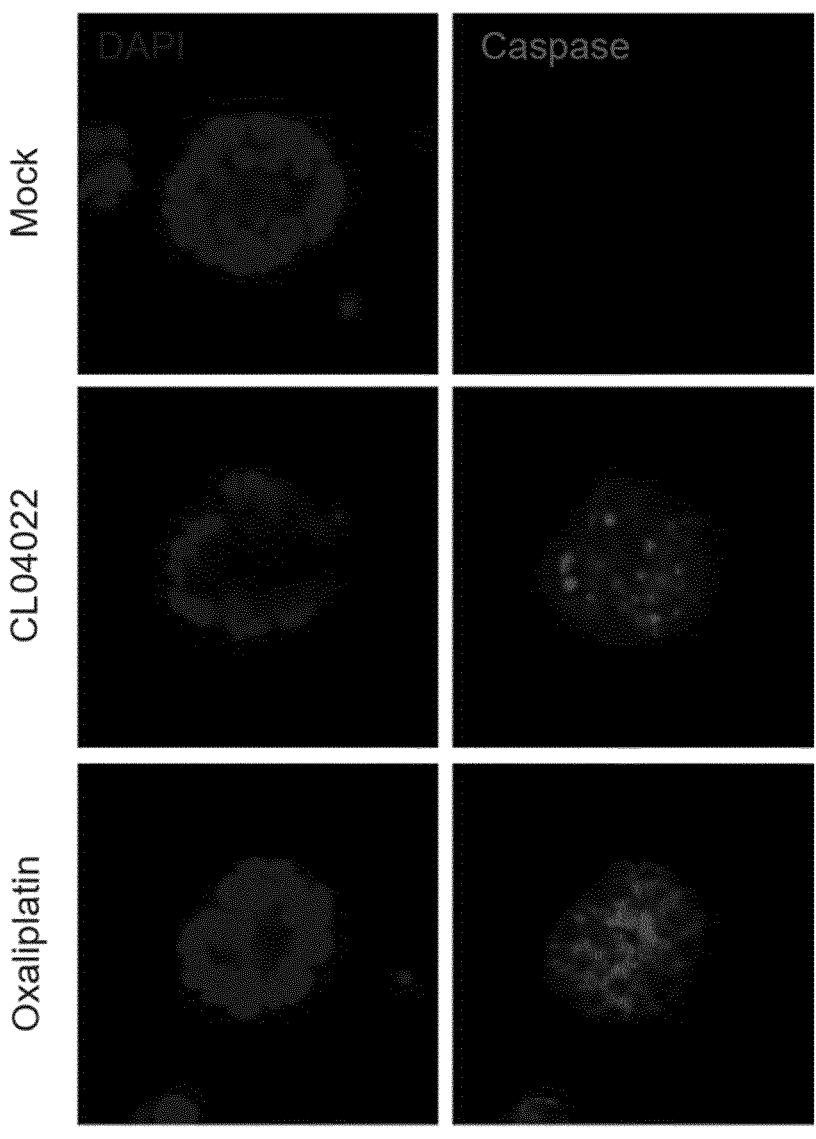
FIG. 12 shows that A) peptide CL04022 (SEQ ID NO: 12) is more effective in colon cancer 3D organoids when they survived chemotherapy (5'FluoroUracil or Oxaliplatin), B) shows that CL04022 (SEQ ID NO: 12) induces cell death, not merely causes a cell cycle arrest, in contrast to standard of care, SFU.
Figure 12:
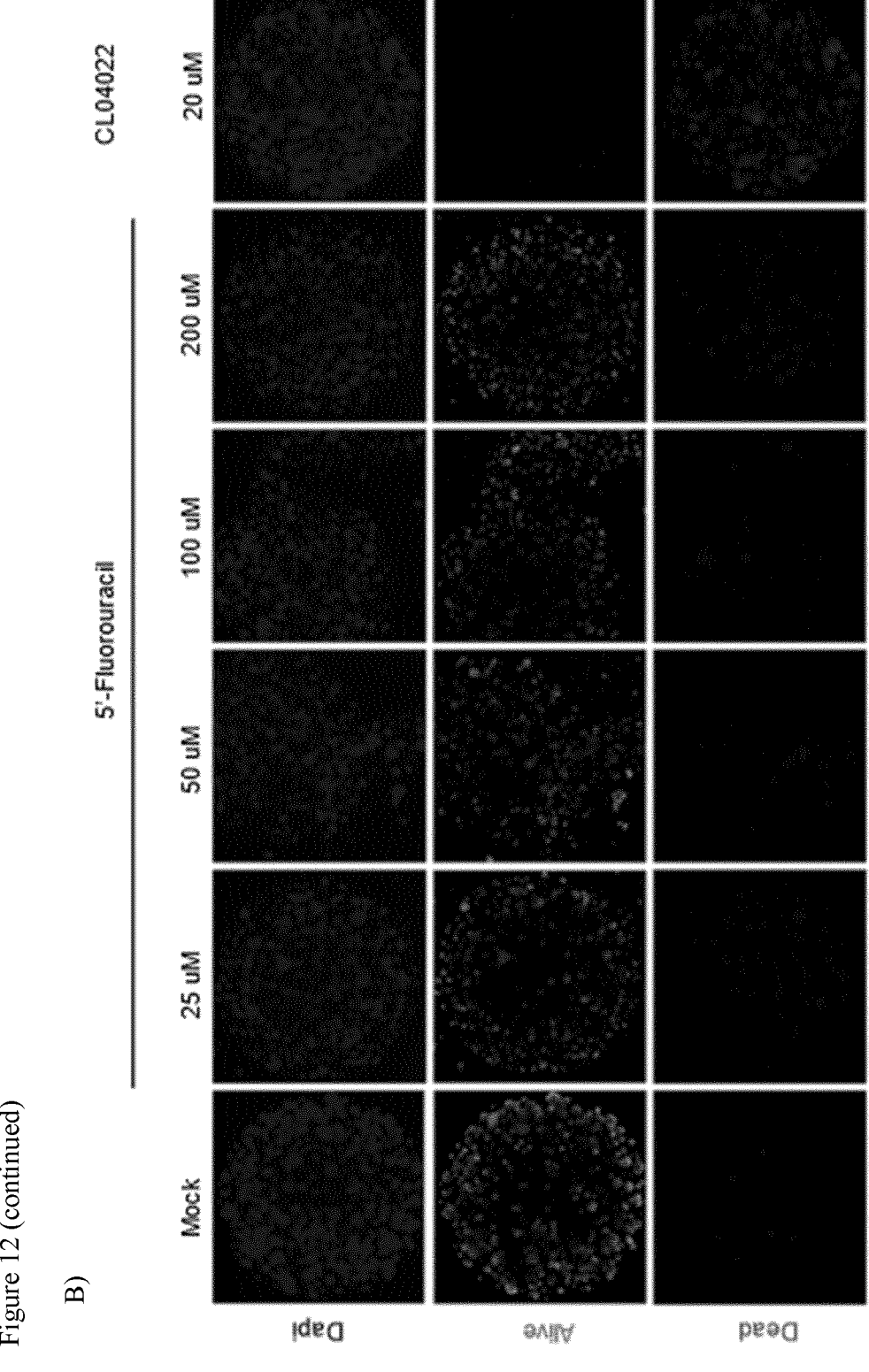
Figure 13:
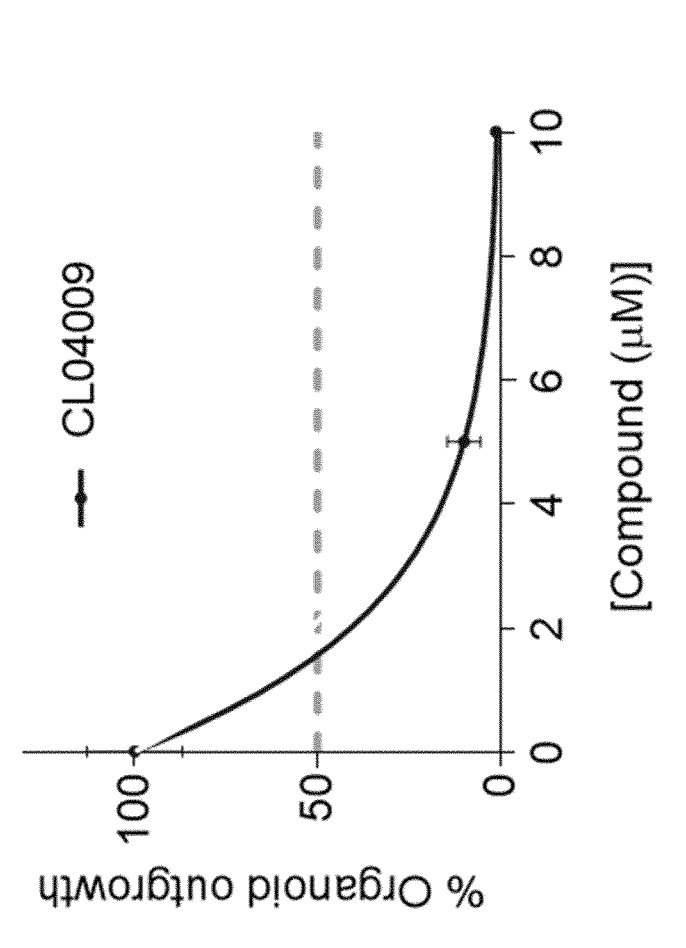
FIG. 13 shows that there is no more tumor outgrowth of 3D colon organoids 14 d after exposure to CL04009 (SEQ ID NO: 11). This indicates CL04009 (SEQ ID NO: 11) is cytotoxic on colon organoids and not just cytostatic, as here shown for the example of colon carcinoma.
Figure 14:
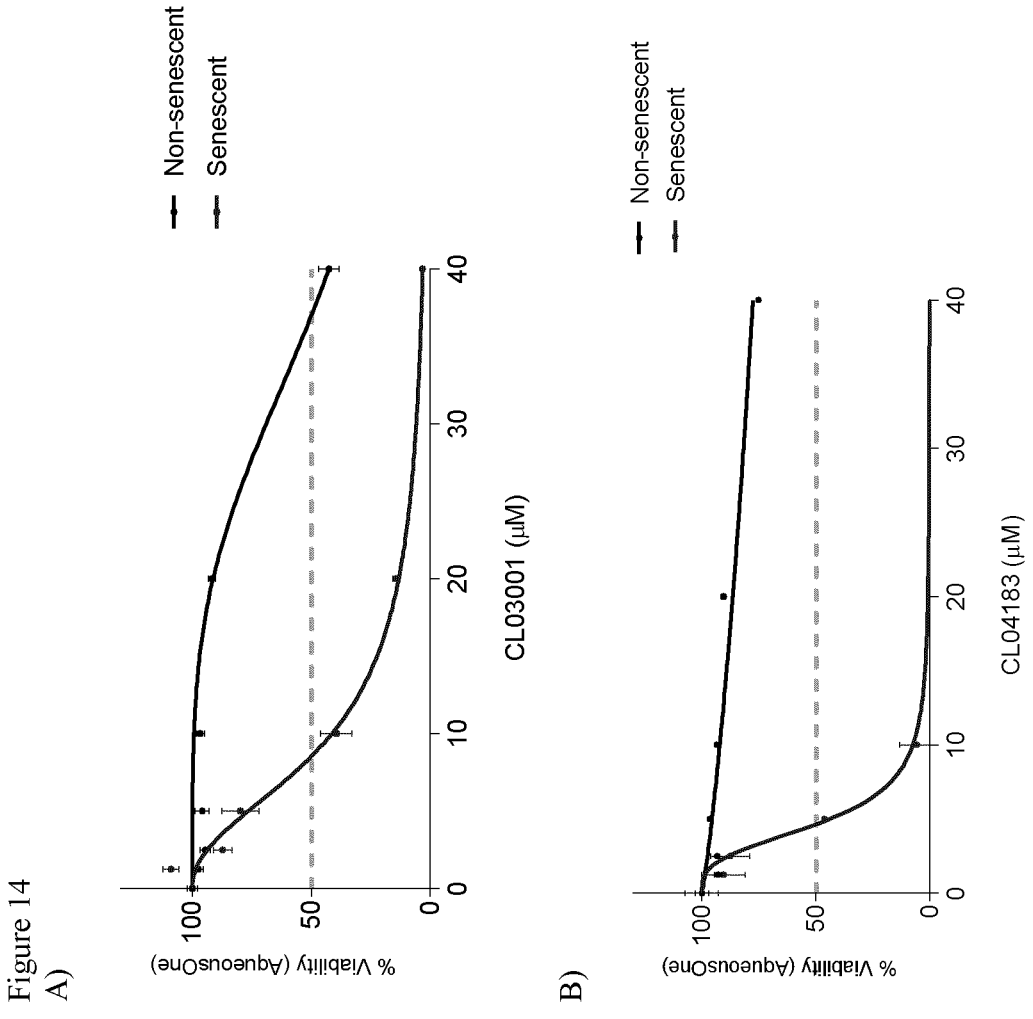
FIG. 14 shows that within one experiment peptide CL04183 (B) (SEQ ID NO: 55) shows superior selectivity and potency vs. the original FOXO4-DRI (CL03001) (A) in senescent vs. ctrl human RPE1 cells.
Figure 23:
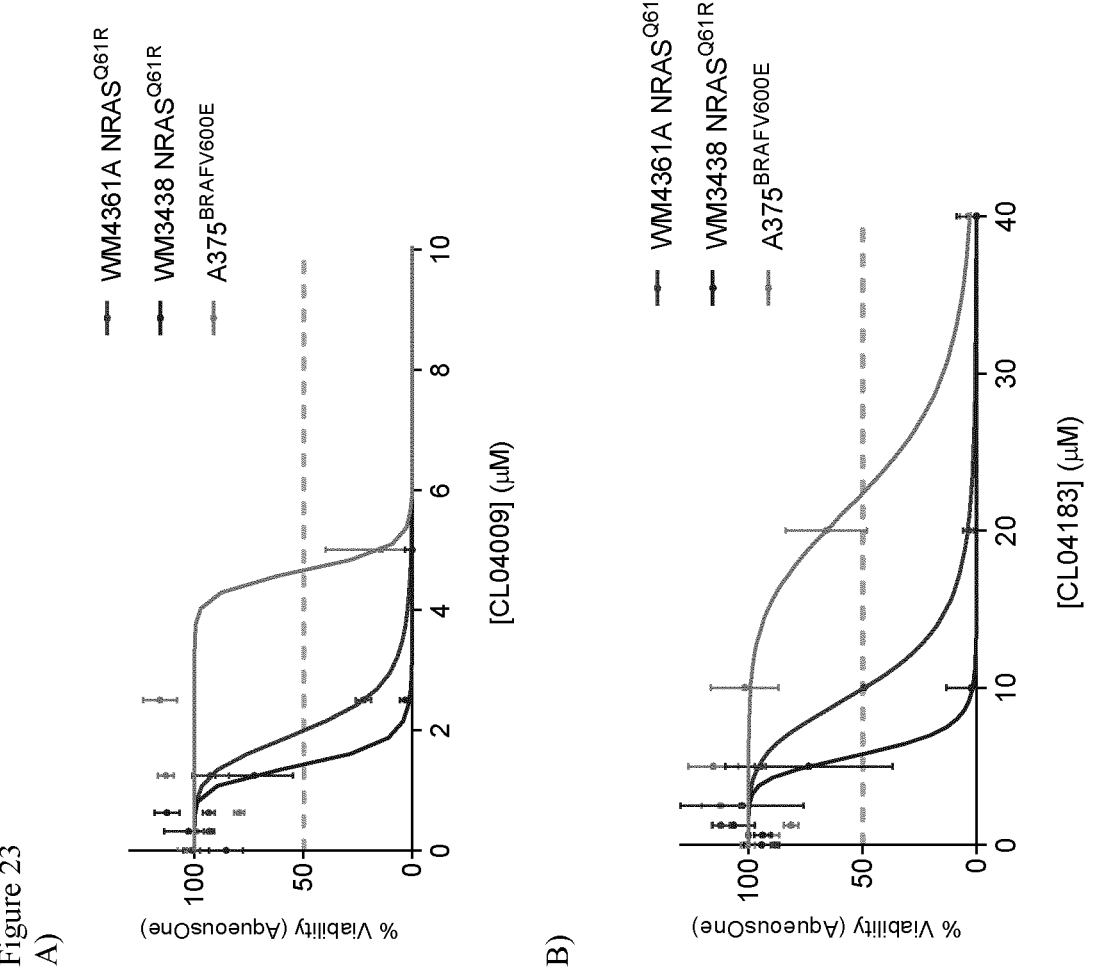

FIG. 23 shows CL04183 (SEQ ID NO: 55) efficacy against NRAS mutated and BRAF mutated melanoma. See also FIG. 14.

Figure 24:
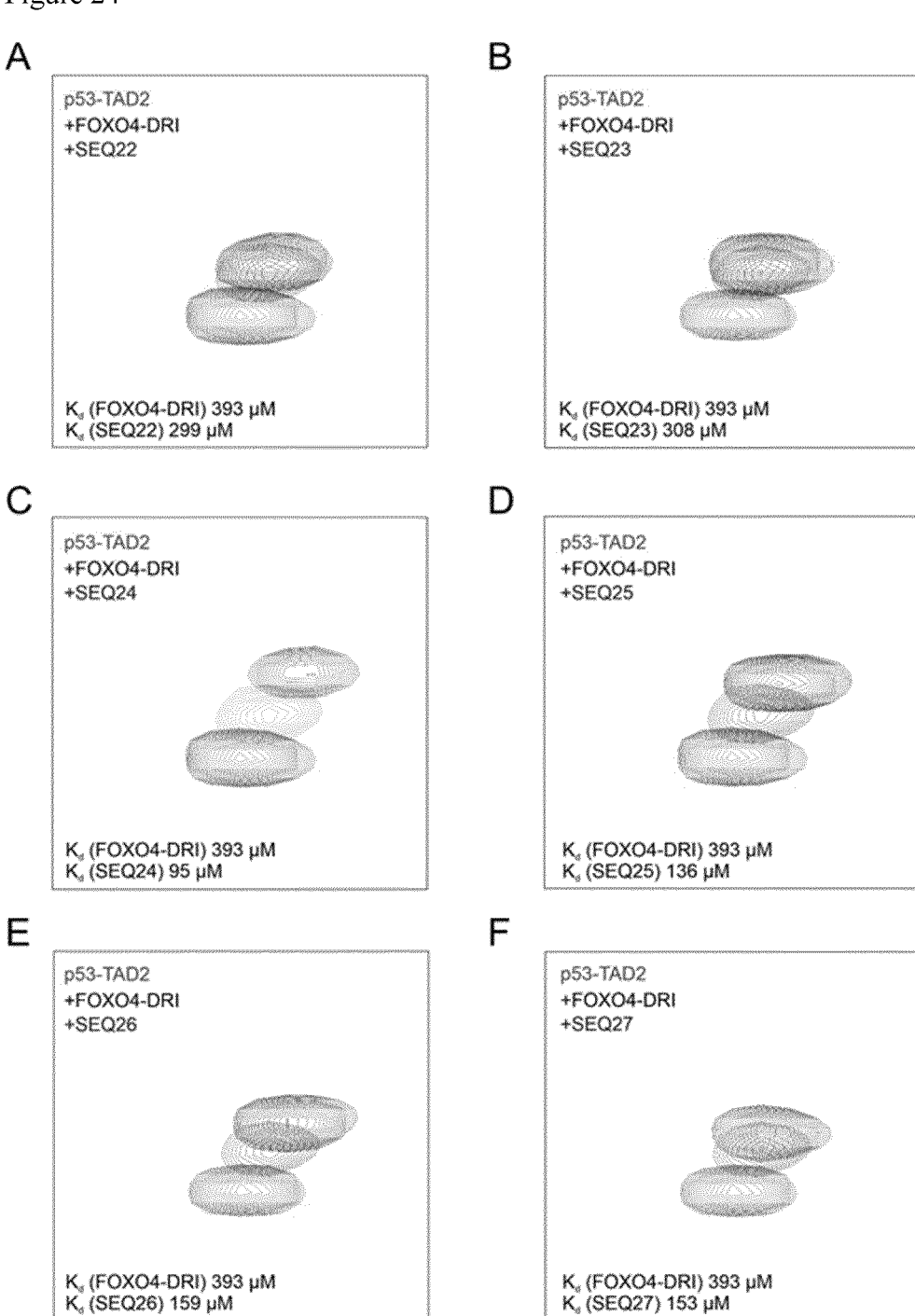

FIG. 24 shows NMR peptide binding data. Zoom of the $^1$H, $^{15}$N cross-peak of the p53-TAD2 T55 extracted from the $^1$H, $^{15}$N HSQC NMR spectra obtained with p53-TAD2 alone (lower circle), upon addition of the reference peptide FOXO4-DRI/CL03001 (black) or upon addition of the tested peptides (upper circle). A) peptide SEQ ID NO: 22, B) peptide SEQ ID NO: 23, C) peptide SEQ ID NO: 24, D) peptide SEQ ID NO: 25, E) peptide SEQ ID NO: 26, and F) peptide SEQ ID NO: 27.

Figure 25:
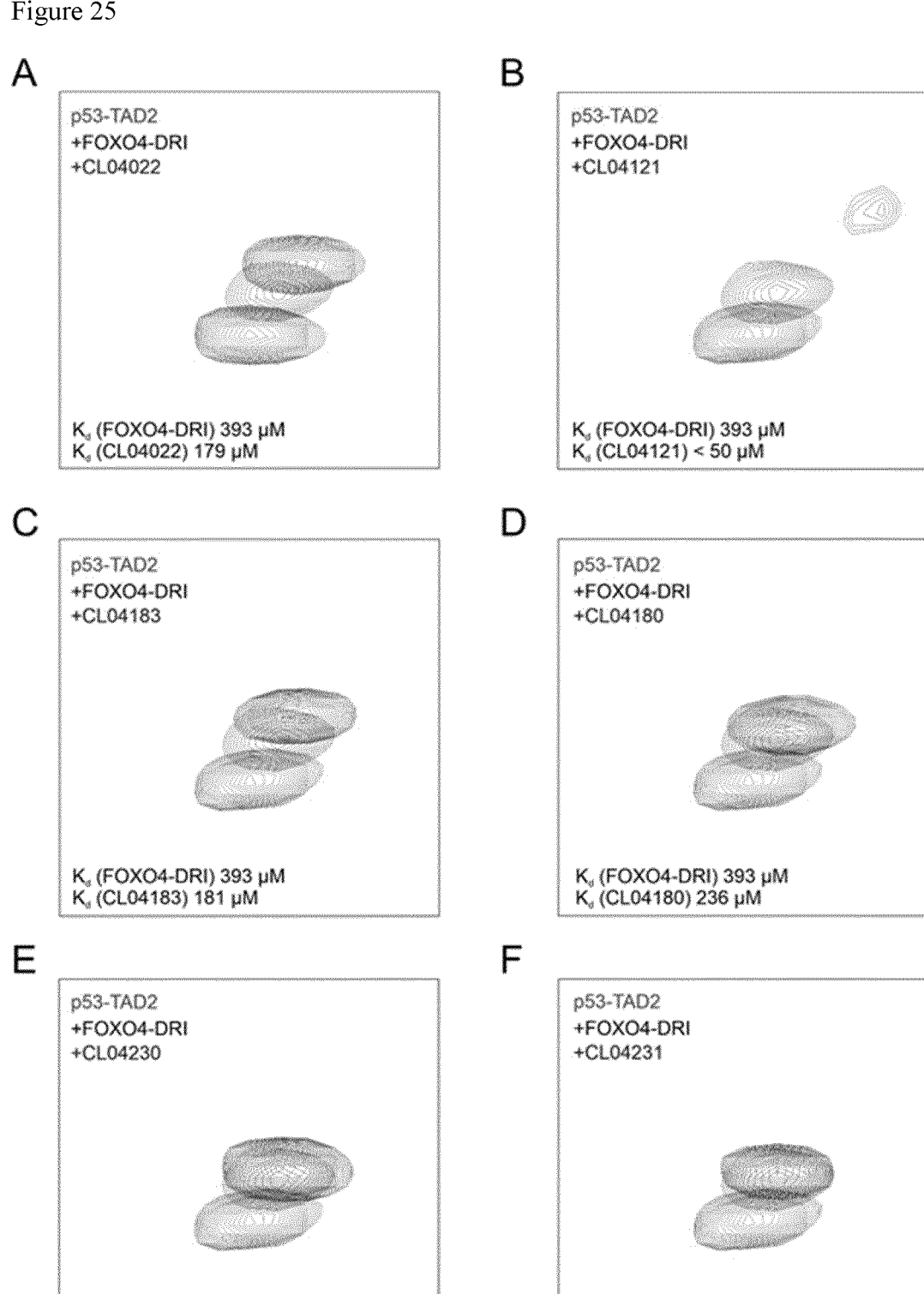

FIG. 25 shows NMR peptide binding data. Zoom of the $^1$H, $^{15}$N cross-peak of the p53-TAD2 T55 extracted from the $^1$H, $^{15}$N HSQC NMR spectra obtained with p53-TAD2 alone (lower circle), upon addition of the reference peptide FOXO4-DRI/CL03001 (black) or upon addition of the tested peptides (upper circle). A) peptide CL04022, SEQ ID NO: 12, B) peptide CL04121, SEQ ID NO: 67, C) peptide CL04183, SEQ ID NO: 55, D) peptide CL04180, SEQ ID NO: 54, E) peptide CL04230, SEQ ID NO: 56, and F) peptide CL04231, SEQ ID NO: 57.

FIG. 26 shows NMR peptide binding data. Zoom of the $^1$H, $^{15}$N cross-peak of the p53-TAD2 T55 extracted from the $^1$H, $^{15}$N HSQC NMR spectra obtained with p53-TAD2 alone (lower circle), upon addition of the reference peptide FOXO4-DRI/CL03001 (black) or upon addition of the tested peptides (upper circle). A) peptide CL04235, SEQ ID NO: 61, B) peptide CL05114, SEQ ID NO: 60.

SEQ ID NOs: 1 to 4, and 7 to 31, and 43 to 66 show peptides of the invention, or parts thereof.

SEQ ID NOs: 5, 6 and 42 show control peptides, e.g. FOXO4-DRI/CL03001.

SEQ ID NOs: 39 and 40 show the amino acid sequences of human FOXO4 and p53, respectively.

EXAMPLES

In the context of the present invention, the terms FOXO4-DRI or CL03001 when relating to a peptide and/or control peptide refer to the peptide with the D-amino acid sequence LTLRKEPASEIAQSILEAYSQNGWANRRSGGKRPP-PRRRQRRKKRG (SEQ ID NO: 6) or L-amino acid sequence PRKGGSRRNAWGNQSYAELISQAIESA-PEKRLTL (SEQ ID NO 42).

Cell Culture:

Human IMR90, WI38 and RPE cells were grown in Dulbecco's Modified Eagle's Medium (DMEM; Lonza) containing 10% FCS and 1% pen/strep at 37° C. with 3.0% $O_2$ and 5.0% $CO_2$. To induce senescence, cells were irradiated with 10Gy ionizing radiation (Gammacell 1000) and were left for a minimum of 10 days to become senescent.

GBM8 cells were cultured in Dulbecco's Modified Eagle's Medium/Nutrient Mixture F-12 (DMEM F-12), containing high glucose, L-Glutamine, no phenol red, supplemented with 1% (10 mM) HEPES, 1% Penicillin/Streptomycin, 2% B-27 (50×), 5 µg/ml Heparin sodium salt from porcine intestinal mucosa Grade I-A, 20 ng/ml recombinant human Fibroblast Growth Factor (rhFGF) and 20 ng/ml recombinant human Epidermal Growth Factor (rhEGF). These cells were cultured in plastic ware coated with Matrigel Matrix (20× diluted in DMEM F-12) at 37° C., 5% $CO_2$ and 3% $O_2$ in a humified incubator.

To perform viability and apoptosis assays, cells were split into 96-well plates and treated with peptides 2 days later. Non-senescent and cancer cells were plated 1500 cells/well, while senescent cells were plated at 8.000 cells/well.

Organoid Culture:

Organoids were grown at 37° C. and 5% $CO_2$ in a humidified incubator. All organoids were cultured in matrigel (Corning) droplets in advanced DMEM/F12 (Lonza) supplemented with 1% glutamax, 1% Penicillin/Streptomycin, 1% (10 mM) HEPES, 10% Noggin conditioned medium, 2% B-27 (50×; (Thermo/Life Technologies), N-acetylcysteine ((Sigma-Aldrich, 1.25 mM)), A83-01 (Tocris, 500 nM) and SB203580 (Invitrogen/Life Technologies, 3 µM). To perform viability and apoptosis assays, the organoids were passaged through resuspension in ice-cold medium, followed by centrifugation in 15 ml tubes at 4° C. The resulting pellet was trypsinized for 5 minutes at 37° C. to obtain single cells and subsequently washed twice with advanced DMEM/F12 media. These cells were then resuspended in Matrigel and plated in 96-well plates in 5 ul droplets. 100 ul fresh medium was added to the wells 15 minutes later. Peptide and chemotherapy treatment was added to the organoids 2 days after plating.

Caspase Assay:

For a caspase assay, Caspase-Glo 3/7 assay reagent (Promega) was added to the medium 2 days after treatment. The plates were then incubated in aluminium foil at room temperature on a shaker for 1 hour and subsequently measured with a Luminescence Plate Reader.

MTS Assay:

Six days after treatment, cells were incubated with 10 ul CellTiter 96® AQueous One Solution Cell Proliferation Assay (Promega) for 1 hour at 37° C. to perform an MTS assay. Subsequently, absorbance was measured at 490 nm using a Spectramax M5e.

Live/Dead Assay on Organoids:

A Live/dead assay was performed on both larger organoids 3 days after peptide and/or chemotherapy treatment, or on organoids that were treated as single cells and allowed to grow out for 2 weeks before the assay was performed. To perform the assay, Calcein-AM (1:1000) and Propidium Iodide (PI; 1:100) were added to the medium of the organoids to detect living and dead cells respectively. The organoids were then imaged on a Zeiss Cell Observer microscope and the signal was quantified using FIJI.

Live Imaging:

Organoids and IMR90 cells were grown in 96-well cell culture plates and either the 488 IncuCyte Caspase 3/7 Reagent For Apoptosis (Sartorius) or the IncuCyte Caspase 3/7 red apoptosis assay reagent (Essen Bioscience) was added to the wells. Peptides were added directly before the plate was transferred to a Zeiss Cell Observer microscope that contains a Heat and CO2-controlled compartment. Subsequently, live imaging was started where a picture was recorded every 2 hours for 60 hours. Images were processed using Zen imaging software (Zeiss).

Alternatively, live imaging was performed on a LSM880 confocal microscope. For this experiment organoids were plated on a glass bottom cell culture dish and incubated with Calcein-AM (Sigma-Aldrich) to measure cell viability and the IncuCyte Caspase 3/7 red apoptosis assay reagent (Essen Bioscience). Peptides were added directly before imaging was started.

Mice

Mouse experiments were performed after approval from the Dutch animal ethics committee. For these experiments male NOD.Cg-Prkdc$^{scid}$ Il2rg$^{tm1Wjl}$/SzJ/J mice (Charles River) were employed. Human CRC29 colorectal cancer organoids containing firefly luciferase were implanted into the caecum, resulting in the formation of a primary tumor at this site. The implantation was performed under ketamine and dexmedetomidine anaesthesia. In addition, the animals received carpofen 30 min before surgery and the day after. 14 days after transplantation, the mice were sedated using isoflurane and imaged under the BioSpace Imager. Subsequently, The animals were treated with either PBS or with '5-Fluorouracil (5-FU) at a dose of 50 mg/kg via i.p. injection. The first dose of CL04183 (2.5 mg/kg) was administered via i.v. injection 1 week after 5-FU treatment and this treatment was repeated 2 and 4 days later. 4 weeks after transplantation, the mice were imaged again to determine treatment effect and subsequently sacrificed. All organs were harvested and imaged under the BioSpace Imager again and the luciferase signal was quantified using the M3 vision software.

Immunohistochemistry

Liver and lung paraffin sections were rehydrated in decreasing concentrations of ethanol before being washed in TBS and boiled for 20 minutes in 10 mM sodium citrate buffer (PH6) for antigen unmasking. After the slides were left to cool for 30 minutes, the tissue was permeabilized with 0.2% TX-100 in TBS for 5 minutes at room temperature. Subsequently, the sections were washed with TBS and incubated for 1 hour in blocking buffer containing 2% w/v secondary antibody-appropriate sera (e.g. donkey or goat) and 0.1% fish gelatin in 1% BSA. The sections were then encircled with a water-repellent pen and incubated with the primary antibody diluted in TB S/1% BSA overnight at 4° C. The next day, the tissues were washed 3 times with TBS before an hour incubation with fluorescent labelled secondary antibody diluted in blocking buffer (containing nuclear staining with Hoechst 33342). Subsequently, the slides were washed twice in TBS, incubated in Sudan black solution for 20 min to reduce background and washed in demineralized water. The sections were then mounted with Vectashield and imaged using a LSM880 Zeiss confocal microscope.

Apoptosis Staining

A TUNEL assay was performed on lung metastases to determine apoptosis induction after treatment. Rehydrated sections were treated with 20 ug/ml ProtK solution in PBS for 15 minutes and permeabilized in 0.1% Triton X-100 in 0.1% sodium citrate. Subsequently, the tissue was labelled for 1 hour with 10% TUNEL enzyme in labelling solution (ROCHE) at 37° C. Nuclei were labelled with Hoechst 33342 (ThermoFisher) before the slides were mounted with soft set mounting medium (Vectashield). Images were acquired using a LSM880 confocal microscope (Zeiss) and the percentage of TUNEL-positive cells was analysed using FIJI.

Protein Expression and Purification:

Expression constructs for the fragments of human p53 from 1 to 312 (p53-TADBD), 94 to 312 (p53-DBD), amino acid 1 to 94 (p53-TAD), and amino acid 37 to 57 (p53-TAD2) were generated by synthesis of the corresponding optimized p53 cDNA constructs and inserted into pETM11-ZZ-His$_6$ vector using NcoI/BamHI restriction sites (Genscript). The inventors also generated optimized cDNA expression constructs (Genscript) in pETM11-ZZ-His$_6$ vector for fragment of human FOXO4 from amino acids 86 to 208 (FOXO4-FH). The inventors employed three different chemically competent E. coli strains (E. coli BL21(DE3) and E. coli BL21-(DE3 Star) for protein expression and E. coli TOP10 for amplification of plasmid DNA).

Protein expression and purification were carried out using protocols as published and known to the person of skill.

Fluorescence Polarization:

116 µl of a solution of the specific peptides (ranging from 1 to 100 µM) were prepared. Subsequently 4 µl of FITC-labelled p53 peptide (stock concentration 15 resulting in a final concentration of 500 nM) were added. 35 µl were then transferred in each well of the 384-well plate. Measurements were performed in triplicates.

Data was acquired on a ClarioStar Plus platereader. End-point measurement with 200 flashes per well were performed. An excitation filter with 482 nm wavelength and emission filter with 530 nm were used and gain adjustment as well as focal height adjustment were performed for each measurement. Fluorescence intensity, parallel fluorescence polarization and perpendicular fluorescence polarization were recorded.

Data analysis was performed using MARS Version 3.4 (BMG), Microsoft Excel and GraphPad Prism Version 8.

NMR Chemical Shift Mapping:

A 5 mm NMR tube containing 500 µl 100 µM p53-TAD2 was prepared and a $^1$H,$^{15}$N HSQC NMR spectrum was recorded. Then increasing amounts of peptide were added stepwise, followed by measurement of another $^1$H,$^{15}$N HSQC spectrum after each step. NMR spectra were acquired on a 600 Mhz Bruker Avance NOE NMR spectrometer equipped with a TXI 600S3 probehead. Data acquisition and processing was performed with Topspin3.5 and Topspin4.0 (Bruker). Data analysis, peak picking and assignments were performed using ccpNMR.

TABLE 1

Selection of peptides according to the present invention

| Intern. No. | SEQ ID NO: | Sequence |
|---|---|---|
| CL7 | 7 | LTL R K E A S S E I A Q S I L D A Y S Q N G W A N R R S S C K R P |
| CL8 | 8 | LTL R K K A S S K I A Q S I L D A F S Q N G W A N R R S S C K R P |
| CL6 | 6 | LTL R K E P A S E I A Q S I L E A Y S Q N G W A N R R S G G K R P |
| CLIO | 10 | R K K A S S K I A Q S I L D A F S Q N G W A N R R S S C K R P |
| CL4009 | 11 | R K K A S S K I A A A I L D A F S Q N G W A N R R S S C K R P |
| CL4022 | 12 | R K K A S S K I A A A I L D A F S Q N A W A N R R S S C K R P |
| CL4088 | 13 | R K K A S S K I A A A I L D A F S Q N   W   R R     K R |
| CL14 | 14 | R K K A S S K I E A A I L D A F S Q N   W   R R     K R |
| CL15 | 15 | R K K A S S K I A A E I L D A F S Q N   W   R R     K R |
| CL16 | 16 | R K K A S S K I E A E I L D A F S Q N   W   R R     K R |
| CL17 | 17 | R K K   S K I A A A I L D A F S Q N   W   R R     K R |
| CL18 | 18 | R K K   S K I E A E I L D A F S Q N   W   R R     K R |
| CL19 | 19 | A K       I A A A I L D A F S Q N   W   R R     K R |
| CL20 | 20 | A K       I E A A I L D A F S Q N   W   R R     K R |
| CL21 | 21 | LTL R K E P A S E I A Q S I L E A Y S Q N G W A N R R S G G K R P - P P R R R Q |
| CL22 | 22 | R K K A S S K I A A A I L D A F S Q N G W A N R R S S C K R P - P P R R R Q R R K |
| CL23 | 23 | R K K A S S K I A A A I L D A F S Q N A W A N R R S S C K R P - P P R R R Q R R K |
| CL24 | 24 | R K K A S S K I A A A I L D A F S Q N   W   R R     K R   - P P R R R Q R R K K R G |

TABLE 1-continued

Selection of peptides according to the present invention

| Intern. No. | SEQ ID NO: | | | | | |
|---|---|---|---|---|---|---|
| CL25 | 25 | R K K A S S K I E A A I L D A F S Q N | W | R R | K R | - P P R R R Q R R K K R G |
| CL26 | 26 | R K K A S S K I A A E I L D A F S Q N | W | R R | K R | - P P R R R Q R R K K R G |
| CL27 | 27 | R K K A S S K I E A E I L D A F S Q N | W | R R | K R | - P P R R R Q R R K K R G |
| CL28 | 28 | R K K   S K I A A A I L D A F S Q N | W | R R | K R | -   R R Q R R K K R G |
| CL29 | 29 | R K K   S K I E A E I L D A F S Q N | W | R R | K R | -   R R Q R R K K R G |
| CL30 | 30 | A K I A A A I L D A F S Q N | W | R R | K R | -   R R Q R R K K R G |
| CL31 | 31 | A K I E A A I L D A F S Q N | W | R R | K R | -   R R Q R R K K R G |
| CL32 | 53 | R K K A S S K I E A E I L D A F S Q N | W | R R | K R | - P P R R R Q R R K K R G |
| CL33 | 54 | R K K   S K I E A E I L D A F S Q N | W | R | K R | -   R R Q R R K K R G |
| CL34 | 55 | A K I E A A I L D A F S Q N | W | R | K R | -   R R Q R R K K R G |
| CL35 | 56 | A K I E A E I L D A F S Q N | W | R | K R | -   R R Q R R K K R G |
| CL36 | 57 | A K I E A A I L D E F S Q N | W | R | K R | -   R R Q R R K K R G |
| CL37 | 58 | R K K A S J K I A I A I L D A F S Q N | W | R R | K R | - P P R R R Q R R K K R G |
| CL38 | 59 | R K K A S S K I A A A Z L D A F S Q N | A W A N | R R | S S C K R | P P P R R R Q R R K K R A |
| CL39 | 60 | A K I E A A I L D A F S Q N | B | R | K R | R R Q R R K K R G |
| CL40 | 61 | A K I E A E I L E A F S Q N | B | R | K R | R R Q R R K K R G |
| CL41 | 62 | A K I E A A Z L D A F S Q N | B | R | K R | R R Q R R K K R G |
| CL42 | 63 | R K K A S S K I E A E I L D A F S Q N | B | R R | K R | P P R R R Q R R K K R G |
| CL43 | 64 | R K K A S S K I E A E Z L D A F S Q N | B | R R | K R | P P R R R Q R R K K R G |
| CL44 | 65 | R K K A S S K I E A E I Z D A F S Q N | B | R R | K R | P P R R R Q R R K K R G |
| CL45 | 67 | R K K   S K I A A A I L D A F Q N | W | R | K R | R R Q R R K K R G |
| CL46 | 68 | R K K A S S K I E A A I L D A F S Q N | W | R R | K R | P P R R R Q R R K K R G |

The invention claimed is:

1. A peptide comprising an amino acid sequence selected from the group consisting of i)

```
                                    (SEQ ID NO: 7)
LTLRKEASSEIAQSILDAYSQNGWANRRSSCKRP, (SEQ ID NO: 8)
LTLRKKASSKIAQSILDAFSQNGWANRRSSCKRP,
```

-continued
```
                                    (SEQ ID NO: 10)
RKKASSKIAQSILDAFSQNGWANRRSSCKRP, (SEQ ID NO: 11)
RKKASSKIAAAILDAFSQNGWANRRSSCKRP, (SEQ ID NO: 12)
RKKASSKIAAAILDAFSQNAWANRRSSCKRP, (SEQ ID NO: 13)
RKKASSKIAAAILDAFSQNWRRKR,
```

-continued

```
                                   (SEQ ID NO: 14)
RKKASSKIEAAILDAFSQNWRRKR, (SEQ ID NO: 15)
RKKASSKIAAEILDAFSQNWRRKR, (SEQ ID NO: 16)
RKKASSKIEAEILDAFSQNWRRKR, (SEQ ID NO: 17)
RKKSKIAAAILDAFSQNWRRKR, (SEQ ID NO: 18)
RKKSKIEAEILDAFSQNWRRKR, (SEQ ID NO: 19)
AKIAAAILDAFSQNWRRKR, (SEQ ID NO: 20)
AKIEAAILDAFSQNWRRKR, (SEQ ID NO: 22)
RKKASSKIAAAILDAFSQNGWANRRSSCKRPPPRRRQRRKKRG, (SEQ ID NO: 23)
RKKASSKIAAAILDAFSQNAWANRRSSCKRPPPRRRQRRKKRA, (SEQ ID NO: 24)
RKKASSKIAAAILDAFSQNWRRKRPPRRRQRRKKRG, (SEQ ID NO: 25)
RKKASSKIEAAILDAFSQNWRRKRPPRRRQRRKKRG, (SEQ ID NO: 26)
RKKASSKIAAEILDAFSQNWRRKRPPRRRQRRKKRG, (SEQ ID NO: 27)
RKKASSKIEAEILDAFSQNWRRKRPPRRRQRRKKRG, (SEQ ID NO: 28)
RKKSKIAAAILDAFSQNWRRKRRRRQRRKKRG, (SEQ ID NO: 29)
RKKSKIEAEILDAFSQNWRRKRRRRQRRKKRG, (SEQ ID NO: 30)
AKIAAAILDAFSQNWRRKRRRRQRRKKRG, (SEQ ID NO: 31)
AKIEAAILDAFSQNWRRKRRRRQRRKKRG, (SEQ ID NO: 53)
RKKASSKIEAEILDAFSQNWRRKRPPRRRQRRKKRG, (SEQ ID NO: 54)
RKKSKIEAEILDAFSQNWRKRRRRQRRKKRG, (SEQ ID NO: 55)
AKIEAAILDAFSQNWRKRRRRQRRKKRG, (SEQ ID NO: 56)
AKIEAEILDAFSQNWRKRRRRQRRKKRG, (SEQ ID NO: 57)
AKIEAAILDEFSQNWRKRRRRQRRKKRG, (SEQ ID NO: 58)
RKKASJKIAJAILDAFSQNWRRKRPPRRRQRRKKRG, (SEQ ID NO: 59)
RKKASSKIAAAZLDAFSQNAWANRRSSCKRPPPRRRQRRKKRA, (SEQ ID NO: 60)
AKIEAAILDAFSQNBRKRRRRQRRKKRG, (SEQ ID NO: 61)
AKIEAEILEAFSQNBRKRRRRQRRKKRG, (SEQ ID NO: 62)
AKIEAAZLDAFSQNBRKRRRRQRRKKRG,
```

-continued

```
                                   (SEQ ID NO: 63)
RKKASSKIEAEILDAFSQNBRRKRPPRRRQRRKKRG, (SEQ ID NO: 64)
RKKASSKIEAEZLDAFSQNBRRKRPPRRRQRRKKRG, (SEQ ID NO: 65)
RKKASSKIEAEIZDAFSQNBRRKRPPRRRQRRKKRG, (SEQ ID NO: 67)
RKKSKIAAAILDAFSQNWRKRRRRQRRKKRG, and (SEQ ID NO: 68)
RKKASSKIEAAILDAFSQNWRRKRPPRRRQRRKKRG,
``` wherein Z is Cyclo-Hexyl-Alanine, and B is 2-Methyl-Tryptophan, and pharmaceutically acceptable salts thereof; and ii) a peptide according to i) comprising at least 80% D-amino acids, and pharmaceutically acceptable salts thereof.

2. A method for manufacturing a pharmaceutical composition for treating or preventing senescent cells, scarred cell and/or cancer cells in a subject, comprising the steps of:

A) providing a peptide according to claim 1, and B) formulating said peptide as provided into a pharmaceutical composition.

3. A pharmaceutical composition for treating or preventing senescent cells in a subject, wherein said composition comprises:

A) the peptide according to claim 1; and

B) at least one pharmaceutically acceptable carrier.

4. The pharmaceutical composition according to claim 3, further comprising one or more additional pharmaceutically active ingredients.

5. The peptide according to claim 1, further comprising the cell-penetrating TAT-sequence of HIV (GRKKRRQRRRPP (SEQ ID NO: 41) or ARKKRRQRRRPPP (SEQ ID NO: 66)).

6. The peptide according to claim 1, comprising an amino acid sequence selected from the group consisting of

```
                                   (SEQ ID NO: 7)
LTLRKEASSEIAQSILDAYSQNGWANRRSSCKRP, (SEQ ID NO: 8)
LTLRKKASSKIAQSILDAFSQNGWANRRSSCKRP, (SEQ ID NO: 9)
LTLRKEPASEIAQSILEAYSQNGWANRRSGGKRP, (SEQ ID NO: 10)
RKKASSKIAQSILDAFSQNGWANRRSSCKRP, (SEQ ID NO: 11)
RKKASSKIAAAILDAFSQNGWANRRSSCKRP, (SEQ ID NO: 12)
RKKASSKIAAAILDAFSQNAWANRRSSCKRP, (SEQ ID NO: 13)
RKKASSKIAAAILDAFSQNWRRKR, (SEQ ID NO: 14)
RKKASSKIEAAILDAFSQNWRRKR, (SEQ ID NO: 15)
RKKASSKIAAEILDAFSQNWRRKR, (SEQ ID NO: 16)
RKKASSKIEAEILDAFSQNWRRKR,
```

-continued (SEQ ID NO: 17)
RKKSKIAAAILDAFSQNWRRKR, (SEQ ID NO: 18)
RKKSKIEAEILDAFSQNWRRKR, (SEQ ID NO: 19)
AKIAAAILDAFSQNWRRKR, (SEQ ID NO: 20)
AKIEAAILDAFSQNWRRKR, (SEQ ID NO: 22)
RKKASSKIAAAILDAFSQNGWANRRSSCKRPPPRRRQRRKKRG, (SEQ ID NO: 23)
RKKASSKIAAAILDAFSQNAWANRRSSCKRPPPRRRQRRKKRA, (SEQ ID NO: 24)
RKKASSKIAAAILDAFSQNWRRKRPPRRRQRRKKRG, (SEQ ID NO: 25)
RKKASSKIEAAILDAFSQNWRRKRPPRRRQRRKKRG, (SEQ ID NO: 26)
RKKASSKIAAEILDAFSQNWRRKRPPRRRQRRKKRG, (SEQ ID NO: 27)
RKKASSKIEAEILDAFSQNWRRKRPPRRRQRRKKRG, (SEQ ID NO: 28)
RKKSKIAAAILDAFSQNWRRKRRRRQRRKKRG, (SEQ ID NO: 29)
RKKSKIEAEILDAFSQNWRRKRRRRQRRKKRG, (SEQ ID NO: 30)
AKIAAAILDAFSQNWRRKRRRRQRRKKRG, (SEQ ID NO: 31)
AKIEAAILDAFSQNWRRKRRRRQRRKKRG, -continued (SEQ ID NO: 53)
RKKASSKIEAEILDAFSQNWRRKRPPRRRQRRKKRG, (SEQ ID NO: 54)
RKKSKIEAEILDAFSQNWRKRRRRQRRKKRG, (SEQ ID NO: 55)
AKIEAAILDAFSQNWRKRRRRQRRKKRG, (SEQ ID NO: 56)
AKIEAEILDAFSQNWRKRRRRQRRKKRG, (SEQ ID NO: 57)
AKIEAAILDEFSQNWRKRRRRQRRKKRG, (SEQ ID NO: 58)
RKKASJKIAJAILDAFSQNWRRKRPPRRRQRRKKRG, (SEQ ID NO: 59)
RKKASSKIAAAZLDAFSQNAWANRRSSCKRPPPRRRQRRKKRA, (SEQ ID NO: 60)
AKIEAAILDAFSQNBRKRRRRQRRKKRG, (SEQ ID NO: 61)
AKIEAEILEAFSQNBRKRRRRQRRKKRG, (SEQ ID NO: 62)
AKIEAAZLDAFSQNBRKRRRRQRRKKRG, (SEQ ID NO: 63)
RKKASSKIEAEILDAFSQNBRRKRPPRRRQRRKKRG, (SEQ ID NO: 64)
RKKASSKIEAEZLDAFSQNBRRKRPPRRRQRRKKRG,
and (SEQ ID NO: 65)
RKKASSKIEAEIZDAFSQNBRRKRPPRRRQRRKKRG.

* * * * *

SEQUENCE LISTING

<160> NUMBER OF SEQ ID NOS: 68

<210> SEQ ID NO 1
<211> LENGTH: 25
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be Ala or Ser or Fmoc-L-2-(4'-
    pentenyl)alanine (staple)
<220> FEATURE:
<221> NAME/KEY: misc_feature
<222> LOCATION: (2)..(2)
<223> OTHER INFORMATION: Xaa can be Lys, Glu, Arg, or His
<220> FEATURE:
<221> NAME/KEY: misc_feature
<222> LOCATION: (3)..(3)
<223> OTHER INFORMATION: Xaa can be Ile, Leu, or cyclo-hexyl-alanine
<220> FEATURE:
<221> NAME/KEY: misc_feature
<222> LOCATION: (4)..(4)
<223> OTHER INFORMATION: Xaa can be Ala, Gly, Ser, Glu, or Asp

```
<220> FEATURE:
<221> NAME/KEY: misc_feature
<222> LOCATION: (5)..(5)
<223> OTHER INFORMATION: Xaa can be Gly, Gln, Ala, Ser, or Pro or
      Fmoc-L-2-(4'-pentenyl)alanine (stable)
<220> FEATURE:
<221> NAME/KEY: misc_feature
<222> LOCATION: (6)..(6)
<223> OTHER INFORMATION: Xaa can be Ala, Gly, Ser, Glu, or Asp
<220> FEATURE:
<221> NAME/KEY: misc_feature
<222> LOCATION: (7)..(8)
<223> OTHER INFORMATION: Xaa can be Ile, Leu, or cyclo-hexyl-alanine
<220> FEATURE:
<221> NAME/KEY: misc_feature
<222> LOCATION: (9)..(9)
<223> OTHER INFORMATION: Xaa can be Glu or Asp
<220> FEATURE:
<221> NAME/KEY: misc_feature
<222> LOCATION: (10)..(10)
<223> OTHER INFORMATION: Xaa can be Ala or Glu
<220> FEATURE:
<221> NAME/KEY: misc_feature
<222> LOCATION: (11)..(11)
<223> OTHER INFORMATION: Xaa can be Trp, Tyr, or Phe or 2-Me-tryptophane
<220> FEATURE:
<221> NAME/KEY: misc_feature
<222> LOCATION: (12)..(12)
<223> OTHER INFORMATION: Xaa can be Ala or Ser or Fmoc-L-2-(4'-
      pentenyl)alanine (staple)
<220> FEATURE:
<221> NAME/KEY: misc_feature
<222> LOCATION: (15)..(15)
<223> OTHER INFORMATION: Xaa can be Ala or Gly
<220> FEATURE:
<221> NAME/KEY: misc_feature
<222> LOCATION: (16)..(16)
<223> OTHER INFORMATION: Xaa can be Trp, Tyr, or Phe or 2-Me-tryptophane
<220> FEATURE:
<221> NAME/KEY: misc_feature
<222> LOCATION: (17)..(18)
<223> OTHER INFORMATION: Xaa can be Ala
<220> FEATURE:
<221> NAME/KEY: misc_feature
<222> LOCATION: (19)..(19)
<223> OTHER INFORMATION: Xaa can be Arg or Lys
<220> FEATURE:
<221> NAME/KEY: misc_feature
<222> LOCATION: (20)..(20)
<223> OTHER INFORMATION: Xaa can be Arg
<220> FEATURE:
<221> NAME/KEY: misc_feature
<222> LOCATION: (22)..(22)
<223> OTHER INFORMATION: Xaa can be Gly or Ser
<220> FEATURE:
<221> NAME/KEY: misc_feature
<222> LOCATION: (23)..(23)
<223> OTHER INFORMATION: Xaa can be Ala or Cys
<220> FEATURE:
<221> NAME/KEY: misc_feature
<222> LOCATION: (24)..(25)
<223> OTHER INFORMATION: Xaa can be Arg or Lys

<400> SEQUENCE: 1

Xaa Xaa Xaa Xaa Xaa Xaa Xaa Xaa Xaa Xaa Xaa Xaa Gln Asn Xaa Xaa
1               5                   10                  15

Xaa Xaa Xaa Xaa Ser Xaa Xaa Xaa Xaa
            20                  25

<210> SEQ ID NO 2
<211> LENGTH: 32
<212> TYPE: PRT
<213> ORGANISM: Homo sapiens
<220> FEATURE:
<221> NAME/KEY: misc_feature
<222> LOCATION: (1)..(1)
```

```
<223> OTHER INFORMATION: Xaa can be Leu Thr Leu
<220> FEATURE:
<221> NAME/KEY: misc_feature
<222> LOCATION: (2)..(2)
<223> OTHER INFORMATION: Xaa can be Arg or Ser
<220> FEATURE:
<221> NAME/KEY: misc_feature
<222> LOCATION: (4)..(4)
<223> OTHER INFORMATION: Xaa can be Lys, Glu, Arg, and His
<220> FEATURE:
<221> NAME/KEY: misc_feature
<222> LOCATION: (5)..(5)
<223> OTHER INFORMATION: Xaa can be Ala or Pro
<220> FEATURE:
<221> NAME/KEY: misc_feature
<222> LOCATION: (6)..(6)
<223> OTHER INFORMATION: Xaa can be Ala or Ser
<220> FEATURE:
<221> NAME/KEY: misc_feature
<222> LOCATION: (7)..(7)
<223> OTHER INFORMATION: Xaa can be Ala or Ser or Fmoc-L-2-(4'-
      pentenyl)alanine (staple)
<220> FEATURE:
<221> NAME/KEY: misc_feature
<222> LOCATION: (8)..(8)
<223> OTHER INFORMATION: Xaa can be Lys, Glu, Arg, or His
<220> FEATURE:
<221> NAME/KEY: misc_feature
<222> LOCATION: (9)..(9)
<223> OTHER INFORMATION: Xaa can be Ile or Leu or cyclo-hexyl-alanine
<220> FEATURE:
<221> NAME/KEY: misc_feature
<222> LOCATION: (10)..(10)
<223> OTHER INFORMATION: Xaa can be Ala, Gly, Ser, Glu, or Asp
<220> FEATURE:
<221> NAME/KEY: misc_feature
<222> LOCATION: (11)..(11)
<223> OTHER INFORMATION: Xaa can be Gly, Gln, Ala, Ser, or Pro or
      Fmoc-L-2-(4'-pentenyl)alanine (staple)
<220> FEATURE:
<221> NAME/KEY: misc_feature
<222> LOCATION: (12)..(12)
<223> OTHER INFORMATION: Xaa can be Ala, Gly, Ser, Glu, or Asp
<220> FEATURE:
<221> NAME/KEY: misc_feature
<222> LOCATION: (13)..(14)
<223> OTHER INFORMATION: Xaa can be Ile or Leu or cyclo-hexyl-alanine
<220> FEATURE:
<221> NAME/KEY: misc_feature
<222> LOCATION: (15)..(15)
<223> OTHER INFORMATION: Xaa can be Glu or Asp
<220> FEATURE:
<221> NAME/KEY: misc_feature
<222> LOCATION: (17)..(17)
<223> OTHER INFORMATION: Xaa can be Trp, Tyr, and Phe
<220> FEATURE:
<221> NAME/KEY: misc_feature
<222> LOCATION: (18)..(18)
<223> OTHER INFORMATION: Xaa can be Ala or Ser or Fmoc-L-2-(4'-
      pentenyl)alanine (staple)
<220> FEATURE:
<221> NAME/KEY: misc_feature
<222> LOCATION: (21)..(21)
<223> OTHER INFORMATION: Xaa can be Ala or Gly
<220> FEATURE:
<221> NAME/KEY: misc_feature
<222> LOCATION: (22)..(22)
<223> OTHER INFORMATION: Xaa can be Trp, Tyr, and Phe
<220> FEATURE:
<221> NAME/KEY: misc_feature
<222> LOCATION: (23)..(24)
<223> OTHER INFORMATION: Xaa can be Ala
<220> FEATURE:
<221> NAME/KEY: misc_feature
<222> LOCATION: (25)..(25)
<223> OTHER INFORMATION: Xaa can be Arg or Lys
<220> FEATURE:
<221> NAME/KEY: misc_feature
<222> LOCATION: (26)..(26)
```

```
<223> OTHER INFORMATION: Xaa can be Arg
<220> FEATURE:
<221> NAME/KEY: misc_feature
<222> LOCATION: (28)..(28)
<223> OTHER INFORMATION: Xaa can be Gly or Ser
<220> FEATURE:
<221> NAME/KEY: misc_feature
<222> LOCATION: (29)..(29)
<223> OTHER INFORMATION: Xaa can be Ala or Cys
<220> FEATURE:
<221> NAME/KEY: misc_feature
<222> LOCATION: (30)..(31)
<223> OTHER INFORMATION: Xaa can be Arg or Lys
<220> FEATURE:
<221> NAME/KEY: misc_feature
<222> LOCATION: (32)..(32)
<223> OTHER INFORMATION: Xaa can be Ala or Cys

<400> SEQUENCE: 2

Xaa Xaa Lys Xaa Xaa Xaa Xaa Xaa Xaa Xaa Xaa Xaa Xaa Xaa Xaa Ala
1               5                   10                  15

Xaa Xaa Gln Asn Xaa Xaa Xaa Xaa Xaa Xaa Ser Xaa Xaa Xaa Xaa Xaa
            20                  25                  30

<210> SEQ ID NO 3
<211> LENGTH: 14
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be Ile or Leu
<220> FEATURE:
<221> NAME/KEY: misc_feature
<222> LOCATION: (2)..(2)
<223> OTHER INFORMATION: Xaa can be Ala, Gly, Ser, Glu, or Asp
<220> FEATURE:
<221> NAME/KEY: misc_feature
<222> LOCATION: (3)..(3)
<223> OTHER INFORMATION: Xaa can be Gly, Gln, Ala, Ser, or Pro or
      Fmoc-L-2-(4'-pentenyl)alanine (staple)
<220> FEATURE:
<221> NAME/KEY: misc_feature
<222> LOCATION: (4)..(4)
<223> OTHER INFORMATION: Xaa can be Ala, Gly, Ser, Glu, or Asp
<220> FEATURE:
<221> NAME/KEY: misc_feature
<222> LOCATION: (5)..(6)
<223> OTHER INFORMATION: Xaa can be Ile or Leu
<220> FEATURE:
<221> NAME/KEY: misc_feature
<222> LOCATION: (7)..(7)
<223> OTHER INFORMATION: Xaa can be Glu or Asp
<220> FEATURE:
<221> NAME/KEY: misc_feature
<222> LOCATION: (9)..(9)
<223> OTHER INFORMATION: Xaa can be Trp, Tyr, and Phe
<220> FEATURE:
<221> NAME/KEY: misc_feature
<222> LOCATION: (10)..(10)
<223> OTHER INFORMATION: Xaa can be Ala or Ser or Fmoc-L-2-(4'-
      pentenyl)alanine (staple)
<220> FEATURE:
<221> NAME/KEY: misc_feature
<222> LOCATION: (13)..(13)
<223> OTHER INFORMATION: Xaa can be Ala or Gly
<220> FEATURE:
<221> NAME/KEY: misc_feature
<222> LOCATION: (14)..(14)
<223> OTHER INFORMATION: Xaa can be Trp, Tyr, and Phe

<400> SEQUENCE: 3

Xaa Xaa Xaa Xaa Xaa Xaa Xaa Ala Xaa Xaa Gln Asn Xaa Xaa
1               5                   10
```

```
<210> SEQ ID NO 4
<211> LENGTH: 14
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be Ala, Gly, Ser, Glu, or Asp
<220> FEATURE:
<221> NAME/KEY: misc_feature
<222> LOCATION: (3)..(3)
<223> OTHER INFORMATION: Xaa can be Gly, Gln, Ala, Ser, or Pro
<220> FEATURE:
<221> NAME/KEY: misc_feature
<222> LOCATION: (4)..(4)
<223> OTHER INFORMATION: Xaa can be Ala, Gly, Ser, Glu, or Asp
<220> FEATURE:
<221> NAME/KEY: misc_feature
<222> LOCATION: (7)..(7)
<223> OTHER INFORMATION: Xaa can be Glu or Asp
<220> FEATURE:
<221> NAME/KEY: misc_feature
<222> LOCATION: (10)..(10)
<223> OTHER INFORMATION: Xaa can be Ala or Ser
<220> FEATURE:
<221> NAME/KEY: misc_feature
<222> LOCATION: (13)..(13)
<223> OTHER INFORMATION: Xaa can be Ala or Gly

<400> SEQUENCE: 4

Ile Xaa Xaa Xaa Ile Leu Xaa Ala Phe Xaa Gln Asn Xaa Trp
1               5                   10

<210> SEQ ID NO 5
<211> LENGTH: 34
<212> TYPE: PRT
<213> ORGANISM: Homo sapiens

<400> SEQUENCE: 5

Leu Thr Leu Arg Lys Glu Pro Ala Ser Glu Ile Ala Gln Ser Ile Leu
1               5                   10                  15

Glu Ala Tyr Ser Gln Asn Gly Trp Ala Asn Arg Arg Ser Gly Gly Lys
            20                  25                  30

Arg Pro

<210> SEQ ID NO 6
<211> LENGTH: 46
<212> TYPE: PRT
<213> ORGANISM: Homo sapiens

<400> SEQUENCE: 6

Leu Thr Leu Arg Lys Glu Pro Ala Ser Glu Ile Ala Gln Ser Ile Leu
1               5                   10                  15

Glu Ala Tyr Ser Gln Asn Gly Trp Ala Asn Arg Arg Ser Gly Gly Lys
            20                  25                  30

Arg Pro Pro Pro Arg Arg Arg Gln Arg Arg Lys Lys Arg Gly
        35                  40                  45

<210> SEQ ID NO 7
<211> LENGTH: 34
<212> TYPE: PRT
<213> ORGANISM: Homo sapiens

<400> SEQUENCE: 7

Leu Thr Leu Arg Lys Glu Ala Ser Ser Glu Ile Ala Gln Ser Ile Leu
1               5                   10                  15
```

```
Asp Ala Tyr Ser Gln Asn Gly Trp Ala Asn Arg Arg Ser Ser Cys Lys
            20                  25                  30

Arg Pro

<210> SEQ ID NO 8
<211> LENGTH: 34
<212> TYPE: PRT
<213> ORGANISM: Homo sapiens

<400> SEQUENCE: 8

Leu Thr Leu Arg Lys Lys Ala Ser Ser Lys Ile Ala Gln Ser Ile Leu
1               5                   10                  15

Asp Ala Phe Ser Gln Asn Gly Trp Ala Asn Arg Arg Ser Ser Cys Lys
            20                  25                  30

Arg Pro

<210> SEQ ID NO 9
<211> LENGTH: 34
<212> TYPE: PRT
<213> ORGANISM: Homo sapiens

<400> SEQUENCE: 9

Leu Thr Leu Arg Lys Glu Pro Ala Ser Glu Ile Ala Gln Ser Ile Leu
1               5                   10                  15

Glu Ala Tyr Ser Gln Asn Gly Trp Ala Asn Arg Arg Ser Gly Gly Lys
            20                  25                  30

Arg Pro

<210> SEQ ID NO 10
<211> LENGTH: 31
<212> TYPE: PRT
<213> ORGANISM: Homo sapiens

<400> SEQUENCE: 10

Arg Lys Lys Ala Ser Ser Lys Ile Ala Gln Ser Ile Leu Asp Ala Phe
1               5                   10                  15

Ser Gln Asn Gly Trp Ala Asn Arg Arg Ser Ser Cys Lys Arg Pro
            20                  25                  30

<210> SEQ ID NO 11
<211> LENGTH: 31
<212> TYPE: PRT
<213> ORGANISM: Homo sapiens

<400> SEQUENCE: 11

Arg Lys Lys Ala Ser Ser Lys Ile Ala Ala Ala Ile Leu Asp Ala Phe
1               5                   10                  15

Ser Gln Asn Gly Trp Ala Asn Arg Arg Ser Ser Cys Lys Arg Pro
            20                  25                  30

<210> SEQ ID NO 12
<211> LENGTH: 31
<212> TYPE: PRT
<213> ORGANISM: Homo sapiens

<400> SEQUENCE: 12

Arg Lys Lys Ala Ser Ser Lys Ile Ala Ala Ala Ile Leu Asp Ala Phe
1               5                   10                  15

Ser Gln Asn Ala Trp Ala Asn Arg Arg Ser Ser Cys Lys Arg Pro
            20                  25                  30
```

```
<210> SEQ ID NO 13
<211> LENGTH: 24
<212> TYPE: PRT
<213> ORGANISM: Homo sapiens

<400> SEQUENCE: 13

Arg Lys Lys Ala Ser Ser Lys Ile Ala Ala Ala Ile Leu Asp Ala Phe
1               5                   10                  15

Ser Gln Asn Trp Arg Arg Lys Arg
            20

<210> SEQ ID NO 14
<211> LENGTH: 24
<212> TYPE: PRT
<213> ORGANISM: Homo sapiens

<400> SEQUENCE: 14

Arg Lys Lys Ala Ser Ser Lys Ile Glu Ala Ala Ile Leu Asp Ala Phe
1               5                   10                  15

Ser Gln Asn Trp Arg Arg Lys Arg
            20

<210> SEQ ID NO 15
<211> LENGTH: 24
<212> TYPE: PRT
<213> ORGANISM: Homo sapiens

<400> SEQUENCE: 15

Arg Lys Lys Ala Ser Ser Lys Ile Ala Ala Glu Ile Leu Asp Ala Phe
1               5                   10                  15

Ser Gln Asn Trp Arg Arg Lys Arg
            20

<210> SEQ ID NO 16
<211> LENGTH: 24
<212> TYPE: PRT
<213> ORGANISM: Homo sapiens

<400> SEQUENCE: 16

Arg Lys Lys Ala Ser Ser Lys Ile Glu Ala Glu Ile Leu Asp Ala Phe
1               5                   10                  15

Ser Gln Asn Trp Arg Arg Lys Arg
            20

<210> SEQ ID NO 17
<211> LENGTH: 22
<212> TYPE: PRT
<213> ORGANISM: Homo sapiens

<400> SEQUENCE: 17

Arg Lys Lys Ser Lys Ile Ala Ala Ala Ile Leu Asp Ala Phe Ser Gln
1               5                   10                  15

Asn Trp Arg Arg Lys Arg
            20

<210> SEQ ID NO 18
<211> LENGTH: 22
<212> TYPE: PRT
<213> ORGANISM: Homo sapiens

<400> SEQUENCE: 18

Arg Lys Lys Ser Lys Ile Glu Ala Glu Ile Leu Asp Ala Phe Ser Gln
```

-continued

```
1               5              10             15

Asn Trp Arg Arg Lys Arg
            20

<210> SEQ ID NO 19
<211> LENGTH: 19
<212> TYPE: PRT
<213> ORGANISM: Homo sapiens

<400> SEQUENCE: 19

Ala Lys Ile Ala Ala Ala Ile Leu Asp Ala Phe Ser Gln Asn Trp Arg
1               5              10             15

Arg Lys Arg

<210> SEQ ID NO 20
<211> LENGTH: 19
<212> TYPE: PRT
<213> ORGANISM: Homo sapiens

<400> SEQUENCE: 20

Ala Lys Ile Glu Ala Ala Ile Leu Asp Ala Phe Ser Gln Asn Trp Arg
1               5              10             15

Arg Lys Arg

<210> SEQ ID NO 21
<211> LENGTH: 46
<212> TYPE: PRT
<213> ORGANISM: Homo sapiens

<400> SEQUENCE: 21

Leu Thr Leu Arg Lys Glu Pro Ala Ser Glu Ile Ala Gln Ser Ile Leu
1               5              10             15

Glu Ala Tyr Ser Gln Asn Gly Trp Ala Asn Arg Arg Ser Gly Gly Lys
            20             25             30

Arg Pro Pro Pro Arg Arg Arg Gln Arg Arg Lys Lys Arg Gly
            35             40             45

<210> SEQ ID NO 22
<211> LENGTH: 43
<212> TYPE: PRT
<213> ORGANISM: Homo sapiens

<400> SEQUENCE: 22

Arg Lys Lys Ala Ser Ser Lys Ile Ala Ala Ala Ile Leu Asp Ala Phe
1               5              10             15

Ser Gln Asn Gly Trp Ala Asn Arg Arg Ser Ser Cys Lys Arg Pro Pro
            20             25             30

Pro Arg Arg Arg Gln Arg Arg Lys Lys Arg Gly
            35             40

<210> SEQ ID NO 23
<211> LENGTH: 43
<212> TYPE: PRT
<213> ORGANISM: Homo sapiens

<400> SEQUENCE: 23

Arg Lys Lys Ala Ser Ser Lys Ile Ala Ala Ala Ile Leu Asp Ala Phe
1               5              10             15

Ser Gln Asn Ala Trp Ala Asn Arg Arg Ser Ser Cys Lys Arg Pro Pro
            20             25             30
```

-continued

```
Pro Arg Arg Arg Gln Arg Arg Lys Lys Arg Ala
        35              40

<210> SEQ ID NO 24
<211> LENGTH: 36
<212> TYPE: PRT
<213> ORGANISM: Homo sapiens

<400> SEQUENCE: 24

Arg Lys Lys Ala Ser Ser Lys Ile Ala Ala Ala Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 25
<211> LENGTH: 36
<212> TYPE: PRT
<213> ORGANISM: Homo sapiens

<400> SEQUENCE: 25

Arg Lys Lys Ala Ser Ser Lys Ile Glu Ala Ala Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 26
<211> LENGTH: 36
<212> TYPE: PRT
<213> ORGANISM: Homo sapiens

<400> SEQUENCE: 26

Arg Lys Lys Ala Ser Ser Lys Ile Ala Ala Glu Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 27
<211> LENGTH: 36
<212> TYPE: PRT
<213> ORGANISM: Homo sapiens

<400> SEQUENCE: 27

Arg Lys Lys Ala Ser Ser Lys Ile Glu Ala Glu Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 28
<211> LENGTH: 32
<212> TYPE: PRT
<213> ORGANISM: Homo sapiens

<400> SEQUENCE: 28
```

-continued

```
Arg Lys Lys Ser Lys Ile Ala Ala Ala Ile Leu Asp Ala Phe Ser Gln
1               5                   10                  15

Asn Trp Arg Arg Lys Arg Arg Arg Gln Arg Arg Lys Lys Arg Gly
            20                  25                  30

<210> SEQ ID NO 29
<211> LENGTH: 32
<212> TYPE: PRT
<213> ORGANISM: Homo sapiens

<400> SEQUENCE: 29

Arg Lys Lys Ser Lys Ile Glu Ala Glu Ile Leu Asp Ala Phe Ser Gln
1               5                   10                  15

Asn Trp Arg Arg Lys Arg Arg Arg Gln Arg Arg Lys Lys Arg Gly
            20                  25                  30

<210> SEQ ID NO 30
<211> LENGTH: 29
<212> TYPE: PRT
<213> ORGANISM: Homo sapiens

<400> SEQUENCE: 30

Ala Lys Ile Ala Ala Ala Ile Leu Asp Ala Phe Ser Gln Asn Trp Arg
1               5                   10                  15

Arg Lys Arg Arg Arg Arg Gln Arg Arg Lys Lys Arg Gly
            20                  25

<210> SEQ ID NO 31
<211> LENGTH: 29
<212> TYPE: PRT
<213> ORGANISM: Homo sapiens

<400> SEQUENCE: 31

Ala Lys Ile Glu Ala Ala Ile Leu Asp Ala Phe Ser Gln Asn Trp Arg
1               5                   10                  15

Arg Lys Arg Arg Arg Arg Gln Arg Arg Lys Lys Arg Gly
            20                  25

<210> SEQ ID NO 32
<211> LENGTH: 91
<212> TYPE: PRT
<213> ORGANISM: Homo sapiens

<400> SEQUENCE: 32

Pro Arg Lys Gly Gly Ser Arg Arg Asn Ala Trp Gly Asn Gln Ser Tyr
1               5                   10                  15

Ala Glu Leu Ile Ser Gln Ala Ile Glu Ser Ala Pro Glu Lys Arg Leu
            20                  25                  30

Thr Leu Ala Gln Ile Tyr Glu Trp Met Val Arg Thr Val Pro Tyr Phe
        35                  40                  45

Lys Asp Lys Gly Asp Ser Asn Ser Ser Ala Gly Trp Lys Asn Ser Ile
    50                  55                  60

Arg His Asn Leu Ser Leu His Ser Lys Phe Ile Lys Val His Asn Glu
65                  70                  75                  80

Ala Thr Gly Lys Ser Ser Trp Trp Met Leu Asn
                85                  90

<210> SEQ ID NO 33
<211> LENGTH: 34
<212> TYPE: PRT
<213> ORGANISM: Homo sapiens
```

<400> SEQUENCE: 33

Pro Arg Lys Gly Gly Ser Arg Arg Asn Ala Trp Gly Asn Gln Ser Tyr
1               5                   10                  15

Ala Glu Leu Ile Ser Gln Ala Ile Glu Ser Ala Pro Glu Lys Arg Leu
            20                  25                  30

Thr Leu

<210> SEQ ID NO 34
<211> LENGTH: 22
<212> TYPE: PRT
<213> ORGANISM: Homo sapiens

<400> SEQUENCE: 34

Ala Met Asp Asp Leu Met Leu Ser Pro Asp Asp Ile Glu Gln Trp Phe
1               5                   10                  15

Thr Glu Asp Pro Gly Pro
            20

<210> SEQ ID NO 35
<211> LENGTH: 10
<212> TYPE: PRT
<213> ORGANISM: Homo sapiens

<400> SEQUENCE: 35

Leu Thr Leu Arg Lys Glu Ala Ser Ser Glu
1               5                   10

<210> SEQ ID NO 36
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be Ala, Gly, Ser, Glu or Asp
<220> FEATURE:
<221> NAME/KEY: misc_feature
<222> LOCATION: (3)..(3)
<223> OTHER INFORMATION: Xaa can be Gly, Gln, Ala, Ser, or Pro
<220> FEATURE:
<221> NAME/KEY: misc_feature
<222> LOCATION: (4)..(4)
<223> OTHER INFORMATION: Xaa can be Ala, Gly, Ser, Glu or Asp

<400> SEQUENCE: 36

Ile Xaa Xaa Xaa Ile Leu
1               5

<210> SEQ ID NO 37
<211> LENGTH: 6
<212> TYPE: PRT
<213> ORGANISM: Homo sapiens

<400> SEQUENCE: 37

Ile Ala Gln Ser Ile Leu
1               5

<210> SEQ ID NO 38
<211> LENGTH: 10
<212> TYPE: PRT
<213> ORGANISM: Homo sapiens

<400> SEQUENCE: 38

Ala Asn Arg Arg Ser Ser Cys Lys Arg Pro

-continued

```
1               5               10
```

```
<210> SEQ ID NO 39
<211> LENGTH: 505
<212> TYPE: PRT
<213> ORGANISM: Homo sapiens

<400> SEQUENCE: 39

Met Asp Pro Gly Asn Glu Asn Ser Ala Thr Glu Ala Ala Ala Ile Ile
1               5               10              15

Asp Leu Asp Pro Asp Phe Glu Pro Gln Ser Arg Pro Arg Ser Cys Thr
                20              25              30

Trp Pro Leu Pro Arg Pro Glu Ile Ala Asn Gln Pro Ser Glu Pro Pro
            35              40              45

Glu Val Glu Pro Asp Leu Gly Glu Lys Val His Thr Glu Gly Arg Ser
        50              55              60

Glu Pro Ile Leu Leu Pro Ser Arg Leu Pro Glu Pro Ala Gly Gly Pro
65              70              75              80

Gln Pro Gly Ile Leu Gly Ala Val Thr Gly Pro Arg Lys Gly Gly Ser
                85              90              95

Arg Arg Asn Ala Trp Gly Asn Gln Ser Tyr Ala Glu Leu Ile Ser Gln
            100             105             110

Ala Ile Glu Ser Ala Pro Glu Lys Arg Leu Thr Leu Ala Gln Ile Tyr
            115             120             125

Glu Trp Met Val Arg Thr Val Pro Tyr Phe Lys Asp Lys Gly Asp Ser
        130             135             140

Asn Ser Ser Ala Gly Trp Lys Asn Ser Ile Arg His Asn Leu Ser Leu
145             150             155             160

His Ser Lys Phe Ile Lys Val His Asn Glu Ala Thr Gly Lys Ser Ser
                165             170             175

Trp Trp Met Leu Asn Pro Glu Gly Gly Lys Ser Gly Lys Ala Pro Arg
            180             185             190

Arg Arg Ala Ala Ser Met Asp Ser Ser Ser Lys Leu Leu Arg Gly Arg
            195             200             205

Ser Lys Ala Pro Lys Lys Lys Pro Ser Val Leu Pro Ala Pro Pro Glu
        210             215             220

Gly Ala Thr Pro Thr Ser Pro Val Gly His Phe Ala Lys Trp Ser Gly
225             230             235             240

Ser Pro Cys Ser Arg Asn Arg Glu Glu Ala Asp Met Trp Thr Thr Phe
                245             250             255

Arg Pro Arg Ser Ser Ser Asn Ala Ser Ser Val Ser Thr Arg Leu Ser
            260             265             270

Pro Leu Arg Pro Glu Ser Glu Val Leu Ala Glu Glu Ile Pro Ala Ser
            275             280             285

Val Ser Ser Tyr Ala Gly Gly Val Pro Pro Thr Leu Asn Glu Gly Leu
        290             295             300

Glu Leu Leu Asp Gly Leu Asn Leu Thr Ser Ser His Ser Leu Leu Ser
305             310             315             320

Arg Ser Gly Leu Ser Gly Phe Ser Leu Gln His Pro Gly Val Thr Gly
                325             330             335

Pro Leu His Thr Tyr Ser Ser Ser Leu Phe Ser Pro Ala Glu Gly Pro
            340             345             350

Leu Ser Ala Gly Glu Gly Cys Phe Ser Ser Ser Gln Ala Leu Glu Ala
            355             360             365
```

-continued

```
Leu Leu Thr Ser Asp Thr Pro Pro Pro Ala Asp Val Leu Met Thr
    370             375             380

Gln Val Asp Pro Ile Leu Ser Gln Ala Pro Thr Leu Leu Leu Leu Gly
385             390             395             400

Gly Leu Pro Ser Ser Ser Lys Leu Ala Thr Gly Val Gly Leu Cys Pro
            405             410             415

Lys Pro Leu Glu Ala Pro Gly Pro Ser Ser Leu Val Pro Thr Leu Ser
            420             425             430

Met Ile Ala Pro Pro Val Met Ala Ser Ala Pro Ile Pro Lys Ala
            435             440             445

Leu Gly Thr Pro Val Leu Thr Pro Pro Thr Glu Ala Ala Ser Gln Asp
    450             455             460

Arg Met Pro Gln Asp Leu Asp Leu Asp Met Tyr Met Glu Asn Leu Glu
465             470             475             480

Cys Asp Met Asp Asn Ile Ile Ser Asp Leu Met Asp Glu Gly Glu Gly
            485             490             495

Leu Asp Phe Asn Phe Glu Pro Asp Pro
            500             505

<210> SEQ ID NO 40
<211> LENGTH: 393
<212> TYPE: PRT
<213> ORGANISM: Homo sapiens

<400> SEQUENCE: 40

Met Glu Glu Pro Gln Ser Asp Pro Ser Val Glu Pro Pro Leu Ser Gln
1               5               10              15

Glu Thr Phe Ser Asp Leu Trp Lys Leu Leu Pro Glu Asn Asn Val Leu
            20              25              30

Ser Pro Leu Pro Ser Gln Ala Met Asp Asp Leu Met Leu Ser Pro Asp
            35              40              45

Asp Ile Glu Gln Trp Phe Thr Glu Asp Pro Gly Pro Asp Glu Ala Pro
    50              55              60

Arg Met Pro Glu Ala Ala Pro Pro Val Ala Pro Ala Pro Ala Ala Pro
65              70              75              80

Thr Pro Ala Ala Pro Ala Pro Ala Pro Ser Trp Pro Leu Ser Ser Ser
            85              90              95

Val Pro Ser Gln Lys Thr Tyr Gln Gly Ser Tyr Gly Phe Arg Leu Gly
            100             105             110

Phe Leu His Ser Gly Thr Ala Lys Ser Val Thr Cys Thr Tyr Ser Pro
            115             120             125

Ala Leu Asn Lys Met Phe Cys Gln Leu Ala Lys Thr Cys Pro Val Gln
            130             135             140

Leu Trp Val Asp Ser Thr Pro Pro Pro Gly Thr Arg Val Arg Ala Met
145             150             155             160

Ala Ile Tyr Lys Gln Ser Gln His Met Thr Glu Val Val Arg Arg Cys
            165             170             175

Pro His His Glu Arg Cys Ser Asp Ser Asp Gly Leu Ala Pro Pro Gln
            180             185             190

His Leu Ile Arg Val Glu Gly Asn Leu Arg Val Glu Tyr Leu Asp Asp
            195             200             205

Arg Asn Thr Phe Arg His Ser Val Val Val Pro Tyr Glu Pro Pro Glu
    210             215             220

Val Gly Ser Asp Cys Thr Thr Ile His Tyr Asn Tyr Met Cys Asn Ser
225             230             235             240
```

-continued

```
Ser Cys Met Gly Gly Met Asn Arg Arg Pro Ile Leu Thr Ile Ile Thr
            245             250             255

Leu Glu Asp Ser Ser Gly Asn Leu Leu Gly Arg Asn Ser Phe Glu Val
            260             265             270

Arg Val Cys Ala Cys Pro Gly Arg Asp Arg Arg Thr Glu Glu Glu Asn
        275             280             285

Leu Arg Lys Lys Gly Glu Pro His His Glu Leu Pro Pro Gly Ser Thr
    290             295             300

Lys Arg Ala Leu Pro Asn Asn Thr Ser Ser Ser Pro Gln Pro Lys Lys
305             310             315             320

Lys Pro Leu Asp Gly Glu Tyr Phe Thr Leu Gln Ile Arg Gly Arg Glu
                325             330             335

Arg Phe Glu Met Phe Arg Glu Leu Asn Glu Ala Leu Glu Leu Lys Asp
            340             345             350

Ala Gln Ala Gly Lys Glu Pro Gly Gly Ser Arg Ala His Ser Ser His
        355             360             365

Leu Lys Ser Lys Lys Gly Gln Ser Thr Ser Arg His Lys Lys Leu Met
    370             375             380

Phe Lys Thr Glu Gly Pro Asp Ser Asp
385             390

<210> SEQ ID NO 41
<211> LENGTH: 12
<212> TYPE: PRT
<213> ORGANISM: Homo sapiens

<400> SEQUENCE: 41

Gly Arg Lys Lys Arg Arg Gln Arg Arg Pro Pro
1               5               10

<210> SEQ ID NO 42
<211> LENGTH: 34
<212> TYPE: PRT
<213> ORGANISM: Homo sapiens

<400> SEQUENCE: 42

Pro Arg Lys Gly Gly Ser Arg Arg Asn Ala Trp Gly Asn Gln Ser Tyr
1               5               10              15

Ala Glu Leu Ile Ser Gln Ala Ile Glu Ser Ala Pro Glu Lys Arg Leu
            20              25              30

Thr Leu

<210> SEQ ID NO 43
<211> LENGTH: 5
<212> TYPE: PRT
<213> ORGANISM: Homo sapiens

<400> SEQUENCE: 43

Ser Gln Asn Ala Trp
1               5

<210> SEQ ID NO 44
<211> LENGTH: 5
<212> TYPE: PRT
<213> ORGANISM: Homo sapiens

<400> SEQUENCE: 44

Ser Gln Asn Gly Trp
1               5
```

```
<210> SEQ ID NO 45
<211> LENGTH: 4
<212> TYPE: PRT
<213> ORGANISM: Homo sapiens

<400> SEQUENCE: 45

Ser Gln Asn Trp
1

<210> SEQ ID NO 46
<211> LENGTH: 5
<212> TYPE: PRT
<213> ORGANISM: Homo sapiens

<400> SEQUENCE: 46

Lys Ile Ala Ala Ala
1               5

<210> SEQ ID NO 47
<211> LENGTH: 5
<212> TYPE: PRT
<213> ORGANISM: Homo sapiens

<400> SEQUENCE: 47

Lys Ile Glu Ala Ala
1               5

<210> SEQ ID NO 48
<211> LENGTH: 5
<212> TYPE: PRT
<213> ORGANISM: Homo sapiens

<400> SEQUENCE: 48

Lys Ile Ala Ala Glu
1               5

<210> SEQ ID NO 49
<211> LENGTH: 5
<212> TYPE: PRT
<213> ORGANISM: Homo sapiens

<400> SEQUENCE: 49

Lys Ile Glu Ala Glu
1               5

<210> SEQ ID NO 50
<211> LENGTH: 4
<212> TYPE: PRT
<213> ORGANISM: Homo sapiens

<400> SEQUENCE: 50

Ser Gln Asn Gly
1

<210> SEQ ID NO 51
<211> LENGTH: 4
<212> TYPE: PRT
<213> ORGANISM: Homo sapiens

<400> SEQUENCE: 51

Ala Ala Asn Gly
1
```

```
<210> SEQ ID NO 52
<211> LENGTH: 4
<212> TYPE: PRT
<213> ORGANISM: Homo sapiens

<400> SEQUENCE: 52

Ser Gln Ala Gly
1

<210> SEQ ID NO 53
<211> LENGTH: 36
<212> TYPE: PRT
<213> ORGANISM: Homo sapiens

<400> SEQUENCE: 53

Arg Lys Lys Ala Ser Ser Lys Ile Glu Ala Glu Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 54
<211> LENGTH: 31
<212> TYPE: PRT
<213> ORGANISM: Homo sapiens

<400> SEQUENCE: 54

Arg Lys Lys Ser Lys Ile Glu Ala Glu Ile Leu Asp Ala Phe Ser Gln
1               5                   10                  15

Asn Trp Arg Lys Arg Arg Arg Arg Gln Arg Arg Lys Lys Arg Gly
            20                  25                  30

<210> SEQ ID NO 55
<211> LENGTH: 28
<212> TYPE: PRT
<213> ORGANISM: Homo sapiens

<400> SEQUENCE: 55

Ala Lys Ile Glu Ala Ala Ile Leu Asp Ala Phe Ser Gln Asn Trp Arg
1               5                   10                  15

Lys Arg Arg Arg Arg Gln Arg Arg Lys Lys Arg Gly
            20                  25

<210> SEQ ID NO 56
<211> LENGTH: 28
<212> TYPE: PRT
<213> ORGANISM: Homo sapiens

<400> SEQUENCE: 56

Ala Lys Ile Glu Ala Glu Ile Leu Asp Ala Phe Ser Gln Asn Trp Arg
1               5                   10                  15

Lys Arg Arg Arg Gln Arg Arg Lys Lys Arg Gly
            20                  25

<210> SEQ ID NO 57
<211> LENGTH: 28
<212> TYPE: PRT
<213> ORGANISM: Homo sapiens

<400> SEQUENCE: 57

Ala Lys Ile Glu Ala Ala Ile Leu Asp Glu Phe Ser Gln Asn Trp Arg
1               5                   10                  15
```

Lys Arg Arg Arg Arg Gln Arg Arg Lys Lys Arg Gly
            20                  25

<210> SEQ ID NO 58
<211> LENGTH: 36
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Fmoc-L-2-(4'-pentenyl)alanine
<220> FEATURE:
<221> NAME/KEY: misc_feature
<222> LOCATION: (10)..(10)
<223> OTHER INFORMATION: Fmoc-L-2-(4'-pentenyl)alanine

<400> SEQUENCE: 58

Arg Lys Lys Ala Ser Xaa Lys Ile Ala Xaa Ala Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35

<210> SEQ ID NO 59
<211> LENGTH: 43
<212> TYPE: PRT
<213> ORGANISM: Homo sapiens
<220> FEATURE:
<221> NAME/KEY: misc_feature
<222> LOCATION: (12)..(12)
<223> OTHER INFORMATION: cyclo-hexyl-alanine

<400> SEQUENCE: 59

Arg Lys Lys Ala Ser Ser Lys Ile Ala Ala Ala Xaa Leu Asp Ala Phe
1               5                   10                  15

Ser Gln Asn Ala Trp Ala Asn Arg Arg Ser Ser Cys Lys Arg Pro Pro
            20                  25                  30

Pro Arg Arg Arg Gln Arg Arg Lys Lys Arg Ala
        35                  40

<210> SEQ ID NO 60
<211> LENGTH: 28
<212> TYPE: PRT
<213> ORGANISM: Homo sapiens
<220> FEATURE:
<221> NAME/KEY: misc_feature
<222> LOCATION: (15)..(15)
<223> OTHER INFORMATION: 2-Me-tryptophane

<400> SEQUENCE: 60

Ala Lys Ile Glu Ala Ala Ile Leu Asp Ala Phe Ser Gln Asn Xaa Arg
1               5                   10                  15

Lys Arg Arg Arg Arg Gln Arg Arg Lys Lys Arg Gly
            20                  25

<210> SEQ ID NO 61
<211> LENGTH: 28
<212> TYPE: PRT
<213> ORGANISM: Homo sapiens
<220> FEATURE:
<221> NAME/KEY: misc_feature
<222> LOCATION: (15)..(15)
<223> OTHER INFORMATION: 2-Me-tryptophane

<400> SEQUENCE: 61

-continued

```
Ala Lys Ile Glu Ala Glu Ile Leu Glu Ala Phe Ser Gln Asn Xaa Arg
1               5                   10                  15

Lys Arg Arg Arg Arg Gln Arg Arg Lys Lys Arg Gly
            20                  25

<210> SEQ ID NO 62
<211> LENGTH: 28
<212> TYPE: PRT
<213> ORGANISM: Homo sapiens
<220> FEATURE:
<221> NAME/KEY: misc_feature
<222> LOCATION: (7)..(7)
<223> OTHER INFORMATION: cyclo-hexyl-alanine
<220> FEATURE:
<221> NAME/KEY: misc_feature
<222> LOCATION: (15)..(15)
<223> OTHER INFORMATION: 2-Me-tryptophane

<400> SEQUENCE: 62

Ala Lys Ile Glu Ala Ala Xaa Leu Asp Ala Phe Ser Gln Asn Xaa Arg
1               5                   10                  15

Lys Arg Arg Arg Arg Gln Arg Arg Lys Lys Arg Gly
            20                  25

<210> SEQ ID NO 63
<211> LENGTH: 36
<212> TYPE: PRT
<213> ORGANISM: Homo sapiens
<220> FEATURE:
<221> NAME/KEY: misc_feature
<222> LOCATION: (20)..(20)
<223> OTHER INFORMATION: 2-Me-tryptophane

<400> SEQUENCE: 63

Arg Lys Lys Ala Ser Ser Lys Ile Glu Ala Glu Ile Leu Asp Ala Phe
1               5                   10                  15

Ser Gln Asn Xaa Arg Arg Lys Arg Pro Pro Arg Arg Arg Gln Arg Arg
            20                  25                  30

Lys Lys Arg Gly
        35

<210> SEQ ID NO 64
<211> LENGTH: 36
<212> TYPE: PRT
<213> ORGANISM: Homo sapiens
<220> FEATURE:
<221> NAME/KEY: misc_feature
<222> LOCATION: (12)..(12)
<223> OTHER INFORMATION: cyclo-hexyl alanine
<220> FEATURE:
<221> NAME/KEY: misc_feature
<222> LOCATION: (20)..(20)
<223> OTHER INFORMATION: 2-Me-tryptophane

<400> SEQUENCE: 64

Arg Lys Lys Ala Ser Ser Lys Ile Glu Ala Glu Xaa Leu Asp Ala Phe
1               5                   10                  15

Ser Gln Asn Xaa Arg Arg Lys Arg Pro Pro Arg Arg Arg Gln Arg Arg
            20                  25                  30

Lys Lys Arg Gly
        35

<210> SEQ ID NO 65
<211> LENGTH: 36
<212> TYPE: PRT
```

```
<213> ORGANISM: Homo sapiens
<220> FEATURE:
<221> NAME/KEY: misc_feature
<222> LOCATION: (13)..(13)
<223> OTHER INFORMATION: cyclo-hexyl alanine
<220> FEATURE:
<221> NAME/KEY: misc_feature
<222> LOCATION: (20)..(20)
<223> OTHER INFORMATION: 2-Me-tryptophane

<400> SEQUENCE: 65

Arg Lys Lys Ala Ser Ser Lys Ile Glu Ala Glu Ile Xaa Asp Ala Phe
1               5                   10                  15

Ser Gln Asn Xaa Arg Arg Lys Arg Pro Pro Arg Arg Arg Gln Arg Arg
            20                  25                  30

Lys Lys Arg Gly
        35

<210> SEQ ID NO 66
<211> LENGTH: 13
<212> TYPE: PRT
<213> ORGANISM: Homo sapiens

<400> SEQUENCE: 66

Ala Arg Lys Lys Arg Arg Gln Arg Arg Arg Pro Pro Pro
1               5                   10

<210> SEQ ID NO 67
<211> LENGTH: 31
<212> TYPE: PRT
<213> ORGANISM: Homo sapiens

<400> SEQUENCE: 67

Arg Lys Lys Ser Lys Ile Ala Ala Ala Ile Leu Asp Ala Phe Ser Gln
1               5                   10                  15

Asn Trp Arg Lys Arg Arg Arg Arg Gln Arg Arg Lys Lys Arg Gly
            20                  25                  30

<210> SEQ ID NO 68
<211> LENGTH: 36
<212> TYPE: PRT
<213> ORGANISM: Homo sapiens

<400> SEQUENCE: 68

Arg Lys Lys Ala Ser Ser Lys Ile Glu Ala Ala Ile Leu Asp Ala Phe
1               5                   10                  15

Ser Gln Asn Trp Arg Arg Lys Arg Pro Pro Arg Arg Arg Gln Arg Arg
            20                  25                  30

Lys Lys Arg Gly
        35
```